United States Patent [19]

Tamai et al.

[11] Patent Number: 4,744,985

[45] Date of Patent: May 17, 1988

[54] NOVEL SUBSTANCES HAVING CARCINOSTATIC AND IMMUNOSTIMULATING ACTIVITY, PROCESS FOR PREPARING THE SAME AND CARCINOSTATIC AGENT CONTAINING THE SAME

[75] Inventors: Kenzo Tamai, Kanazawa; Isamu Saikawa, Toyama; Takashi Yasuda, Toyama; Shohachi Murakami, Toyama; Toyoo Maeda, Kanazawa; Hisatsugu Tsuda, Toyama; Hiroshi Sakai, Takaoka; Masatoshi Sugita, Toyama; Yoshiko Yamamoto, Namerikawa; Hisashi Minami; Takako Hori, both of Toyama, all of Japan

[73] Assignee: Toyama Chemical Co., Ltd., Tokyo, Japan

[21] Appl. No.: 180,040

[22] Filed: Aug. 21, 1980

[30] Foreign Application Priority Data

| Aug. 24, 1979 | [JP] | Japan | 54-107814 |
| Aug. 24, 1979 | [JP] | Japan | 54-107817 |
| Aug. 24, 1979 | [JP] | Japan | 54-107818 |
| Aug. 24, 1979 | [JP] | Japan | 54-107819 |
| Aug. 6, 1980 | [JP] | Japan | 55-108123 |
| Aug. 6, 1980 | [JP] | Japan | 55-108121 |
| Aug. 6, 1980 | [JP] | Japan | 55-108122 |
| Aug. 6, 1980 | [JP] | Japan | 55-108120 |

[51] Int. Cl.$^4$ .......................... A61K 35/74; C12P 1/04
[52] U.S. Cl. ..................................... 424/116; 435/170
[58] Field of Search ......................... 424/116; 435/170

[56] References Cited

PUBLICATIONS

Journal of Japan Oral Cavity Society, vol. 21, pp. 534–539.
Journal of Japan Oral Cavity Society, vol. 23, pp. 322–333.

*Primary Examiner*—Jerome D. Goldberg
*Attorney, Agent, or Firm*—Oblon, Fisher, Spivak, McClelland & Maier

[57] ABSTRACT

Novel substances having carcinostatic and immunostimulating activity, which are obtained from a culture or its supernatant fluid prepared by culturing bacteria belonging to Fusobacterium genus. Said substances are useful for the treatment of cancerous diseases lower warm-blooded animals. This disclosure concerns such substances and a process for preparing the same and a carcinostatic agent containing the same.

45 Claims, 29 Drawing Sheets

10 μ

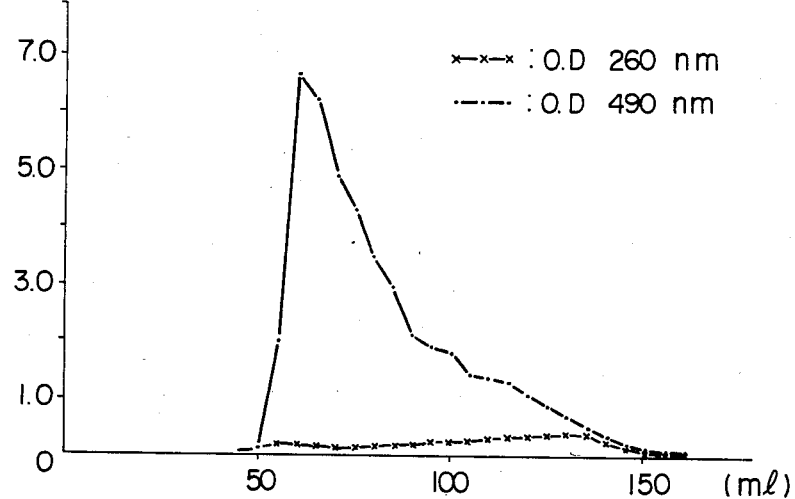
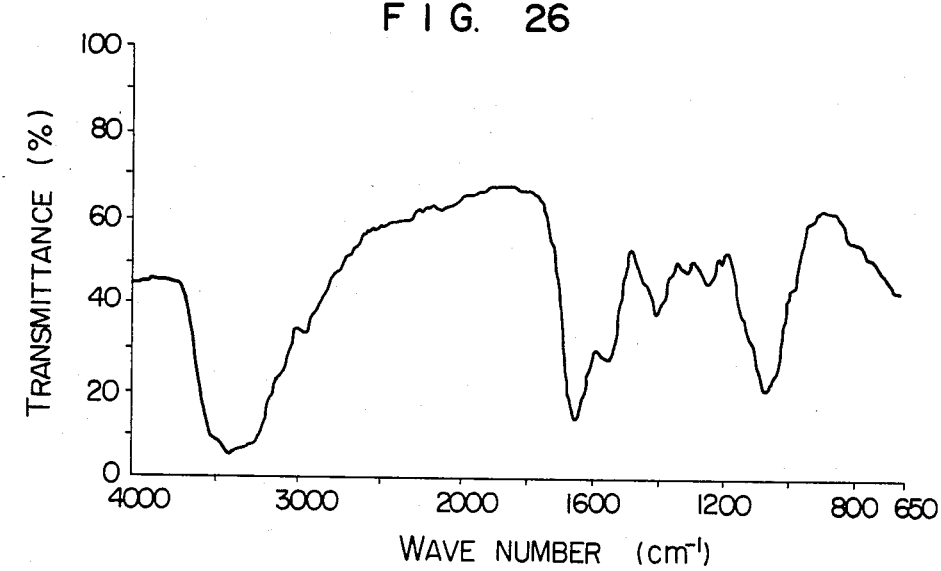

×—×—×: O.D 260 nm
—·—·—: O.D 490 nm

NOVEL SUBSTANCES HAVING CARCINOSTATIC AND IMMUNOSTIMULATING ACTIVITY, PROCESS FOR PREPARING THE SAME AND CARCINOSTATIC AGENT CONTAINING THE SAME

This invention relates to a process for producing novel substances having carcinostatic and immunostimulating activity in lower warm-blooded animals which comprises culturing under anaerobic conditions TF-substance-producing bacteria belonging to Fusobacterium genus and collecting the resulting substances from the culture or its supernatant fluid (said novel substance being hereinafter referred to as TF-substance), relates to the TF-substances obtained [hereinafter include TF-100, 110, 120, 130 (1316, 132a, 132b, 133a, 133b, 1323, 136), 140 and 150], and relates to a carcinostatic agent for lower warm-blooded animals containing the same.

There are reports on an organism and a supernatant fluid obtained by culturing bacteria belonging to Fusobacterium genus, for example, Fusobacterium K031-3B, *Fusobacterium fusifomis* W-12, *Fusobacterium girans* 1012 and *Fusobacterium nucleatum* 1010 [Dental Surgery, 23, 322–333 (1974), and 21, 534–539 (1972) (Japanese)]. However, there has not yet been made any study on the components obtained from a culture or its supernatant fluid prepared by culturing bacteria belonging to Fusobacterium genus and the pharmacological activities of the components.

The present inventors have examined the pharmacological activity of a supernatant fluid obtained by culturing bacteria belonging to Fusobacterium genus and removing the organisms from the culture to find that a specific component obtained from the supernatant fluid has a carcinostatic activity in lower warm-blooded animals; that said component has substantially no effect of inhibiting the formation of a colony of cancer cells in a colony forming assay method, and has not a carcinostatic activity by killing the cancer cells, but an indirect carcinostatic activity in lower warm-blooded animals by increasing the host mediated antitumor activity or the immunity of the lower warm-blooded animals host and utilizing the assistance of the immunity; and that said component is very low in toxicity and can be obtained also by treating the culture.

An object of this invention is to provide a process comprising culturing bacteria belonging to Fusobacterium genus under anaerobic conditions and collecting novel TF-substances having carcinostatic and immunostimulating activities for lower warm-blooded animals from the resulting culture or the supernatant fluid thereof.

Another object of this invention is to provide said TF-substances.

A further object of this invention is to provide a carcinostatic agent for lower warm-blooded animals containing said TF-substances.

Other objects and advantages of this invention will become apparent from the following description.

As the bacteria utilized in this invention, any TF-substance-producing bacteria belonging to Fusobacterium genus may be used, and, for example, *Fusobacterium nucleatum* are preferably used. Concretely, *Fusobacterium nucleatum* TF-031 (Ferm 5077; ATCC 31647) and the like are used.

The bacteriological properties of *Fusobacterium nucleatum* TF-031 are as follows:

(I) Form
  (1) Form of the cells: spindle-shaped (FIG. 1)
  (2) Polymorphism of the cells; absent
  (3) Motility: absent
  (4) Spores: absent
  (5) Gram stain: Gram-negative
  (6) Acid resistance: negative
(II) Growing conditions in a culture medium
  (1) TF-a agar plate and slant culture medium
    External form: a round shape
    Size: about 1 mm
    Protuberance: hemispherical shape
    Structure: dewdrop-like
    Surface: smooth
    Edges: smooth
    Color: milky yellowish white
    Transparency: opaque
  (2) TF-a liquid culture medium
    Degree of growth: vigorous
    Turbidity: coagulum
    Precipitate: none
    Growth of surface: none, no growth to a depth of about 5 mm
    Gas: None
(III) Physiological properties
  (1) Production of hydrogen sulfide: +
  (2) Reduction of nitrates: −
  (3) Production of butyric acid: +
  (4) Production of indole: +
  (5) Urease: −
  (6) Catalase: −
  (7) Hydrolysis of starch: −
  (8) Behavior to oxygen: anaerobic
  (9) Production of ammonia: +
  (10) Production of carbon dioxide: +
  (11) Range for growth: pH 5–8.5, temperature 30°–45° C.
  (12) Production of gas from saccharides: L-arabinose (−), D-xylose (−), D-glucose (−), D-mannose (−), D-fructose (−), D-galactose (−), malt sugar (−), sucrose (−), trehalose (−), sorbitol (−), mannitol (−), inositol (−), glycerol (−), starch (−)

The novel TF-substances of this invention are produced, for example, in the manner illustrated in FIGS. 50, 51 and 52 of the accompanying drawings.

The above-mentioned production process is illustrated as follows:

(1) Culture of bacteria

The culture of bacteria belonging to Fusobacterium genus is carried out by a usual method for culturing anaerobic bacteria. That is to say, a culture medium containing a nitrogen source such as calf brain-heart extracts, various peptones or the like; a vitamine source such as yeast extract or the like; an inorganic salt such as sodium chloride or the like; a carbon source such as glucose, lactose or the like; a reducing agent such as L-cystine, sodium sulfite, thioglycollate or the like, is adjusted to a pH of 6 to 8.5, preferably 7.2 to 8.2, and the bacteria are inoculated on the culture medium, after which steady-state culture is carried out under anaerobic conditions at 35° to 42° C., preferably 36° to 38° C., for 1 to 5 days, preferably 24 to 72 hours. In particular, it is desirable to use the culture medium described in Table 1 (hereinafter referred to as TF culture medium). However, the brain-heart-infusion which is a calf brain-heart extract is not always necessary as a nitrogen source and may be replaced by a heart infusion which is a calf heart extract, a beef extract, a fish extract, corn steep liquor, or the like. Among the various peptones, proteose peptone and phytone peptone are not always necessary, and the trypticase peptone may be replaced by polypeptone.

When agar is not used, it is desirable to carry out stirring culture.

TABLE 1

| Constituents of culture medium (g/l) | TF-a | TF-b | TF-c |
| --- | --- | --- | --- |
| Trypticase peptone | 17 | 17 | 17 |
| Phytone peptone | 3 | 3 | 1.5 |
| Proteose peptone | 10 | 5 | 5 |
| Brain-heart-infusion | 35 | 17.5 | — |
| Heart infusion | — | — | 25 |
| Yeast extract | 3 | 3 | 3 |
| Sodium chloride | 7.5 | 7.5 | 7.5 |
| Glucose | 6 | 6 | 6 |
| Lactose | 5 | 5 | 5 |
| L-Cystine | 0.25 | 0.5 | 0.5 |
| Sodium sulfite | 0.1 | 0.1 | 0.1 |
| Thioglycollate | 0.5 | 0.5 | 0.5 |
| Agar | 0 or 0.7 | 0 or 0.7 | 0 or 0.7 |

(2) Collection of a supernatant fluid from the culture (removal of the organisms)

The organisms are removed from the culture obtained above to get a supernatant fluid. For the removal of the organisms, a conventional method, for example, centrifugation and a filtration method using a filter aid, such as Hyflo Super Cel, may be used, and in particular, a centrifugation method is preferable from the viewpoint of operations, the degree of removal of the organisms, and the yield of the supernatant fluid. The organisms are preferably removed in this step, but may be removed in the subsequent step (3).

(3) Collection of substance TF-100

A hydrophilic organic solvent is added to the supernatant fluid obtained above or the culture, and the precipitate formed is collected. At this time, the supernatant fluid or the culture is preferably adjusted to pH 2 to 7. The hydrophilic organic solvent includes, for example, alcohols such as ethanol, methanol and the like, and ketones such as acetone and the like, though alcohols, particularly ethanol, brings about the best result. The hydrophilic organic solvent is suitably added so that its concentration may be 30 to 70%, particularly 50 to 70%, by volume. After the addition of the hydrophilic organic solvent, the resulting mixture is allowed to stand at a low temperature, preferably at about 5° C., for several hours to several days to complete the formation of the precipitate.

The thus formed precipitate is separated by usual procedures such as decantation, centrifugation, filtration and the like.

Subsequently, water in an amount 10 to 15 times that of the precipitate obtained above is added to the precipitate [the water may be replaced by a phosphate buffer or a sodium chloride-containing phosphate buffer when TF-120 or 130 (1316, 132a, 132b, 133a, 133b, 1323 or 136) is intended to be obtained as mentioned hereinafter] and the water-insoluble materials formed are removed by a usual method such as centrifugation, filtration or the like, after which the water-soluble fraction is collected. When the culture is used, the organisms are removed by the above-mentioned procedures. The water-soluble fraction thus obtained is dried by lyophilization or the like to obtain a substance TF-100.

The TF-100 thus obtained has properties shown in Table 2.

(4) Collection of substance TF-110

The water-soluble fraction obtained in above (3) is subjected to dialysis or ultrafiltration; or alternatively TF-100 is dissolved in water in an amount 10 to 15 times that of TF-100 and the resulting solution is subjected to dialysis or ultrafiltration. Low-molecular-weight substances such as amino acids and inorganic materials are removed by the above-mentioned treatment. The inner solution obtained by the dialysis or ultrafiltration is collected and then dried to obtain a substance TF-110.

The TF-110 thus obtained has properties shown in Table 2.

(5) Collection of substance TF-120

The water-soluble fraction obtained in above (3), or, if necessary, the inner solution by subjecting the water-soluble fraction to dialysis or ultrafiltration (the inner solution obtained in above (4)), or a solution of a powder of TF-110 in a small amount of water is treated with an ion exchanger. As the ion exchanger, a weakly basic ion exchanger or a weakly basic ion exchanger having a molecular-sievability is preferably used, and, for example, diethylaminoethyl-Sephadex A-50 (registered trademark of Pharmacia Co., Ltd.) is suitably used. A column packed with an ion exchanger is equilibrated, for example, with a phosphate buffer having a pH of about 8, after which the above-mentioned solution to be treated is passed through the column, and the eluted solution is collected and then dried by lyophilization or the like; or alternatively the same buffer as above and the solution to be treated are placed in a vessel containing an ion exchanger, and the contents are stirred and then filtered, after which the filtrate is dried; whereby a substance TF-120 having the properties described hereinafter can be obtained. TF-120 can be obtained also by desalting the eluted solution or the filtrate, for example, by dialysis using a cellophane tube or the like, by the use of Sephadex G-25 (registered trademark of Pharmacia Co., Ltd.), or by ultrafiltration, and then drying the same.

The TF-120 thus obtained has the properties shown in Table 2.

(6) Collection of substance TF-130

A column containing the adsorbed components, from which TF-120 has been removed by the treatment of above (5), is treated with a phosphate buffer, preferably a phosphate buffer having a sodium chloride concentration of 0.1 to 0.6M and a pH of about 8 (hereinafter the phosphate buffer having a sodium chloride concentration of 0.1 to 0.6M being referred to as a 0.1–0.6M sodium chloride-phosphate buffer); or alternatively the water-soluble fraction obtained in above (3) is subjected to, if necesssary, dialysis or ultrafiltration, and then to treatment with an ion exchanger by using a 0.1–0.6M sodium chloride-phosphate buffer; to obtain a fraction which is not eluted with a phosphate buffer free from sodium chloride but is eluted with a 0.1–0.6M sodium chloride-phosphate buffer.

This procedure may be carried out by either a column system or a batchwise system. The desired fraction thus obtained which is eluted with the sodium chloride-phosphate buffer is dried by lyophilization or the like to obtain a substance TF-130. The eluate containing the desired fraction which is eluted with the aforesaid sodium chloride-phosphate buffer may be desalted, for example, by dialysis using a cellophane tube, by molecular sieving by the use of Sephadex G-25, or by ultrafiltration, and then dried.

The term "TF-130" used herein refers collectively to desired eluted fractions obtained by treating the water-soluble fraction obtained in above (3) or if necessary, the inner solution component obtained by subjecting the water-soluble fraction to dialysis or ultrafiltration, with an ion exchanger, which fractions are not eluted with a phosphate buffer free from sodium chloride but eluted with a 0.1–0.6M sodium chloride-phosphate buffer. TF-130 includes concretely, for example, the following fractions.

(i) A fraction which has not been eluted with a phosphate buffer free from sodium chloride but has been eluted with a 0.6M sodium chloride-phosphate buffer in the above-mentioned ion exchanger treatment [the fraction is designated as TF-1316].

(ii) A fraction which has not been eluted with a 0.1M sodium chloride-phosphate buffer but has been eluted with a 0.2M sodium chloride-phosphate buffer in the above-mentioned ion exchanger treatment [the fraction is designated as TF-132a and b; the TF-132a is obtained by washing an ion exchanger containing the aforesaid adsorbed component with a 0.1M sodium chloride-phosphate buffer, treating the ion exhanger with a 0.2M sodium chloride-phosphate buffer, and then collecting the fraction eluted with the 0.2M sodium chloride-phosphate buffer; and the TF-132b is obtained by treating the water-soluble fraction obtained in above (3) or the inner solution component (TF-110) obtained in above (4) with an ion exchanger].

(iii) A fraction which has not been eluted with a 0.2M sodium chloride-phosphate buffer but has been eluted with a 0.3M sodium chloride-phosphate buffer in the above-mentioned ion exchanger treatment [the fraction is designated as TF-133a and b; the a and b have the same meanings as defined in the case of the TF-132a and b, respectively].

(iv) A fraction which has not been eluted with a 0.1M sodium chloride-phosphate buffer but has been eluted with a 0.3M sodium chloride-phosphate buffer in the above-mentioned ion exchanger treatment [the fraction is designated as TF-1323].

(v) A fraction which has not been eluted with a 0.5M sodium chloride-phosphate buffer but has been eluted with a 0.6M sodium chloride-phosphate buffer in the above-mentioned ion exchanger treatment [the fraction is designated as TF-136].

Since these TF-1316, 132a, 132b, 133a, 133b, 1323, and 136 have common properties in the following respects, the substances having the common properties are designated as TF-130. That is to say, the TF-130 obtained in the manner described above has the following properties:

(a) Grayish white-light brown powder.

(b) It inhibits the proliferation of mouse Ehrlich ascites tumor, Ehrlich solid tumor and Sarcoma-180 carcinoma, and has an immunostimulating activity.

(c) It is soluble in water and it is insoluble in methanol, ethanol, acetone, benzene, chloroform, ethyl acetate and diethyl ether.

(d) It has no clear melting point, begins to decompose at about 110° C., and decomposes remarkably above 200° C.

(e) Its infrared absorption spectrum obtained by a KBr tablet method has absorption bands in the vicinity of 3600–3200, 2960–2930, 1670–1550, 1440–1380, 1240, 1140–1000 and 820 $cm^{-1}$.

(f) The ultraviolet absorption spectrum of its aqueous solution shows a strong absorption at the absorption edge, and shows an absorption peak in the vicinity of 256–280 nm.

(g) It is positive in Molisch reaction, phenol-sulfuric acid reaction, anthrone-sulfuric acid reaction, indole-hydrochloric acid reaction, and Lowry-Folin's reaction, and negative in ninhydrin reaction.

(h) Elementary analysis values C: 27.5–39.8%, H: 3.2–5.7%, (i) Its saccharide content measured by a phenol-sulfuric acid method is about 19.0—about 64.0% by weight (in terms of glucose), and its protein content measured by Lowry-Folin's method is in the vicinity of 6.0–28.0% by weight (in terms of calf serum albumin).

The above-mentioned ion exchanger treatment is more specifically explained below. As the ion exchanger used in the following procedures, a weakly basic ion exchanger or a weakly basic ion exchanger having molecular sievability is preferred, and, for example, diethylaminoethyl-Sephadex A-50 used in above (5) is suitably used and the following method may be carried out by batchwise system.

(i) A 0.6M sodium chloride-phosphate buffer having, preferably, a pH of about 8 is passed through a column of an ion exchanger containing the adsorbed component which the solution to be treated has been passed through in above (5), and the fraction eluted is collected, optionally concentrated and desalted by dialysis, ultrafiltration or the like, and thereafter dried by lyophilization or the like to obtain a substance TF-1316.

The TF-1316 thus obtained has the properties shown in Table 2.

(ii)-(1) A 0.1M sodium chloride-phosphate buffer having, preferably, a pH of about 8 is passed through a column of an ion exchanger containing the adsorbed component which the solution to be treated has been passed through in above (5), to wash the column, after which a 0.2M sodium chloride-phosphate buffer having, preferably, a pH of about 8 is passed through the column, and the fraction eluted is collected, optionally concentrated and desalted by dialysis, ultrafiltration or the like, and then dried by lyophilization or the like to obtain a substance TF-132a.

The TF-132a thus obtained has the properties shown in Table 2.

(ii)-(2) Procedures for collecting the fraction which has not been eluted with a 0.1M sodium chloride-phosphate buffer but has been eluted with a 0.2M sodium chloride-phosphate buffer in the ion exchanger treatment are carried out in the following manner by the use of the water-soluble fraction obtained in above (3) or the inner solution in above (4) to obtain TF-132b. That is to say, the column packed with the ion exchanger is equilibrated with a 0.2–0.3M sodium chloride-phosphate buffer having, preferably, a pH of about 8, after which the aforesaid 0.2–0.3M sodium chloride-phosphate buffer of the water-soluble fraction obtained in above (3) or the inner solution component obtained by subjecting the water-soluble fraction to dialysis or ultrafiltration is passed through the column, and the eluted solution is collected. If necessary, the column is washed with the aforesaid 0.2–0.3M sodium chloride-phosphate buffer, and the eluted solution and the washings are combined. The ion exchanger treatment may be carried out several times. Subsequently, a solution prepared by diluting the aforesaid eluted solution with a phosphate buffer so that the sodium chloride concentration may be 0.1M is passed through a column in which the ion exchanger has been equilibrated with 0.1M sodium chloride-phosphate buffer having, preferably, a pH of about 8, and the fraction which has been eluted with the aforesaid 0.1M sodium chloride-phosphate buffer is removed, after which the aforesaid 0.2M sodium chloride-phosphate buffer is passed through the column to obtain an eluate. In the concrete example of the above-mentioned ion exchanger treatment, a fraction which has not been adsorbed on an ion exchanger equilibrated with the aforesaid 0.2M sodium chloride-phosphate buffer is collected, adsorbed on an ion exchanger equilibrated with the aforesaid 0.1M sodium chloride-phosphate buffer, washed with the aforesaid 0.1M sodium chloride-phosphate buffer, and then eluted with the aforesaid 0.2M sodium chloride-phosphate buffer to obtain an eluate. There may also be employed a method by which conversely, the fraction which has been adsorbed on an ion exchanger equilibrated with the aforesaid 0.1M sodium chloride-phosphate buffer is collected, and thereafter a procedure for separating said fraction from a fraction which has been adsorbed on an ion exchanger equilibrated with the aforesaid 0.2M sodium chloride-phosphate buffer is carried out, and a fraction which has been eluted with the aforesaid 0.2M sodium chloride-phosphate buffer is collected.

Subsequently, the eluate obtained in the manner described above is optionally concentrated and desalted by dialysis, ultrafiltration or the like, and then dried by lyophilization or the like to obtain a substance TF-132b.

The TF-132b thus obtained has the properties shown in Table 2.

(iii)-(1) The inner solution component obtained in above (4) is passed through a column of an ion exchanger equilibrated with a phosphate buffer having, preferably, a pH of about 8, and a 0.2M sodium chloride-phosphate buffer having, preferably, a pH of about 8 is passed through said column to wash the column, and then a 0.3M sodium chloride-phosphate buffer having, preferably, a pH of about 8 is passed through said column, or alternatively, the aforesaid 0.3M sodium chloride-phosphate buffer is passed through the column which has been treated in above (ii)-(1) and still has the remaining adsorbed component. The fraction eluted is collected, optionally concentrated and desalted by dialysis, ultrafiltration or the like, and then dried by lyophilization or the like to obtain a substance TF-133a.

The TF-133a thus obtained has the properties shown in Table 2.

(iii)-(2) The fraction which has not been eluted with a 0.2M sodium chloride-phosphate buffer but has been eluted with a 0.3M sodium chloride-phosphate buffer in the ion exchanger treatment is collected in the following manner which is the same as in the above-mentioned (ii)-(2) to obtain TF-133b. That is to say, the column packed with the ion exchanger is equilibrated with a 0.3M sodium chloride-phosphate buffer having, preferably, a pH of about 8, after which the aforesaid 0.3M sodium chloride-phosphate buffer of the water-soluble fraction obtained in above (3) or the inner solution component obtained by subjecting the water-soluble fraction to dialysis or ultrafiltration is passed through the column, and the eluted solution is collected. If necessary, the column is washed with the aforesaid 0.3M sodium chloride-phosphate buffer, and the eluted solution and the washings are combined. The ion exchanger treatment may be carried out several times. Subsequently, a solution prepared by diluting the aforesaid eluted solution with a phosphate buffer so that the sodium chloride concentration may be 0.2M is passed through a column in which the ion exchanger has been equilibrated with a 0.2M sodium chloride-phosphate buffer having, preferably, a pH of about 8, and the fraction which has been eluted with the aforesaid 0.2M sodium chloride-phosphate buffer is removed, after which the aforesaid 0.3M sodium chloride-phosphate buffer is passed through the column to obtain an eluate. In the concrete example of the above-mentioned ion exchanger treatment, a fraction which has not been adsorbed on an ion exchanger equilibrated with the aforesaid 0.3M sodium chloride-phosphate buffer is collected, adsorbed on an ion exchanger equilibrated with the aforesaid 0.2M sodium chloride-phosphate buffer, washed with the aforesaid 0.2M sodium chloride-phosphate buffer, and then eluted with the aforesaid 0.3M sodium chloride-phosphate buffer to obtain an eluate. There may also be employed a method by which conversely, a fraction which has been adsorbed on an ion exchanger equilibrated with the aforesaid 0.2M sodium chloride-phosphate buffer is collected, and thereafter a procedure for separating said fraction from a fraction which has been adsorbed on an ion exchanger equilibrated with the aforesaid 0.3M sodium chloride-phosphate buffer is carried out, and a fraction which has been eluted with the aforesaid 0.3M sodium chloride-phosphate buffer is collected.

Subsequently, the eluate obtained in the manner described above is optionally concentrated and desalted by dialysis, ultrafiltration or the like, and then dried by lyophilization or the like to obtain the desired substance TF-133b.

The TF-133b thus obtained has the properties shown in Table 2.

(iv) The water-soluble fraction obtained in above (3) or the inner solution component obtained in above (4) is formed into a 0.3M sodium chloride-phosphate buffer having, preferably, a pH of about 8, and the buffer obtained is passed through an ion exchanger column which has previously been equilibrated with a 0.3M sodium chloride-phosphate buffer having, preferably, a pH of about 8. The eluted solution is adjusted by the addition of a phosphate buffer so that the sodium chloride concentration may be 0.1M, and then passed through an ion exchanger column which has previously been equilibrated with a 0.1M sodium chloride-phosphate buffer having, preferably, a pH of about 8, and subsequently, the aforesaid 0.3M sodium chloride-phosphate buffer is passed through said column, after which the fraction eluted is collected, optionally concentrated and desalted by dialysis, ultrafiltration or the like, and then dried by lyophilization or the like to obtain a substance TF-1323.

The TF-1323 thus obtained has the properties shown in Table 2.

(v) The inner solution component obtained in above (4) is passed through a column of an ion exchanger equilibrated with a phosphate buffer having, preferably, a pH of about 8, and a 0.5M sodium chloride-phosphate buffer having, preferably, a pH of about 8 is passed through said column to wash the column, and then a 0.6M sodium chloride-phosphate buffer having, preferably, a pH of about 8 is passed through said column, or alternatively, the aforesaid 0.5M sodium chloride-phosphate buffer is passed through the column which has been treated in above (ii)-(2) and still has the remaining adsorbed component, after which the aforesaid 0.6M sodium chloride-phosphate buffer is passed through said column. The fraction eluted is collected, optionally concentrated and desalted by dialysis, ultrafiltration or the like, and then dried by lyophilization or the like to obtain a substance TF-136.

The TF-136 thus obtained has the properties shown in Table 2.

(7) Collection of substance TF-140

Barium ions are added to the culture or its supernatant fluid obtained in above (1) or (2) or to the water-soluble fraction obtained in above (3) or to the solution obtained by dissolving TF-100 in water, to form a barium salt, after which the precipitate is collected, and then subjected to a procedure for removing the barium, and the water-soluble fraction is collected, and then subjected to dialysis or ultrafiltration to obtain TF-140. Specifically explaining, an aqueous barium hydroxide solution, preferably a 0.1–0.5M aqueous barium hydroxide solution is added to the culture or its supernatant fluid obtained in above (1) or (2) or to the water-soluble fraction obtained in above (3) or to an aqueous solution obtained by dissolving TF-100 in water in an amount about 10–15 times that of TF-100, and the pH of the resulting mixture is preferably adjusted to 10 to 13 to form a barium salt. A precipitate is deposited by the addition of a barium hydroxide solution, and the added amount of the barium ions is preferably adjusted so that the concentration of the total barium ions to the final volume of the mixture may be 0.005 to 0.1M. The mixture thus obtained is filtered, and a procedure for separating the barium from the barium salt obtained is carried out. The barium is removed preferably by adding the barium salt to sodium sulfate, preferably a 5–15% aqueous sodium sulfate solution, stirring the resulting mixture, and then carrying out a filtration procedure to obtain a solution. The precipitate which has been separated and removed is washed with an aqueous sodium sulfate solution again, and the washings are combined with the above-mentioned solution. The solution thus obtained is subjected to dialysis, ultrafiltration or the like, to remove the excess of sodium sulfate or lower molecular substances, and the resulting solution is then dried by lyophilization or the like to obtain a substance TF-140.

The thus obtained TF-140 has the properties shown in Table 2.

(8) Collection of substance TF-150

The water-soluble fraction obtained in above (3) or the inner solution obtained in above (4) is treated with a quaternary ammonium salt, and the precipitate formed is collected, and then subjected to a dissociation procedure using a solution containing sodium chloride, after which a hydrophilic organic solvent is added to the soluble fraction, and the thus formed precipitate is collected and then dried to obtain TF-150. As a quaternary ammonium salt which can be used here, in usual, may be any complex with a polysaccharide, and particularly preferable examples thereof include cetyl-pyridinium chloride, cetyl-trimethylammonium bromide, etc. The treatment with a quaternary ammonium salt is preferably carried out in the presence of a buffer such as a borate buffer or the like. The concrete description of the above-mentioned treatment with a quaternary ammonium salt and the dissociation procedure using a solution containing sodium chloride is as follows. For example, an aqueous solution of a quaternary ammonium salt is added dropwise to the water-soluble fraction obtained in above (3) or the inner solution obtained in above (4) while keeping the pH weakly basic, and the resulting mixture is stirred at 0° to 50° C. for 10 minutes to several hours, after which the precipitate deposited is collected. The precipitate is washed several times with a buffer, preferably a 0.1% borate buffer, containing 0.1M of sodium chloride and a slight amount of a quaternary ammonium salt, and then dissociated with a buffer, preferably a 0.1% borate buffer, containing 0.5M of sodium chloride and a slight amount of a quaternary ammonium salt to obtain a soluble fraction, and then the soluble fraction is preferably adjusted to pH 2 to 6. Subsequently, a hydrophilic organic solvent, preferably an alcohol, is added to the soluble fraction so that its concentration may finally be 50 to 90%, preferably 70 to 90% by volume, and the mixture thus obtained is allowed to stand at 0° to 30° C. for several hours to 90 hours, after which the precipitate deposited is collected to obtain a substance TF-150.

The TF-150 thus obtained has the properties shown in Table 2.

TABLE 2

| Fraction | Appearance | Pharmacological action | Solubility | Decomposing point | Infrared absorption spectra (KBr method) (cm$^{-1}$) | C (%) | H (%) | N (%) |
|---|---|---|---|---|---|---|---|---|
| | | | | | | \multicolumn{3}{c}{Elementary analysis values} |
| TF-100 | Grayish white-light brown powder | This fraction inhibited the proliferation of Ehrlich ascites tumor and Ehrlich solid tumor of mouse and had an immunostimulating activity. | Soluble in water, and insoluble in methanol, ethanol, acetone, benzene, chloroform, ethyl acetate and diethyl ether. | This fraction began to decompose at about 110° C. and remarkably decomposed above 200° C. | The spectrum has absorption bands in the vicinity of 3600–3200, 2960–2930, 1670–1640, 1550, 1440–1380, 1240, 1140–1000, and 820 cm$^{-1}$. | 30.6–35.7 | 4.2–5.2 | 4.2–5.2 |
| TF-110 | Grayish white-light brown powder | This fraction inhibited the proliferation of Ehrlich asites tumor of mouse and had an immunostimulating activity. | Soluble in water, and insoluble in methanol, ethanol, acetone, benzene, chloroform, ethyl acetate and diethyl ether. | This fraction began to decompose at about 110° C. and remarkably decomposed above 200° C. | The spectrum has absorption bands in the vicinity of 3600–3200, 2960–2930, 1670–1640, 1550, 1440–1380, 1240, 1140–1000, and 820 cm$^{-1}$. | 35.9–41.0 | 4.5–5.2 | 4.2–5.2 |
| TF-120 | Grayish white-light brown powder | This fraction inhibited the proliferation of Ehrlich asites tumor of mouse and had an immunostimulating activity. | Soluble in water, and insoluble in methanol, ethanol, acetone, benzene, chloroform, ethyl acetate and diethyl ether. | This fraction began to decompose at about 110° C. and remarkably decomposed above 200° C. | The spectrum has absorption bands in the vicinity of 3600–3200, 2960–2930, 1670–1640, 1550, 1380–1360, 1140–1000, and 820 cm$^{-1}$. | 35.1–40.2 | 4.5–5.5 | 2.0–3.1 |
| TF-1316 | Grayish white-light brown powder | This fraction inhibited the proliferation of Ehrlich ascites tumor, Ehrlich solid tumor and Sarcoma-180 carcinoma of mouse and had an immunostimulating activity. | Soluble in water, and insoluble in methanol, ethanol, acetone, benzene, chloroform, ethyl acetate and diethyl ether. | This fraction began to decompose at about 110° C. and remarkably decomposed above 200° C. | The spectrum has absorption bands in the vicinity of 3600–3200, 2960–2930, 1670–1640, 1550, 1440–1380, 1240, 1140–1000, and 820 cm$^{-1}$. | 30.0–34.0 | 3.8–4.4 | 4.9–5.7 |
| TF-132a | Grayish white-light brown powder | This fraction inhibited the proliferation of Ehrlich ascites tumor, Ehrlich solid tumor and Sarcoma-180 carcinoma of mouse and had an immunostimulating activity. | Soluble in water, and insoluble in methanol, ethanol, acetone, benzene, chloroform, ethyl acetate and diethyl ether. | This fraction began to decompose at about 110° C. and remarkably decomposed above 200° C. | The spectrum has absorption bands in the vicinity of 3600–3200, 2960–2930, 1670–1640, 1550, 1440–1380, 1240, 1140–1000, and 820 cm$^{-1}$. | 34.8–39.8 | 4.5–5.7 | 2.8–3.6 |
| TF-132b | Grayish white-light brown powder | This fraction inhibited the proliferation of Ehrlich ascites tumor, Ehrlich solid tumor and Sarcoma-180 carcinoma of mouse and had an immunostimulating activity. | Soluble in water, and insoluble in methanol, ethanol, acetone, benzene, chloroform, ethyl acetate and diethyl ether. | This fraction began to decompose at about 110° C. and remarkably decomposed above 200° C. | The spectrum has absorption bands in the vicinity of 3600–3200, 2960–2930, 1670–1640, 1550, 1440–1380, 1240, 1140–1000, and 820 cm$^{-1}$. | 35.3–39.5 | 4.5–5.6 | 2.8–5.4 |
| TF-133a | Grayish white-light brown powder | This fraction inhibited the proliferation of Ehrlich ascites tumor, Ehrlich solid tumor and Sarcoma-180 carcinoma of mouse and had an immunostimulating activity. | Soluble in water, and insoluble in methanol, ethanol, acetone, benzene, chloroform, ethyl acetate and diethyl ether. | This fraction began to decompose at about 110° C. and remarkably decomposed above 200° C. | The spectrum has absorption bands in the vicinity of 3600–3200, 2960–2930, 1670–1640, 1550, 1440–1380, 1240, 1140–1000, and 820 cm$^{-1}$. | 28.0–36.6 | 3.5–5.1 | 4.5–6.3 |
| TF-133b | Grayish white-light brown powder | This fraction inhibited the proliferation of Ehrlich ascites tumor, Ehrlich solid tumor and Sarcoma-180 carcinoma of mouse and had an immunostimulating activity. | Soluble in water, and insoluble in methanol, ethanol, acetone, benzene, chloroform, ethyl acetate and diethyl ether. | This fraction began to decompose at about 110° C. and remarkably decomposed above 200° C. | The spectrum has absorption bands in the vicinity of 3600–3200, 2960–2930, 1670–1640, 1550, 1440–1380, 1240, 1140–1000, and 820 cm$^{-1}$. | 31.1–38.5 | 3.9–5.2 | 3.4–4.7 |
| TF-1323 | Grayish white-light brown powder | This fraction inhibited the proliferation of Ehrlich ascites tumor, Ehrlich solid tumor and Sarcoma-180 carcinoma of mouse and had an immunostimulating activity. | Soluble in water, and insoluble in methanol, ethanol, acetone, benzene, chloroform, ethyl acetate and diethyl ether. | This fraction began to decompose at about 110° C. and remarkably decomposed above 200° C. | The spectrum has absorption bands in the vicinity of 3600–3200, 2960–2930, 1670–1640, 1550, 1440–1380, 1240, 1140–1000, and 820 cm$^{-1}$. | 29.9–39.4 | 3.9–5.6 | 2.8–5.4 |
| TF-136 | Grayish white-light brown | This fraction inhibited the proliferation of Ehrlich ascites tumor, Ehrlich solid tumor and | Soluble in water, and insoluble in methanol, ethanol, acetone, benzene, chloroform, | This fraction began to decompose at about 110° C. and remarkably decomposed above 200° C. | The spectrum has absorption bands in the vicinity of 3600–3200, 2960–2930, 1670–1640, 1550, 1440–1380, 1240, | 27.5–32.6 | 3.2–4.0 | 5.0–6.1 |

TABLE 2-continued

| | | Properties | | | |
|---|---|---|---|---|---|
| TF-140 | powder | Sarcoma-180 carcinoma of mouse and had an immunostimulating activity. | | | |
| | Grayish white-light brown powder | This fraction inhibited the proliferation of Ehrlich ascites tumor of mouse and had an immunostimulating activity. | This fraction began to decompose at about 210° C. and remarkably decomposed about 280° C. | The spectrum has absorption bands in the vicinity of 3600-3200, 2960-2930, 1670-1640, 1550, 1440-1380, 1240, 1140-1000, and 820 cm$^{-1}$. | 22.0-28.0 | 3.0-3.5 | 5.0-6.5 |
| TF-150 | Grayish white-light brown powder | This fraction inhibited the proliferation of Ehrlich ascites tumor of mouse and had an immunostimulating activity. | Soluble in water, and insoluble in methanol, ethanol, acetone, benzene, chloroform, ethyl acetate and diethyl ether. | This fraction began to decompose at about 110° C. and remarkably decomposed above 200° C. | The spectrum has absorption bands in the vicinity of 3600-3200, 2960-2930, 1670-1640, 1550, 1440-1380, 1240, 1140-1000, and 820 cm$^{-1}$. | 31.0-34.0 | 4.0-4.4 | 2.8-3.2 |

| Fraction | Ultraviolet absorption spectra (aqueous solution) λ$_{max}$(nm) | Sephadex G-50* | | Sephadex G-200** | | | High performance liquid chromatogram*** | |
|---|---|---|---|---|---|---|---|---|
| | | 260 nm | Anthrone-H$_2$SO$_4$ method 620 nm | 260 nm | Phenol-H$_2$SO$_4$ method 490 nm | Anthrone-H$_2$SO$_4$ method 620 nm | 220 nm | 260 nm |
| TF-100 | At the absorption edge and in the vicinity of 256-260 nm | In the vicinity of v.v.-400, 430-530, 700-800, and 840-870 ml | In the vicinity of v.v.-390, and 410-430 ml | | | | In the vicinity of the solvent front, 38-60, and 65 min. | In the vicinity of the solvent front, 38-60, and 65 min. |
| TF-110 | At the absorption edge and in the vicinity of 256-260 nm | | | In the vicinity of v.v.-380, 600-920 ml | In the vicinity of v.v.-380, 410-520, and 630-760 ml | In the vicinity of v.v.-380, 420-520, and 620-760 ml | In the vicinity of the solvent front, 38-60, and 65 min. | In the vicinity of the solvent front, 38-60 and 65 min. |
| TF-120 | At the absorption edge and in the vicinity of 268-272 nm | | | In the vicinity of v.v.-325, and 775-875 ml | In the vicinity of v.v.-360, 360-480, and 510-760 ml | In the vicinity of v.v.-380, 420-520, and 620-760 ml | In the vicinity of the solvent front and 38-60 min. | In the vicinity of the solvent front and 38-60 min. |
| TF-1316 | At the absorption edge and in the vicinity of 256-260 nm | | | In the vicinity of v.v.-160 ml | In the vicinity of v.v.-160 ml | | In the vicinity of the solvent front and 40-60 min. | In the vicinity of the solvent front and 40-60 min. |
| TF-132a | At the absorption edge and in the vicinity of 258-262 nm | | | In the vicinity of v.v.-340, 600-700, and 720-880 ml | In the vicinity of v.v.-340, 340-580, and 720-900 ml | In the vicinity of v.v.-340, and 340-580 ml | In the vicinity of the solvent front, 30, 38-60 and 65 min. | In the vicinity of the solvent front, 62, and 65 min. |
| TF-132b | At the absorption end, a shoulder in the vicinity of 270-280 nm | | | In the vicinity of v.v.-150 ml | In the vicinity of v.v.-150 ml | | In the vicinity of the solvent front, 36-37 and 48-50 min. | In the vicinity of the solvent front, 32-39, and 45-52 min. |
| TF-133a | At the absorption edge and in the vicinity of 265-280 nm | | | In the vicinity of v.v.-300, and 630-940 ml | In the vicinity of v.v.-420 ml | In the vicinity of v.v.-420 ml | In the vicinity of the solvent front, 38, and 50 min. | In the vicinity of the solvent front, 50-60 and 62 min. |
| TF-133b | At the absorption end, a shoulder in the vicinity of 265-280 nm | | | In the vicinity of v.v.-170 ml | In the vicinity of v.v.-150 ml | | In the vicinity of the solvent front, 49-50 min. | In the vicinity of the solvent front, 38-39, and 52 min. |
| TF-1323 | At the absorption edge, a shoulder in the vicinity of 265-280 nm | | | In the vicinity of v.v.-160 ml | In the vicinity of v.v.-150 ml | | In the vicinity of the solvent front, 36, and 48-50 min. | In the vicinity of the solvent front, 36, and 50 min. |
| TF-136 | At the absorption edge and in the vicinity of 256-260 nm | | | In the vicinity of 540-930 ml | Slight absorption band | Slight absorption band | In the vicinity of the solvent front, 28-40, and 42-60 min. | In the vicinity of the solvent front, 42-60 min. |
| TF-140 | At the absorption edge and in the vicinity of 255-260 nm | | | In the vicinity of v.v.-300, 500-900, and 900-1000 ml | In the vicinity of v.v.-500, 650-850, and 850-1000 ml | | In the vicinity of the solvent front, and 40-60 min. | In the vicinity of the solvent front, 40-60 min. |
| TF-150 | At the absorption edge | | | In the vicinity of | | | In the vicinity of the solvent | In the vicinity of the solvent |

TABLE 2-continued

| | | | | | | | | |
|---|---|---|---|---|---|---|---|---|
| | and in the vicinity of 255–260 nm | v.v.–100, and 100–160 ml | v.v.–150 ml | | | | front, 32, and 48–50 min. | front, 32, and 48–50 min. |
| | | | Color reaction | | | Properties | | |
| Fraction | Ninhydrin reaction | Molisch reaction | Phenol-H$_2$SO$_4$ reaction | Anthrone-H$_2$SO$_4$ reaction | Indole-HCl reaction | Lowry-Folin reaction | Saccharide content in terms of glucose, measured by Phenol-H$_2$SO$_4$ method (%) | Protein content in terms of calf serum alubumin, measured by Lowry-Folin's method (%) |
| TF-100 | + | + | + | + | + | + | ca. 40.0–ca. 46.0 | ca. 20.0–ca. 23.0 |
| TF-110 | − | + | + | + | + | + | ca. 30.0–ca. 69.0 | ca. 18.0–ca. 22.0 |
| TF-120 | − | + | + | + | + | + | ca. 56.0–ca. 73.0 | ca. 9.0–ca. 13.0 |
| TF-1316 | − | + | + | + | + | + | ca. 35.0–ca. 50.0 | ca. 10.0–ca. 23.0 |
| TF-132a | − | + | + | + | + | + | ca. 55.0–ca. 64.0 | ca. 18.0–ca. 28.0 |
| TF-132b | − | + | + | + | + | + | ca. 23.6–ca. 45.5 | ca. 15.5–ca. 28.0 |
| TF-133a | − | + | + | + | + | + | ca. 26.0–ca. 35.0 | ca. 22.0–ca. 28.0 |
| TF-133b | − | + | + | + | + | + | ca. 19.0–ca. 24.5 | ca. 12.9–ca. 22.9 |
| TF-1323 | − | + | + | + | + | + | ca. 19.0–ca. 25.0 | ca. 11.0–ca. 17.0 |
| TF-136 | − | + | + | + | + | + | ca. 19.0–ca. 30.0 | ca. 6.0–ca. 12.0 |
| TF-140 | − | + | + | + | + | + | ca. 5.0–ca. 15.0 | ca. 23.0–ca. 32.0 |
| TF-150 | − | + | + | + | + | + | ca. 40.0–ca. 55.0 | ca. 7.0–ca. 14.0 |

In Table 2, for the Sephadex G-50 marked "*", a 50 mmφ×600 mm column and distilled water as an eluent were used; for the Sephadex G-200 (registered trademark of Pharmacia Co., Ltd.) marked "", there were used a 44 mmφ×500 mm column for TF-110, 120, 132a, 133a, 136, and 140, and a 21 mmφ×400 mm column for TF-1316, 132b, 133b, 1323, and 150, and as an eluent, a 0.1M phosphate buffer having a pH of 7 was used for all of them and in obtaining the high performance liquid chromatogram marked "*", a 7.9 mmφ×600 mm×2 column of TSK-GEL G 3000SW (trade name of Toyo Soda Co., Ltd.), was used and the elution was carried out at room temperature at a flow rate of 0.8 ml/min. by using 0.1M phosphate buffer having a pH of 7 as an eluent.

The pharmacological activities of the present substances for lower warm-blooded animals TF-100, TF-110, TF-120, TF-1316, TF-132a, TF-132b, TF-133a, TF-133b, TF-1323, TF-140 and TF-150 are as follows:

(I) Effect of TF-substances on cell viability (Colony-forming Assay)

Based on the method of Kim. J. H. et al. [Cancer Res. 25, 698 (1965)], HeLa S-3 cells were cultured in Eagle's MEM supplemented with 10% calf serum for 3 to 5 days at 37° C., $CO_2$-incubator, after which the culture was removed, and a PBS(−) solution (an aqueous solution containing 8.0 g/l of sodium chloride, 0.2 g/l of potassium chloride, 1.15 g/l of sodium phosphate, monobasic and 0.2 g/l of potassium phosphate, dibasic) containing 0.01% by weight of ethylenediaminetetraacetic acid and 0.1% by weight of trypsin was added to the glass adherent cells. The cells were stripped from the glass surface of the culture bottle, and were dissociated to single cells by pipetting, and then cell numbers were counted with the microscopy. The cells suspension was diluted with Eagle's MEM supplemented with 20% calf serum so that it might contain 200 cells per ml. After 1 ml of the cell suspension was inoculated to Petri dishes and was cultured in a $CO_2$ incubator at 37° C. for 24 hours, the supernatant fluid obtained in Example 1 (I), which appears hereinafter, was added to the cell suspension so that the concentration became 1/16 to 1/28. And, to each of 1-ml portions of the cell suspension cultured at 37° C. for 24 hours, each of the test substances was added, and the HeLa cells in each case were cultured for 7 days. After the culture, the culture medium was removed, after which the culture dishes were washed with Hank's solution, and the cells were fixed with 70% by weight ethanol, and then washed with 100% by weight ethanol. After the ethanol was removed, the cells were stained with a Giemsa staining solution, after which the colonies were counted, and the cell viability was calculated.

The results are as shown in Tables 3 and 4. The cell viability in the tables were calculated from the following equation. The cell viability of each test substance is represented as an average value in 5 replicates.

$$\text{Cell viability} = \frac{\text{Number of colonies in the case of a treated group}}{\text{Number of colonies in the case of an untreated group}} \times 100$$

TABLE 3

Effect of the supernatant fluid on cell viability

| Dilution (ml/ml) | Cell viability (%) | | |
|---|---|---|---|
| | 48 hours | 72 hours | 96 hours |
| 1/128 | 79.6 | 66.4 | 80.4 |
| 1/64 | 30.0 | 7.9 | 5.8 |
| 1/32 | 0 | 0 | 0 |
| 1/16 | 0 | 0 | 0 |
| Control | 100 | 100 | 100 |

TABLE 4

Effect of the TF-substances on cell viability

| Substance | Concentration (μg/ml) | Cell viability (%) |
|---|---|---|
| TF-100 | 10 | 99.4 |
| | 50 | 97.4 |
| | 100 | 95.9 |
| TF-110 | 10 | 94.5 |
| | 50 | 88.9 |
| | 100 | 87.3 |
| TF-120 | 10 | 98.8 |
| | 50 | 91.2 |
| | 100 | 83.3 |
| TF-132a | 10 | 96.7 |
| | 50 | 97.4 |
| | 100 | 95.9 |
| TF-133a | 10 | 96.9 |
| | 50 | 95.4 |
| | 100 | 88.8 |
| TF-136 | 10 | 95.9 |
| | 50 | 96.4 |
| | 100 | 95.4 |
| TF-140 | 10 | 98.5 |
| | 50 | 98.6 |
| | 100 | 98.6 |
| | 200 | 96.8 |
| | 500 | 93.4 |

As is evident from this experiment, the TF-substances of this invention are very low in cytoxidal effect on HeLa cells, as compared with the supernatant fluid.

(II) Immunostimulating activity

Four ICR strain mice for each group were used. Each of the test substances was dissolved in 0.2 ml of a physiological salt solution, and then intraperitoneally administered to the mice. Twenty-four hours after the administration, 0.2 ml of a carbon suspension prepared by mixing 1 ml of Perikan Drawing Ink 17 Black (manufactured by Günther-Wagner Co., Ltd.) and 2 ml of a physiological salt solution containing 3% by weight of gelatin was intravenously injected into the mouse tail and 1, 5, 10 and 15 minutes after the injection, 0.02 ml of the blood was collected from the orbit by using a hematocrit capillary coated with heparin, and immediately diluted and hemolyzed with 1.6 ml of a 0.1% by weight aqueous sodium carbonate solution. This suspension was subjected to colorimetry at 675 nm, and the phagocytotic index, namely K value, was determined from the equation of Halpern et al.

To the mice in the control group was administered 0.2 ml of a physiological salt solution.

$$K = \frac{\log C_0 - \log C}{t - t_0}$$

wherein $C_0$=carbon powder content in blood at the time of $t_0$, and $C$=carbon powder content in blood at the time of $t$.

The results are as shown in Tables 5 to 7.

TABLE 5

| Substance | Dosage (mg/Kg) | Average of K values |
|---|---|---|
| TF-100 | 10 | 0.0851 ± 0.0145 |
|  | 50 | 0.0605 ± 0.0302 |
| TF-110 | 5 | 0.0901 ± 0.0213 |
|  | 20 | 0.1025 ± 0.0025 |
| TF-120 | 5 | 0.0718 ± 0.0152 |
|  | 20 | 0.0559 ± 0.0197 |
| TF-1316 | 5 | 0.0832 ± 0.0193 |
|  | 20 | 0.1001 ± 0.0246 |
| TF-132a | 5 | 0.1102 ± 0.0203 |
|  | 20 | 0.0809 ± 0.0296 |
| TF-133a | 5 | 0.0851 ± 0.0057 |
|  | 20 | 0.0769 ± 0.0174 |
| TF-136 | 5 | 0.0959 ± 0.0087 |
|  | 20 | 0.1027 ± 0.0154 |
| Control | — | 0.0300 ± 0.0024 |

TABLE 6

| Substance | Dosage (mg/Kg) | Average of K values |
|---|---|---|
| TF-132b | 5 | 0.1190 ± 0.0051 |
|  | 20 | 0.1073 ± 0.0031 |
| TF-133b | 5 | 0.0550 ± 0.0020 |
|  | 20 | 0.1099 ± 0.0075 |
| TF-150 | 5 | 0.1399 ± 0.0011 |
|  | 20 | 0.0577 ± 0.0098 |
| TF-1323 | 5 | 0.1400 ± 0.0075 |
|  | 20 | 0.0685 ± 0.0126 |
| Control | — | 0.0286 ± 0.0035 |

TABLE 7

| Substance | Dosage (mg/Kg) | Average of K values |
|---|---|---|
| TF-140 | 1 | 0.0891 ± 0.0156 |
|  | 5 | 0.0946 ± 0.0139 |
|  | 20 | 0.0815 ± 0.0200 |
| Control | — | 0.0379 ± 0.0048 |

As is evident from Tables 5 to 7, the groups to which each of the TF-substances of this invention was administered showed the activation of reticuloendothelial macrophages as compared with the control group, and the cellular immunity of the normal mice was increased.

(III) Carcinostatic activity (a) Antitumor activity against Ehrlich ascites tumor Ehrlich ascites tumor cells were intraperitoneally inoculated into ICR strain mice (female, 6 weeks old) in an amount of $1 \times 10^5$ cells per mouse. Subsequently, each of the test substances was dissolved in 0.2 ml of a physiological salt solution, and then intraperitoneally administered to the mice once a day repeatedly for 7 days from the first day after the inoculation of the tumor cells, or once a day on the first day and from the third day to the seventh day for six days in total. In the case of the test substances in Table 9, each of them was administered to the mice once a day on the first day and from the third day to seventh day for six days in total after the inoculation of the tumor cells. To the control group, 0.2 ml of a physiological salt solution was administered in the same manner as above.

The results are as shown in Tables 8 and 9.

$$T/C = \frac{\text{Number of survival days of the mice in a group to which the substance was administered}}{\text{Number of survival days of the mice in the control group}} \times 100\ (\%)$$

TABLE 8

| Substance | Dosage (mg/kg × the number of administrations) | Average survival days (day) | T/C (%) | *Number of survivors/Number of tested mice | |
|---|---|---|---|---|---|
| TF-100 | 70 × 7 | >30.1 ± 8.1 | >162 | 13/20 | *1 |
|  | — | 18.6 ± 1.9 | 100 | 0/20 |  |
| TF-110 | 10 × 6 | >24.0 ± 10.0 | >142 | 2/5 | *1 |
|  | 50 × 6 | >32.5 ± 2.9 | >193 | 3/5 |  |
|  | — | 16.8 ± 1.3 | 100 | 0/5 |  |
| TF-120 | 10 × 5 | >27.5 ± 9.3 | >154 | 2/4 | *1 |
|  | 50 × 6 | >27.3 ± 9.2 | >153 | 2/4 |  |
|  | — | 17.8 ± 2.2 | 100 | 0/4 |  |
| TF-132a | 1 × 6 | >20.8 ± 7.8 | >121 | 1/6 | *1 |
|  | 5 × 6 | 18.3 ± 4.2 | 106 | 0/6 |  |
|  | 10 × 6 | >23.3 ± 8.8 | >135 | 1/6 |  |
|  | — | 17.2 ± 2.2 | 100 | 0/6 |  |
| TF-133a | 1 × 6 | >28.2 ± 7.8 | >164 | 3/6 | *1 |
|  | 5 × 6 | >28.8 ± 9.6 | >167 | 4/6 |  |
|  | 10 × 6 | >29.7 ± 6.8 | >172 | 3/6 |  |
|  | — | 17.2 ± 2.2 | 100 | 0/6 |  |
| TF-136 | 1 × 6 | >23.0 ± 6.5 | >134 | 1/6 | *1 |
|  | 5 × 6 | >30.3 ± 5.6 | >176 | 3/6 |  |
|  | 10 × 6 | >25.0 ± 8.2 | >145 | 1/6 |  |
|  | — | 17.2 ± 2.2 | 100 | 0/6 |  |
| TF-1316 | 25 × 6 | 22.0 ± 5.2 | 127 | 0/4 | *1 |
|  | 100 × 6 | >32.8 ± 11.2 | >187 | 2/4 |  |
|  | — | 17.5 ± 1.9 | 100 | 0/4 |  |
| TF-132b | 5 × 6 | >35.0 ± 9.8 | >186 | 2/5 | *2 |
|  | 10 × 6 | >40.0 ± 4.5 | >213 | 4/5 |  |
|  | — | 18.8 ± 2.2 | 100 | 0/5 |  |
| TF-133b | 1 × 6 | >24.0 ± 11.9 | >128 | 1/5 | *2 |
|  | 5 × 6 | >33.2 ± 12.1 | >176 | 3/5 |  |
|  | 10 × 6 | >34.8 ± 10.5 | >185 | 2/5 |  |
|  | — | 18.8 ± 2.2 | 100 | 0/5 |  |
| TF-1323 | 1 × 7 | >29.4 ± 10.8 | >173 | 4/10 | *2 |
|  | 5 × 7 | >38.4 ± 3.5 | >226 | 8/10 |  |
|  | 10 × 7 | >34.0 ± 11.0 | >200 | 6/10 |  |

TABLE 8-continued

| Substance | Dosage (mg/kg × the number of administrations) | Average survival days (day) | T/C (%) | *Number of survivors/ Number of tested mice |
|---|---|---|---|---|
| | — | 17.0 ± 1.1 | 100 | 0/10 |

Note: *All the survivors had no ascites and were completely cured.
*1 The judgement on the 35th day after the transplantation of the tumor cells.
*2 The judgement on the 40th day after the transplantation of the tumor cells.

TABLE 9

| Substance | Dosage (mg/kg × the number of administrations) | Average survival days (day) | T/C (%) | *Number of survivors/ Number of tested mice (on 35th day) |
|---|---|---|---|---|
| TF-140 | 0.5 × 6 | >23.6 ± 9.3 | >148 | 2/5 |
| | 1 × 6 | >27.0 ± 7.5 | >170 | 4/10 |
| | 5 × 6 | >31.5 ± 5.7 | >198 | 9/15 |
| | 10 × 6 | >28.4 ± 14.8 | >178 | 4/5 |
| | — | 15.9 ± 3.4 | 100 | 0/15 |
| TF-150 | 5 × 6 | >30.6 ± 5.4 | >159 | 3/5 |
| | 10 × 6 | >32.0 ± 4.7 | >168 | 3/5 |
| | 50 × 6 | >35.0 ± 0 | >182 | 5/5 |
| | — | 19.2 ± 1.5 | 100 | 0/5 |

Note: *All the survivors had no ascites and were completely cured.

As is evident from Tables 8 and 9, the group to which each of the TF substances of this invention was administered underwent the life-prolonging effect, as compared with the control group.

(b) Antitumor activity against Ehrlich solid tumor (1) Ehrlich tumor cells were subcutaneously transplanted at the armpit to ICR strain mice (female, 6 weeks old) in an amount of 4×10⁶ cells per mouse. Subsequently, each of the test substances was administered to the mice once a day repeatedly for 7 days from the first day after the transplantation of the tumor cells, or once a day on the first day and from the third day to the seventh day for 6 days in total. To the control group was administered 0.2 ml of a physiological salt solution in the same manner as described above. The weights of the tumors were determined on the 11th or 14th day after the transplantation of the tumor cells. The weights of the tumors were determined by measuring the major diameter (a) mm and the minor diameter (b) mm by means of calipers, and calculating from the following equation:

$$\text{Weight of the tumor} = \frac{a \times b^2}{2} \text{ (mg)}$$

The results are as shown in Table 10.

TABLE 10

| Substance | Administration route | Dosage (mg/kg × the number of administrations) | Average tumor weight (g) | T/C (%) | |
|---|---|---|---|---|---|
| TF-100 | Intravenously | 50 × 6 | 1.19 | 21 | *1 |
| | Intraperitoneally | 100 × 6 | 1.97 | 36 | |
| | Subcutaneously | 100 × 6 | 1.19 | 21 | |
| | — | | 5.54 | 100 | |
| TF-1316 | Intraperitoneally | 2 × 6 | 2.63 | 76 | *1 |
| | | 10 × 6 | 1.57 | 45 | |
| | — | | 3.44 | 100 | |
| TF-132b | Intravenously | 1 × 6 | 5.61 | 62 | *2 |
| | | 5 × 6 | 4.00 | 44 | |
| | | 10 × 6 | 4.32 | 48 | |
| | — | | 9.06 | 100 | |
| TF-133b | Intraperitoneally | 1 × 6 | 6.46 | 71 | *2 |
| | | 5 × 6 | 5.40 | 60 | |
| | | 10 × 6 | 4.00 | 44 | |
| | — | | 9.06 | 100 | |
| TF-1323 | Intraperitoneally | 5 × 7 | 3.48 | 42 | *2 |
| | | 10 × 7 | 3.17 | 38 | |
| | — | | 8.33 | 100 | |
| TF-136 | Intravenously | 1 × 6 | 5.52 | 97 | *2 |
| | | 5 × 6 | 4.88 | 85 | |
| | | 10 × 6 | 3.19 | 56 | |
| | — | | 5.69 | 100 | |
| TF-133b | Intravenously | 1 × 6 | 5.25 | 58 | *2 |
| | | 5 × 6 | 3.61 | 40 | |
| | | 10 × 6 | 3.30 | 36 | |
| | — | | 9.06 | 100 | |

Note:
*1 Determined on the 11th day after the transplantation of the tumor cells.
*2 Determined on the 14th day after the transplantation of the tumor cells.

(2) Ehrlich tumor cells were subcutaneously transplanted at the armpit of ICR strain mice (female, 6 weeks old) in an amount of 4×10⁶ cells per mouse. Subsequently, each of the test substances was administered to the mice divided into groups for intravenous administration, intraperitoneal administration, subcutaneous administration, and intramuscular administration, in a dosage of 10 mg/kg or 20 mg/kg once a day on the first day and from the third day to the seventh day, for control group was administered 0.2 ml of a physiological salt solution in the same manner as above.

The results are shown in Table 12.

TABLE 12

| Substance | Dosage (mg/kg × the number of administrations) | Average survival days (day) | T/C (%) | *Number of survivors/ Number of tested mice | |
|---|---|---|---|---|---|
| TF-132a | 10 × 6 | >26.8 | >140 | 2/6 | *1 |
| | 5 × 6 | >22.2 | >116 | 1/6 | |
| | 1 × 6 | 21.3 | 111 | 0/6 | |
| | — | 19.2 | 100 | 0/6 | |
| TF-133a | 10 × 6 | >30.3 | >158 | 4/6 | *1 |
| | 5 × 6 | >27.5 | >143 | 3/6 | |
| | 1 × 6 | >21.5 | >112 | 1/6 | |
| | — | 19.2 | 100 | 0/6 | |
| TF-136 | 10 × 6 | >30.2 | >157 | 3/6 | *1 |
| | 5 × 6 | >27.3 | >142 | 3/6 | |
| | 1 × 6 | >28.0 | >146 | 2/6 | |
| | — | 19.2 | 100 | 0/6 | |
| TF-132b | 10 × 7 | >42.0 ± 0 | >300 | 5/5 | *2 |
| | 5 × 7 | >42.0 ± 0 | >300 | 5/5 | |
| | — | 14.0 ± 3.3 | 100 | 0/15 | |
| TF-133b | 10 × 7 | >40.0 ± 0 | >286 | 10/10 | *2 |
| | 5 × 7 | >40.0 ± 0 | >286 | 10/10 | |
| | 1 × 7 | >37.3 ± 6.3 | >266 | 7/10 | |
| | — | 14.0 ± 3.3 | 100 | 0/15 | |
| TF-1323 | 5 × 7 | >34 ± 0.6 | >255 | 6/7 | *2 |
| | 1 × 7 | >32 ± 3.6 | >240 | 5/7 | |
| | — | 13.6 ± 3.6 | 100 | 0/7 | |
| TF-1316 | 5 × 7 | >28.8 ± 11.5 | >201 | 5/10 | *1 |
| | 1 × 7 | >30.9 ± 9.5 | >216 | 4/10 | |
| | — | 14.3 ± 2.9 | 100 | 0/10 | |
| TF-136 | 5 × 6 | >38.0 ± 8.9 | >271 | 4/5 | *2 |
| | 1 × 6 | >24.8 ± 12.3 | >177 | 1/5 | |
| | — | 14.0 ± 2.5 | 100 | 0/5 | |

Note:
*1 The judgement on the 35th day after the transplantation of the tumor cells.
*2 The judgement on the 40th day after the transplantation of the tumor cells.
In both *1 and *2, the survivors were in complete cure state.

6 days in total, after the transplantation of the tumor cells. To the control group was administered 0.2 ml of a physiological salt solution in the same manner as above. The weights of the tumors were determined on the 13th day after the transplantation of the tumor cells.

The results are as shown in Table 11.

TABLE 11

| Substance | Administration route | Dosage (mg/kg) | Average tumor weight (g) | T/C (%) |
|---|---|---|---|---|
| TF-132a | Intravenously | 10 | 3.83 | 47 |
| | | — | 8.11 | 100 |
| TF-133a | Intravenously | 10 | 1.81 | 26 |
| | | 20 | 1.84 | 26 |
| | Intraperitoneally | 10 | 2.82 | 40 |
| | | 20 | 1.82 | 26 |
| | Subcutaneously | 10 | 3.57 | 51 |
| | | 20 | 2.86 | 41 |
| | Intramuscularly | 10 | 4.65 | 67 |
| | | 20 | 3.22 | 46 |
| | — | — | 6.99 | 100 |

As is evident from Tables 10 and 11, a tumor growth-inhibiting effect is observed in the groups to which each of the TF-substances of this invention was administered.

(c) Antitumor activity against Sarcoma-180 carcinoma

Sarcoma-180 carcinoma were intraperitoneally transplanted to ICR strain mice (female, 6 weeks old) in an amount of $1 \times 10^5$ cells per mouse. Subsequently, each of the test substances was intraperitoneally administered to the mice in a dosage of 1 mg/kg, 5 mg/kg or 10 mg/kg once a day from the first day to the seventh day repeatedly, for 7 days in total, after the transplantation of the tumor cells, or once a day on the first day and from the third day to the seventh day for six days in total. To the control group was administered 0.2 ml of a physiological salt solution in the same manner as above.

The results are shown in Table 12.

As is evident from Table 12, the groups to which each of the TF-substances of this invention was administered had antitumor activities, as compared with the control group.

(d) Antitumor activity against B-16 melanoma (1) B-16 Melanoma tumor cells were subcutaneously transplanted at the armpit to BDF$_1$ strain mice (male, 7 weeks old) in an amount of $1 \times 10^6$ cells per mouse. Subsequently, TF-133a was intraperitoneally administered to the mice in a dosage of 5 mg/kg or 10 mg/kg once a day on the first day and from the third day to the seventh day, for 6 days in total, after the transplantation of the tumor cells. In the same manner as above, 0.2 ml of a physiological salt solution was administered to the control group, and 20 mg/kg of 5-FU to the group for 5-FU administration.

The results are as shown in Table 13.

TABLE 13

| Substance | Dosage (mg/kg × the number of administrations) | Average tumor weight (g) | T/C (%) |
|---|---|---|---|
| TF-133a | 5 × 6 | 4.07 | 70 |
| | 10 × 6 | 2.52 | 43 |
| 5-FU | 20 × 6 | 4.21 | 72 |
| Control | — | 5.84 | 100 |

As is evident from Table 13, the groups to which TF-133a was administered had an apparent tumor growth-inhibiting activity, as compared with the control group, and the groups to which each of 5 mg/kg and 10 mg/kg of TF-133a was administered had equal and more remarkable tumor growth-inhibiting activity, respectively, as compared with the group to which 5-FU was administered.

(2) The transplantation of B-16 melanoma tumor cells and the administration of TF-132a, TF-133a, 5-FU and a physiological salt solution were carried out in the same manner as in above (1). On the 21st day after the transplantation of the tumor cells, the mice were dissected, and the metastasis of the melanoma tumor cells to the lungs was observed.

The results are shown in Table 14.

TABLE 14

| Substance | Dosage (mg/kg × the number of administrations) | Average number of metastasis | Percentage of metastasis inhibition (%) |
|---|---|---|---|
| TF-132a | 5 × 6 | 16.0 | 48 |
|  | 10 × 6 | 9.86 | 69 |
| TF-133a | 5 × 6 | 9.3 | 70 |
|  | 10 × 6 | 6.7 | 78 |
| 5-FU | 20 × 6 | 24.8 | 20 |
| Control | — | 31.0 | 0 |

As is evident from Table 14, in the groups to which each of TF-132a and TF-133a was administered, the metastasis of B-16 melanoma tumor cells was remarkably inhibited, as compared with the group to which 5-FU was administered.

(IV) Acute toxicity $LD_{50}$ for mice is as shown in Table 15.

TABLE 15

| Substance | Administration route | $LD_{50}$ (mg/kg) |
|---|---|---|
| TF-100 | Intraperitoneally | 500 |
| TF-110 | Intravenously | >250 |
|  | Intraperitoneally | >1000 |
| TF-120 | Intravenously | >250 |
|  | Intraperitoneally | >1000 |
| TF-132a | Intravenously | 300 |
|  | Intraperitoneally | >500 |
| TF-133a | Intravenously | 300 |
|  | Intraperitoneally | >500 |
| TF-136 | Intravenously | 300 |
|  | Intraperitoneally | >500 |
| TF-132b | Intravenously | >100 |
| TF-133b | Intravenously | >200 |
| TF-140 | Intravenously | >100 |
| TF-150 | Intravenously | >200 |
| TF-1323 | Intravenously | >200 |
| TF-1316 | Intravenously | >200 |

As is evident from the above-mentioned pharmacological experiments, the TF-substances of this invention are useful as carcinostatic agents, in lower warm-blooded animals can be expected to have activities against various cancerous diseases in lower warm-blooded animals, and can be expected to have remarkable activities against particularly solid cancers in lower warm-blooded animals. All the TF-substances of this invention have excellent effects, though TF-130, particularly, 132a, 132b, 133a, 133b and 1323 are preferred from a consideration of various points.

The TF-substances of this invention may be used after shaping them into various pharmaceutical forms such as oral drugs, injections, suppositories or the like, though they are used preferably in the pharmaceutical form of an injection. When they are used as oral drugs, the oral drugs may contain various excipients, and may be formed into capsules, tablets, powder, or granules. When they are used as injections, the injections may be any of subcutaneous injections, intramuscular injections, and intravenous injections, and they are used in the form of a suspension, a solution or a powder which is dissolved when used. The injections may contain a local anesthetics.

The dosage of the TF-substances of this invention is properly selected depending on the conditions of the lower warm-blooded animal host, though in general it is desirable to administer them in a dosage for a lower warm-blooded animal of 0.01 to 50 mg/kg once a day or several times a day, and as to the administration method, they are administered preferably by subcutaneous, intramuscular, or intravenous injection or injection into the affected part.

This invention is further explained below referring to Examples, and the accompanying drawings, in which FIG. 1 shows a microscopic photography showing the form of *Fusobacterium nucleatum* TF-031 used in this invention, FIG. 2 shows an infrared absorption spectrum of the substance TF-100;

FIG. 18 shows an infrared absorption spectrum of the substance TF-132a;

FIG. 24 shows an elution pattern obtained when said substance was subjected to gel filtration by using Sephadex G-200;

FIG. 26 shows an infrared absorption spectrum of the substance TF-133a;

EXAMPLE 1

Figure 1:
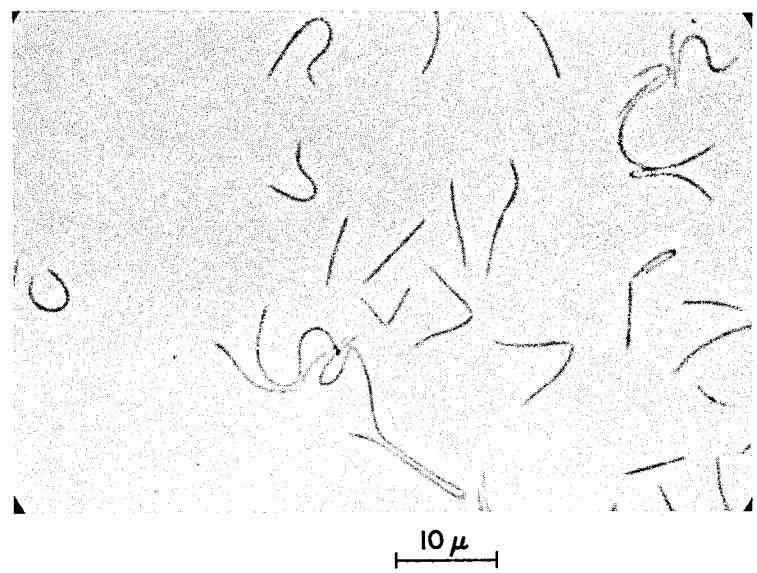
Figure 2:
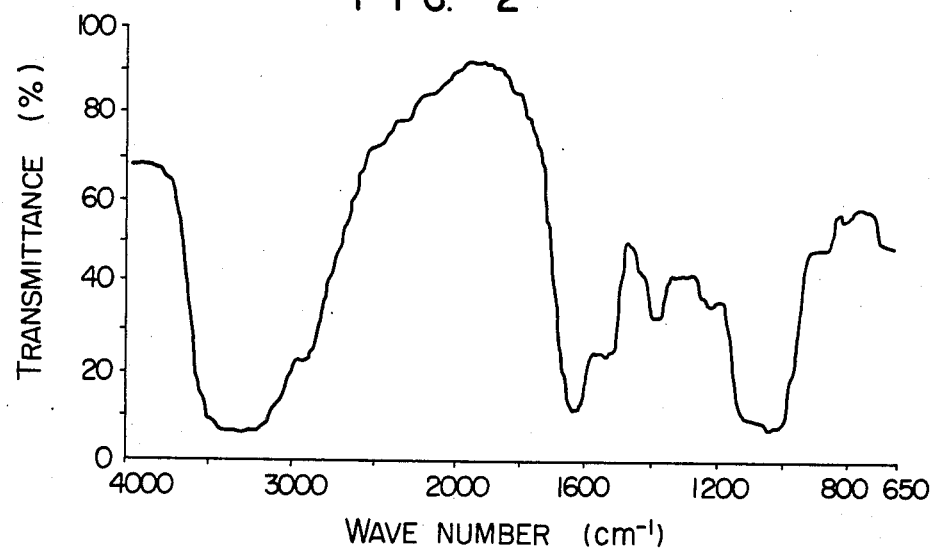
Figure 3:
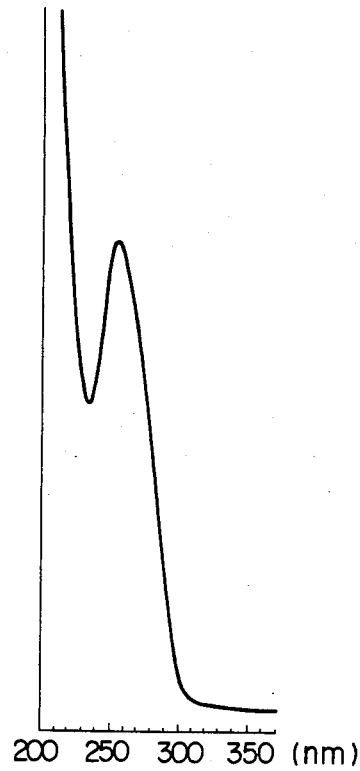
FIG. 3 shows an ultraviolet absorption spectrum of said substance.
Figure 4:
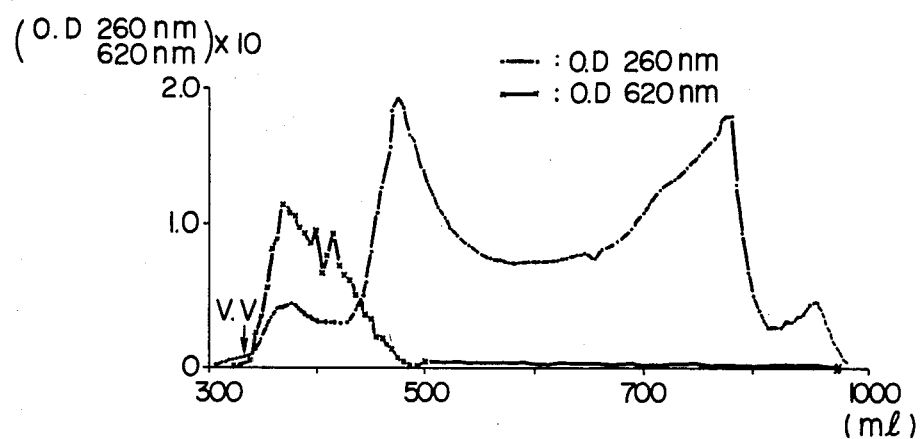
FIG. 4 shows an elution pattern obtained when said substance was subjected to gel filtration by using Sephadex G-50.
Figure 5:
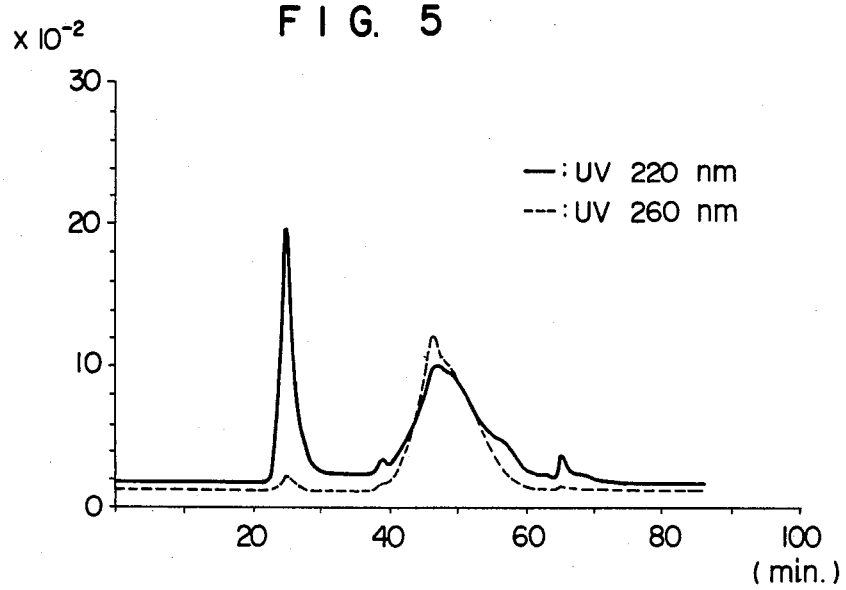
FIG. 5 shows a high performance liquid chromatogram.
Figure 6:
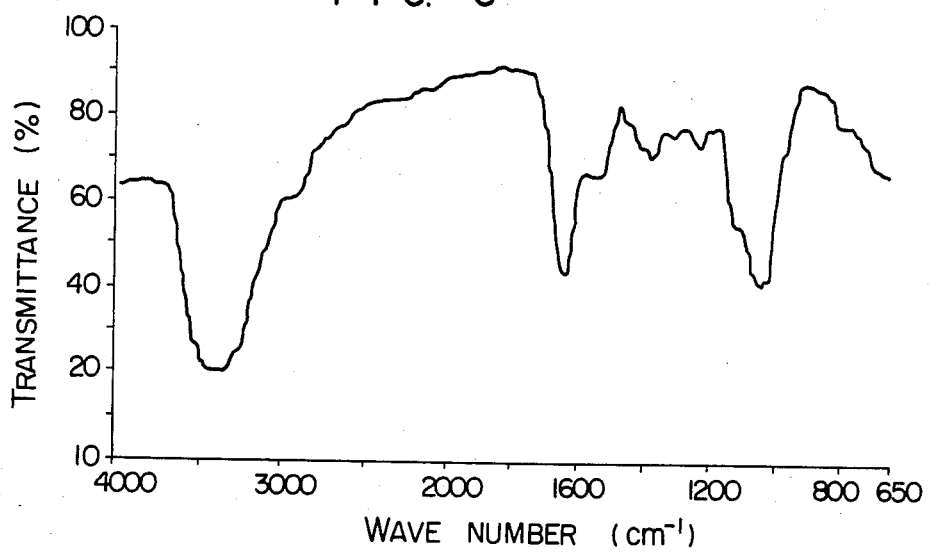
FIG. 6 shows an infrared absorption spectrum of the substance TF-110.
Figure 7:
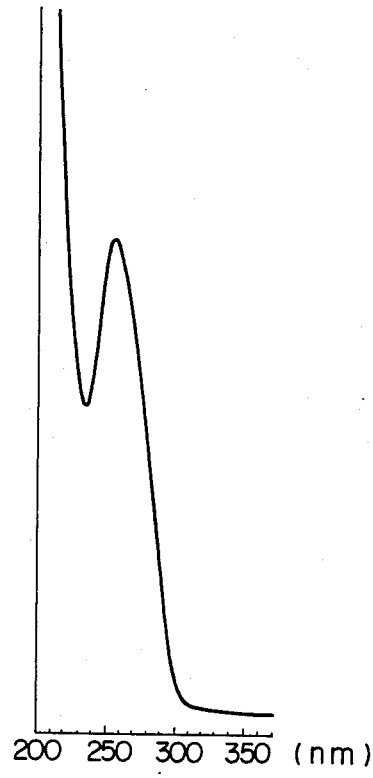
FIG. 7 shows an ultraviolet absorption spectrum of said substance.
Figure 8:
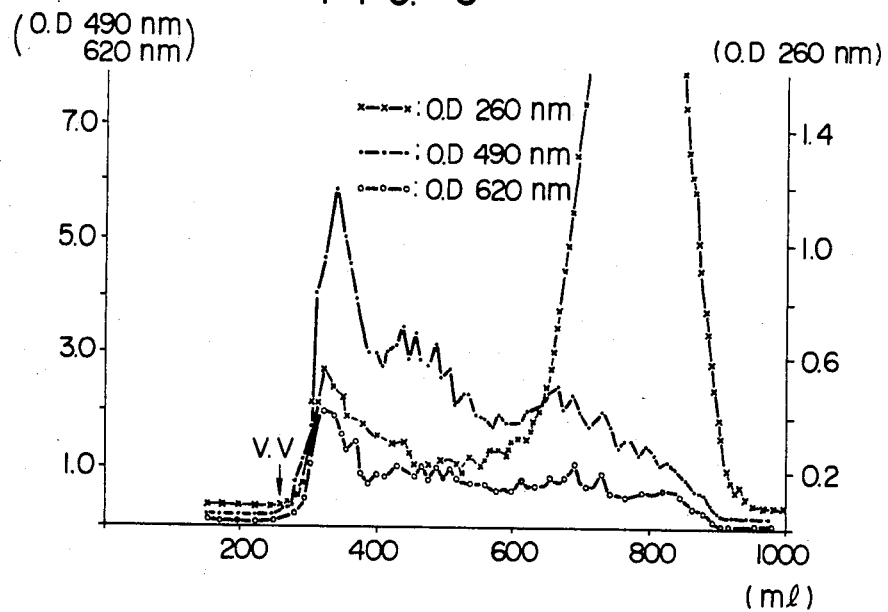
FIG. 8 shows an elution pattern obtained when said substance was subjected to gel filtration by using Sephadex G-200.
Figure 9:
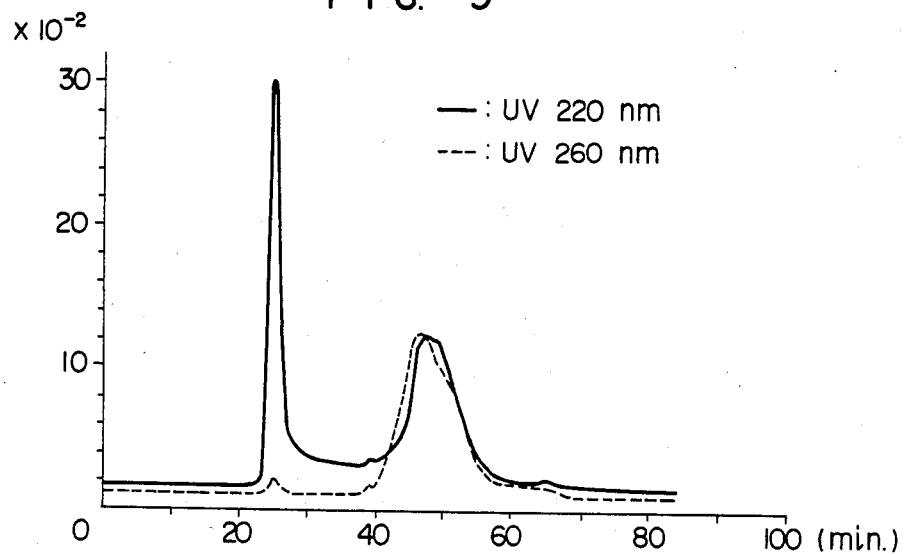
FIG. 9 shows a high performance liquid chromatogram of said substance.
Figure 10:
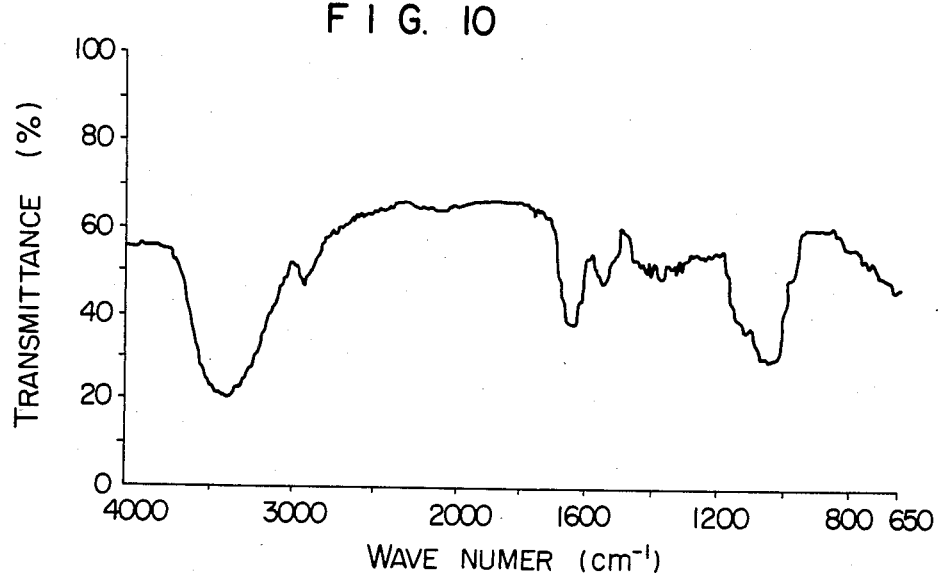
FIG. 10 shows an infrared absorption spectrum of the substance TF-120.
Figure 11:
FIG. 11 shows an ultraviolet absorption spectrum of said substance.
Figure 12:
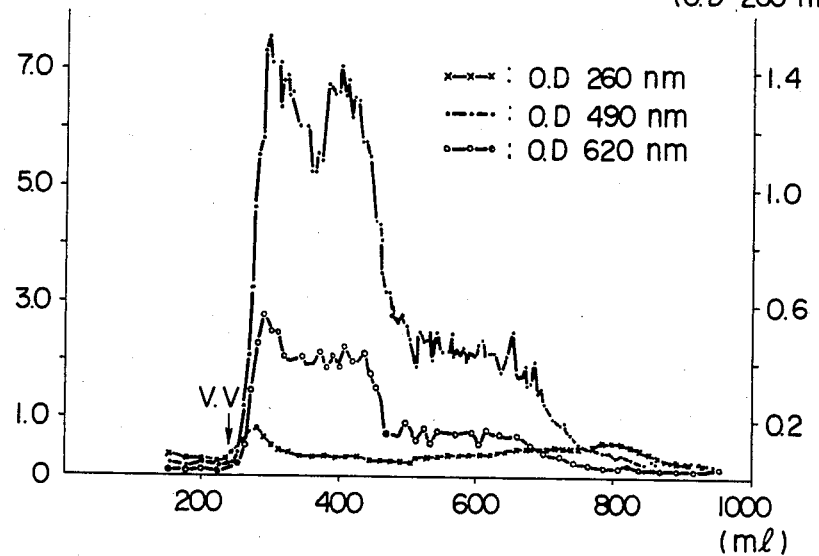
FIG. 12 shows an elution pattern obtained when said substance was subjected to gel filtration by using Sephadex G-200.
Figure 13:
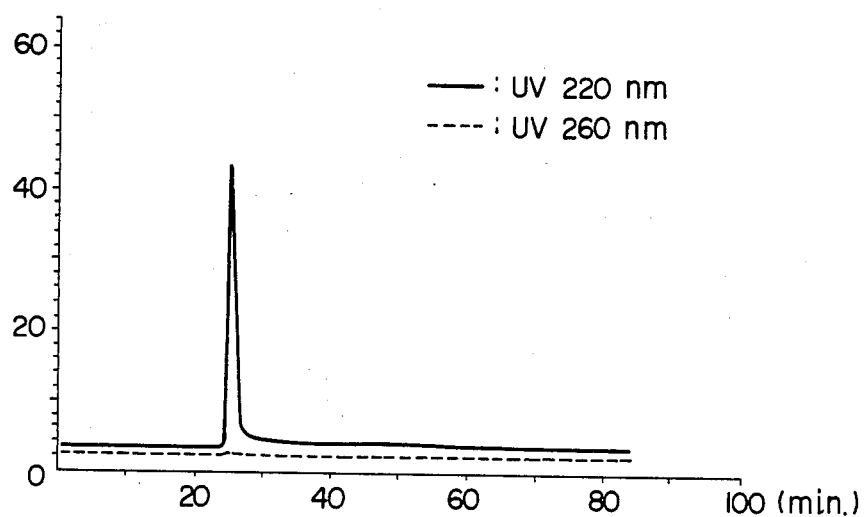
FIG. 13 shows a high performance liquid chromatogram of said substance.
Figure 14:
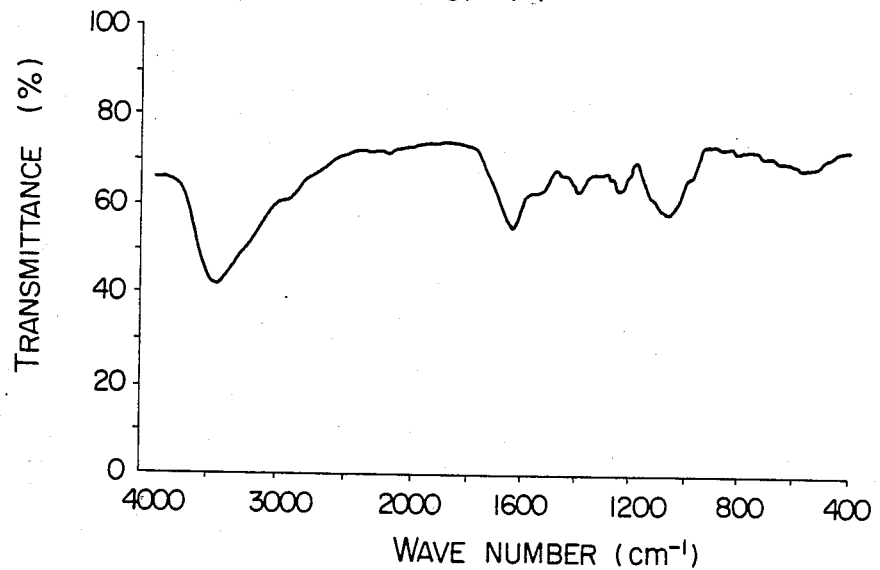
FIG. 14 shows an infrared absorption spectrum of the substance TF-1316.
Figure 15:
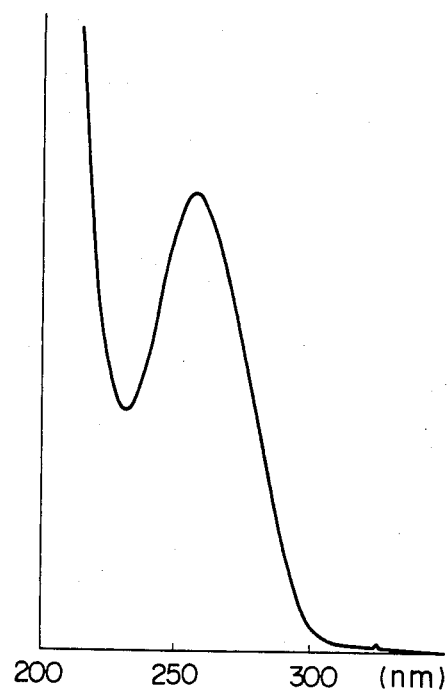
FIG. 15 shows an ultraviolet absorption spectrum of said substance.
Figure 16:
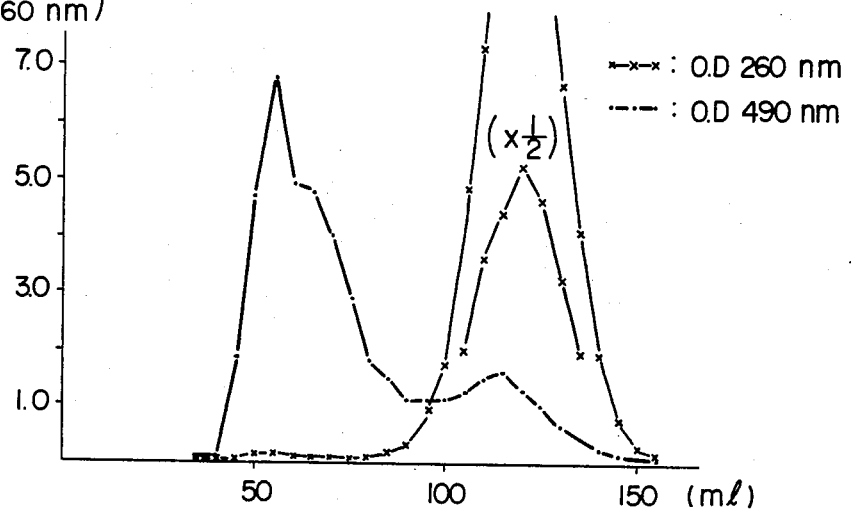
FIG. 16 shows an elution pattern obtained when said substance was subjected to gel filtration by using Sephadex G-200.
Figure 17:
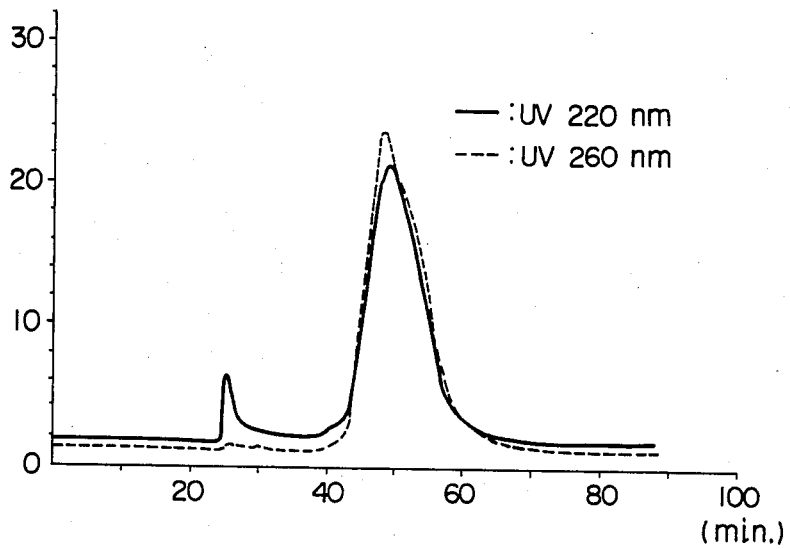
FIG. 17 shows a high performance liquid chromatogram of said substance.
Figure 18:
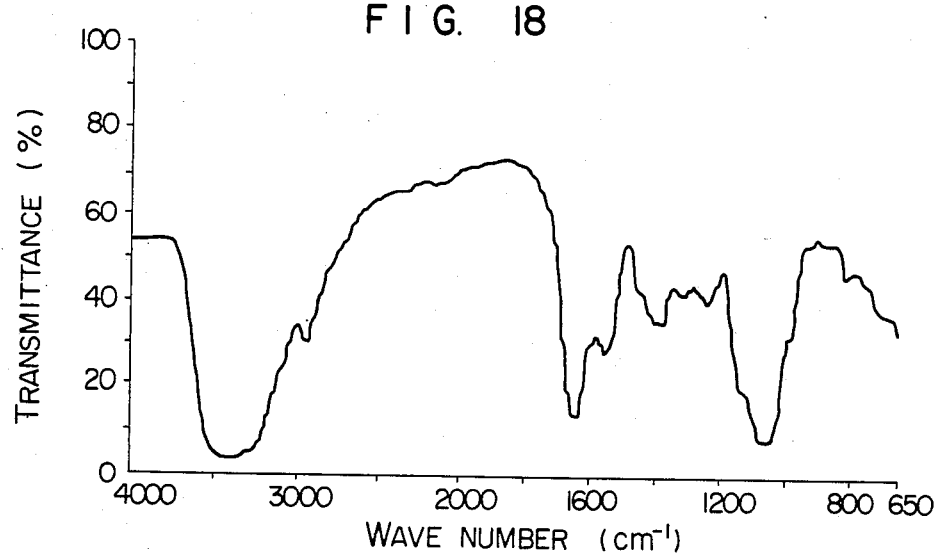
Figure 19:
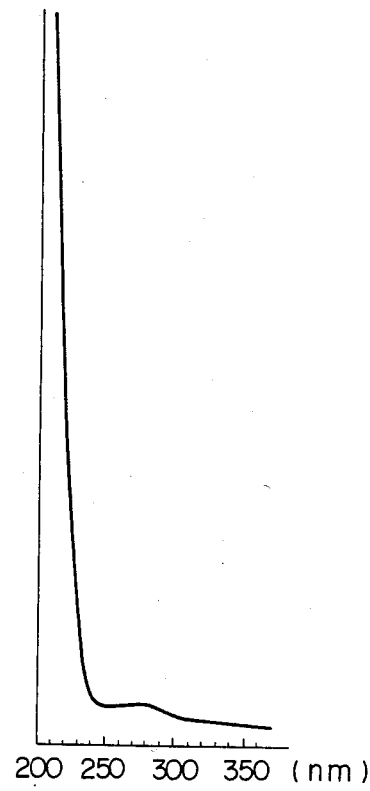
FIG. 19 shows an ultraviolet absorption spectrum of said substance.
Figure 20:
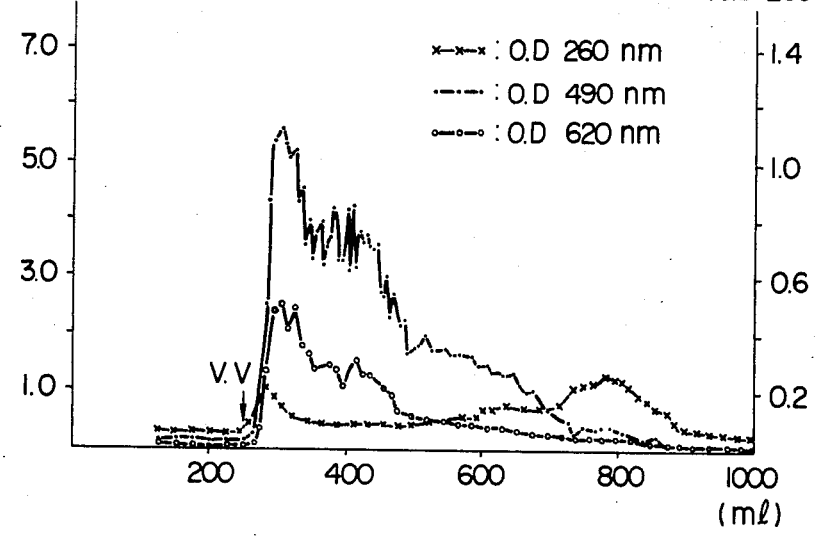
FIG. 20 shows an elution pattern obtained when said substance was subjected to gel filtration by using Sephadex G-200.
Figure 21:
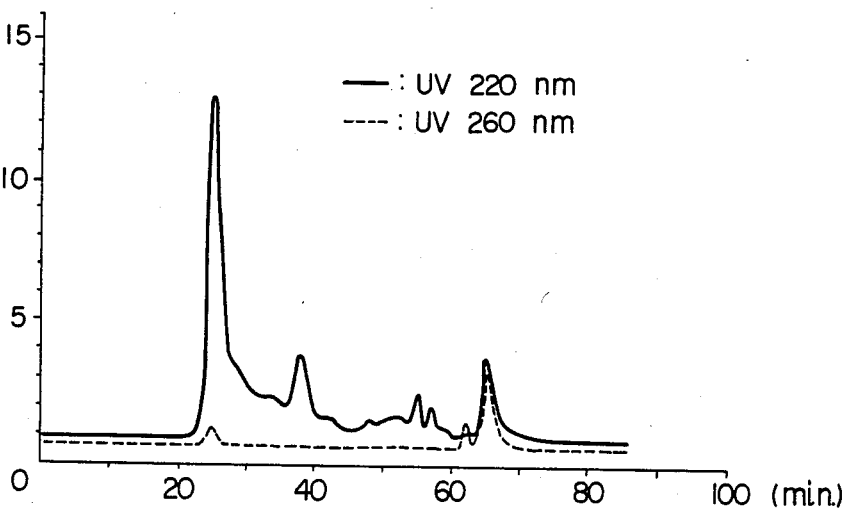
FIG. 21 shows a high performance liquid chromatogram of said substance.
Figure 22:
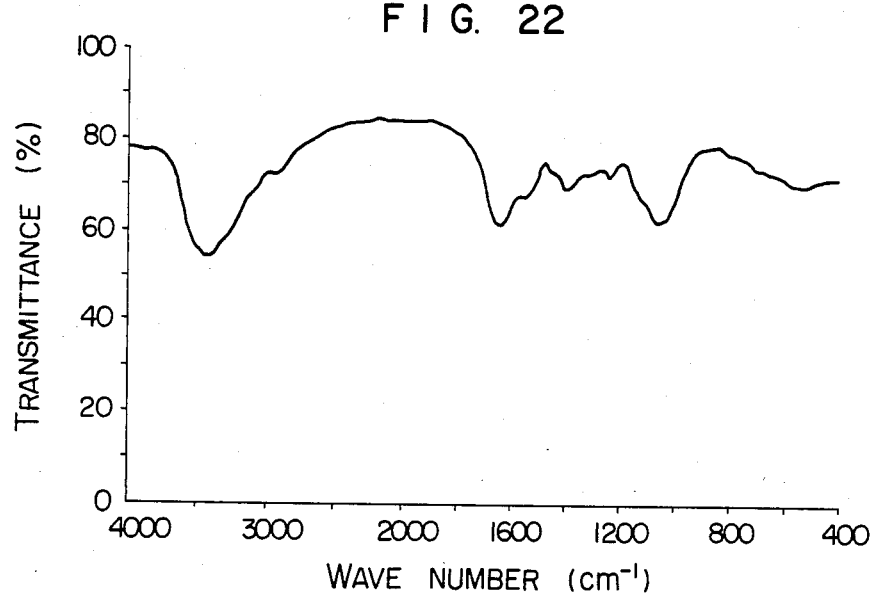
FIG. 22 shows an infrared absorption spectrum of the substance TF-132b.
Figure 23:
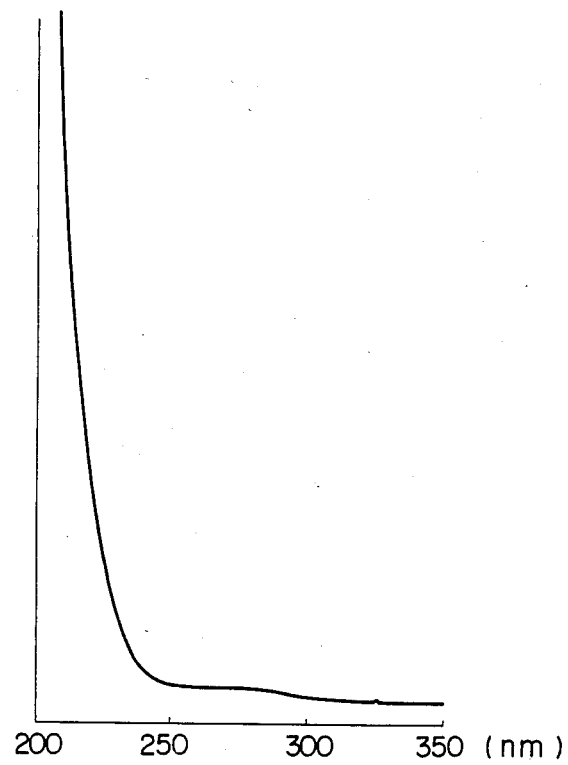
FIG. 23 shows an ultraviolet absorption spectrum of said substance.
Figure 25:
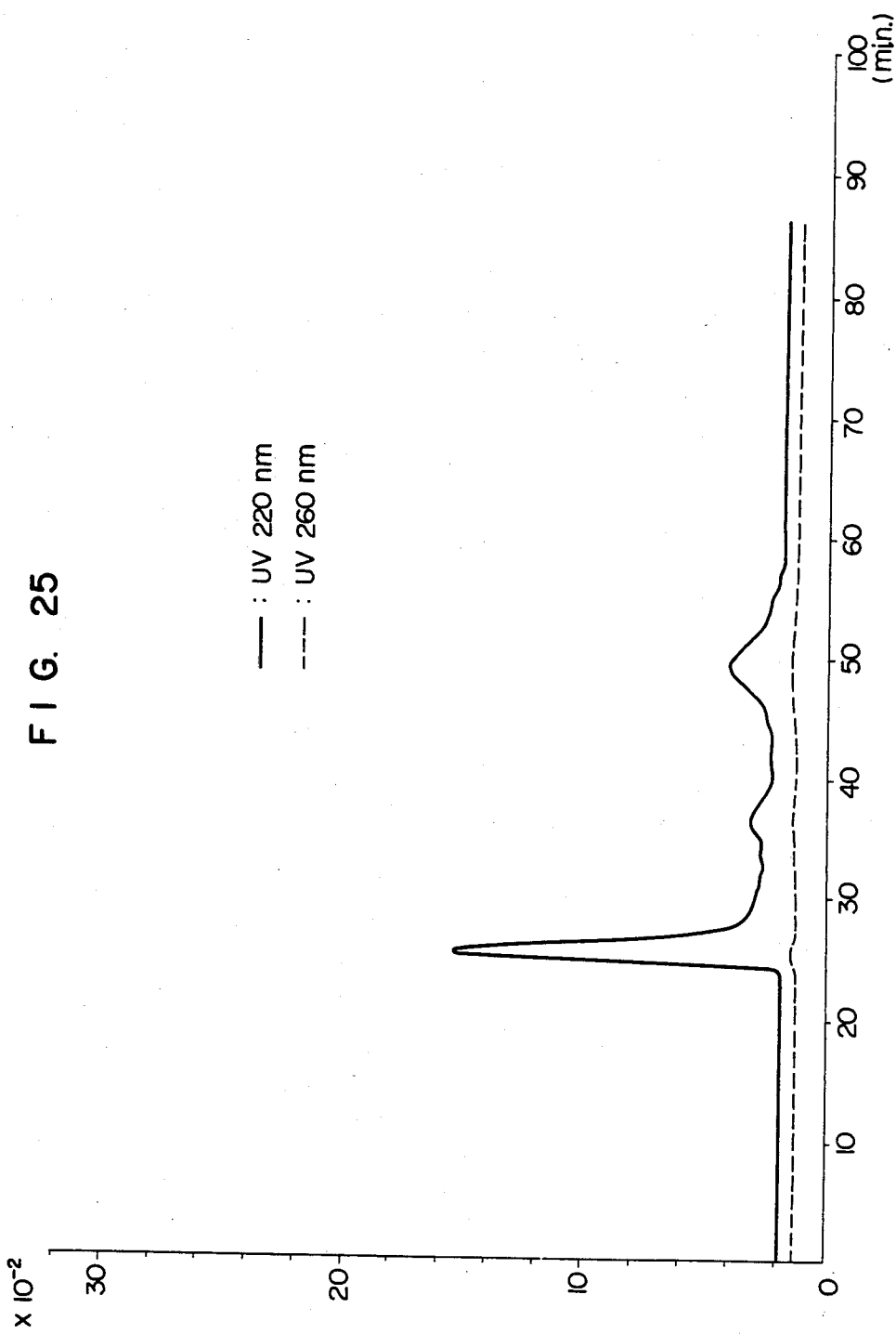
FIG. 25 shows a high performance liquid chromatogram of said substance.
Figure 27:
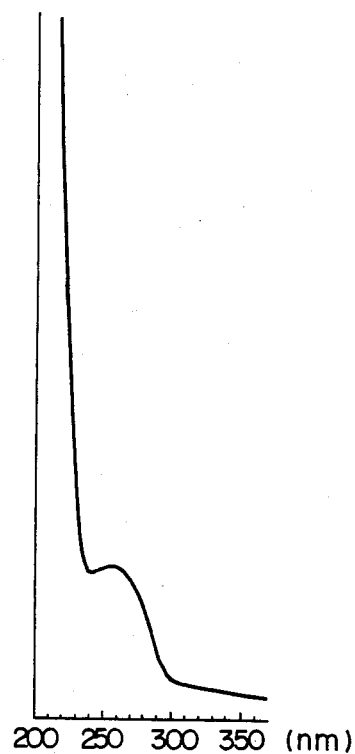
FIG. 27 shows an ultraviolet absorption spectrum of said substance.
Figure 28:
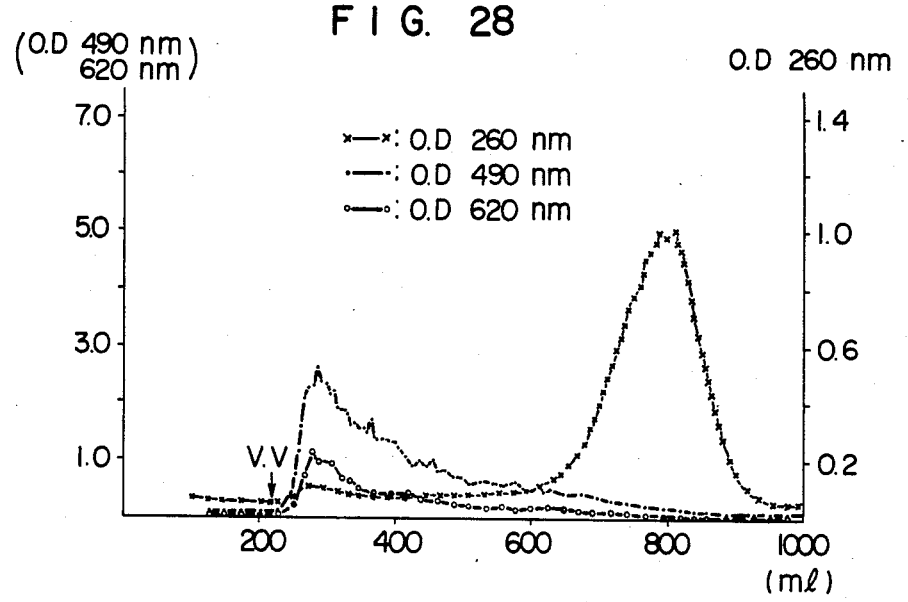
FIG. 28 shows an elution pattern obtained when said substance was subjected to gel filtration by using Sephadex G-200.
Figure 29:
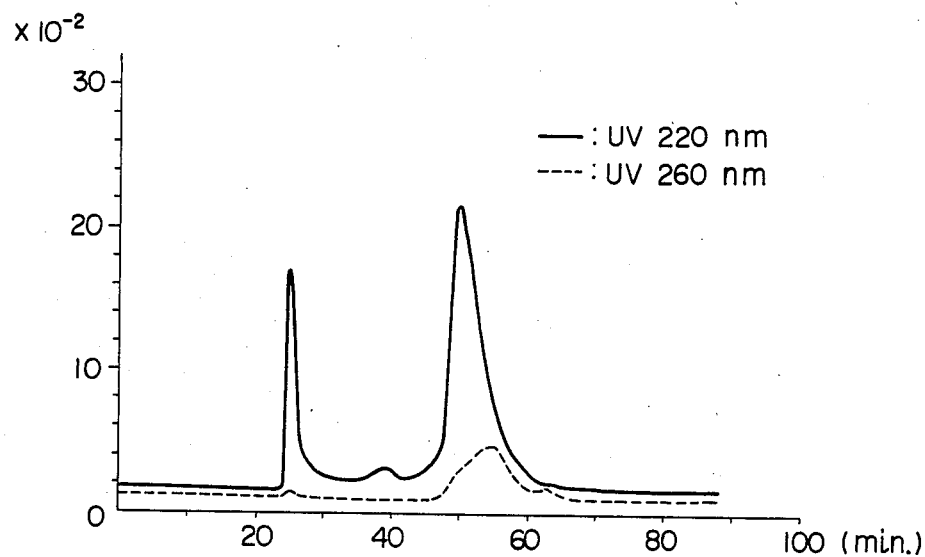
FIG. 29 shows a high performance liquid chromatogram of said substance.
Figure 30:
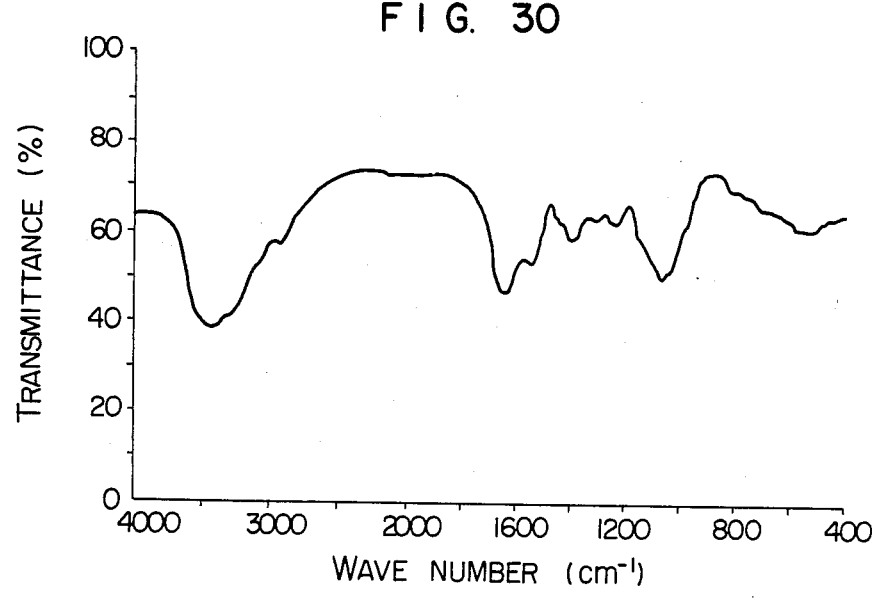
FIG. 30 shows an infrared absoprtion spectrum of the substance TF-133b.
Figure 31:
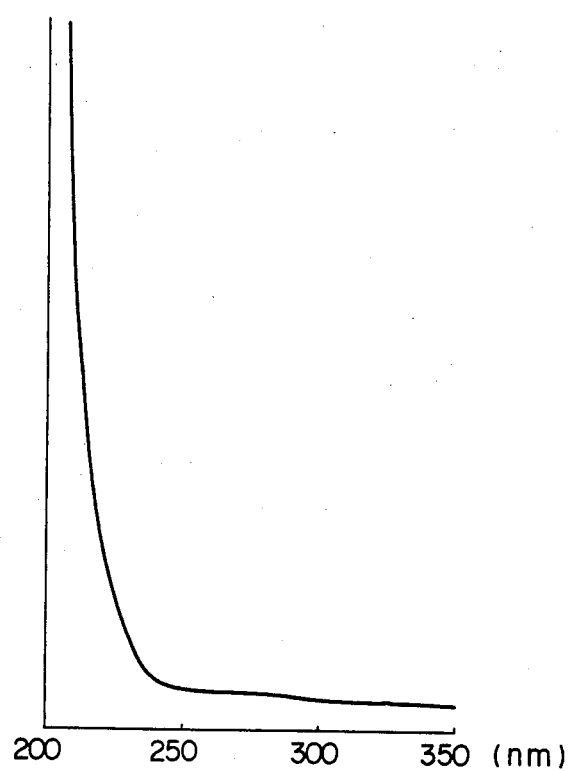
FIG. 31 shows an ultraviolet absorption spectrum of said substance.
Figure 32:
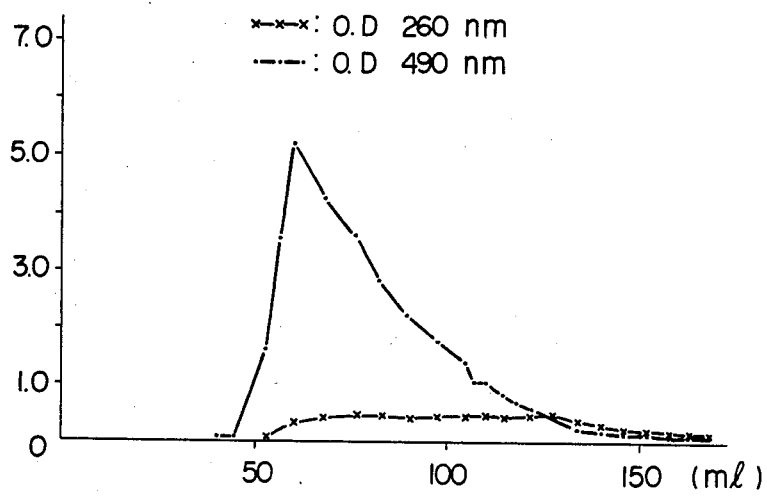
FIG. 32 shows an elution pattern obtained when said substance was subjected to gel filtration by using Sephadex G-200.
Figure 33:
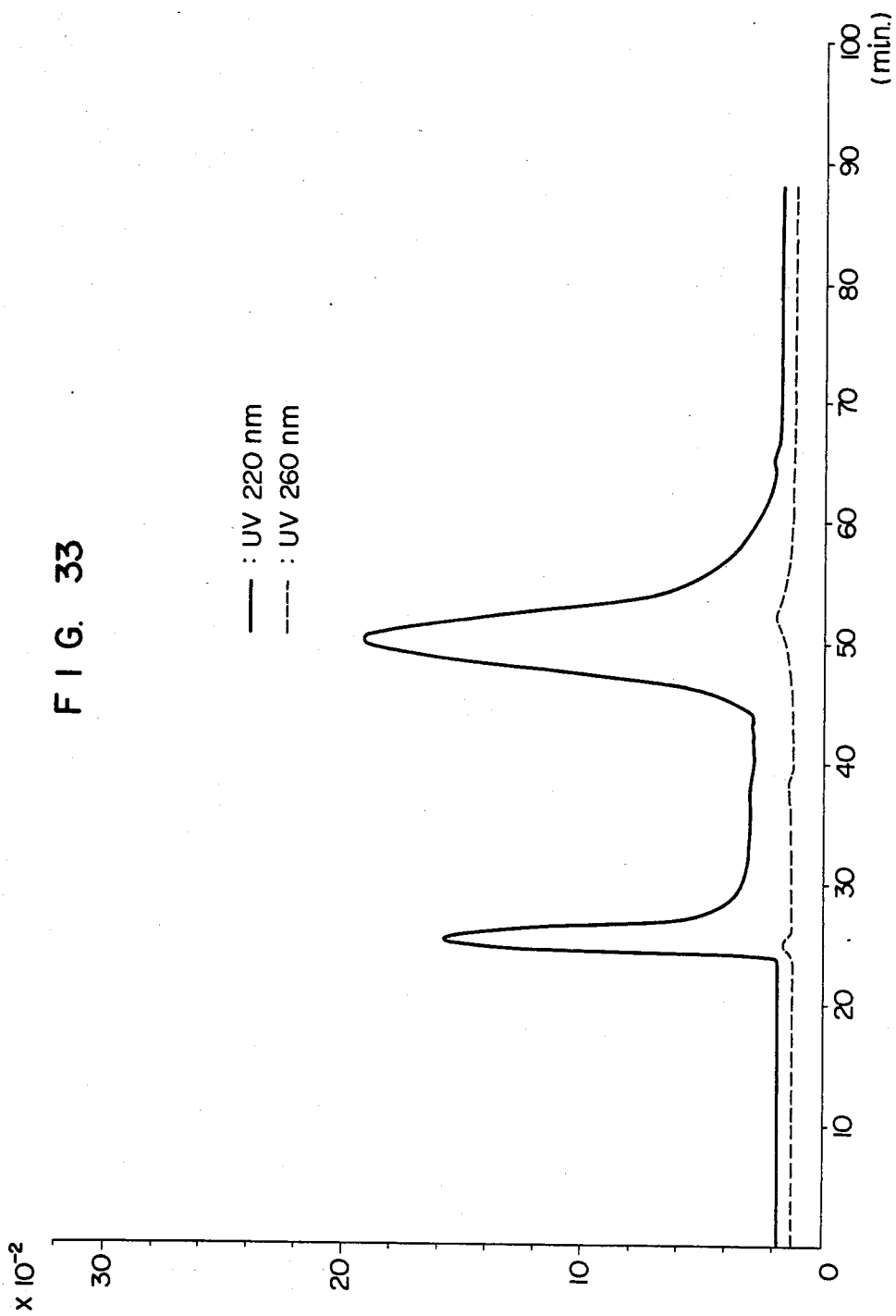
FIG. 33 shows a high performance liquid chromatogram of said substance.
Figure 34:
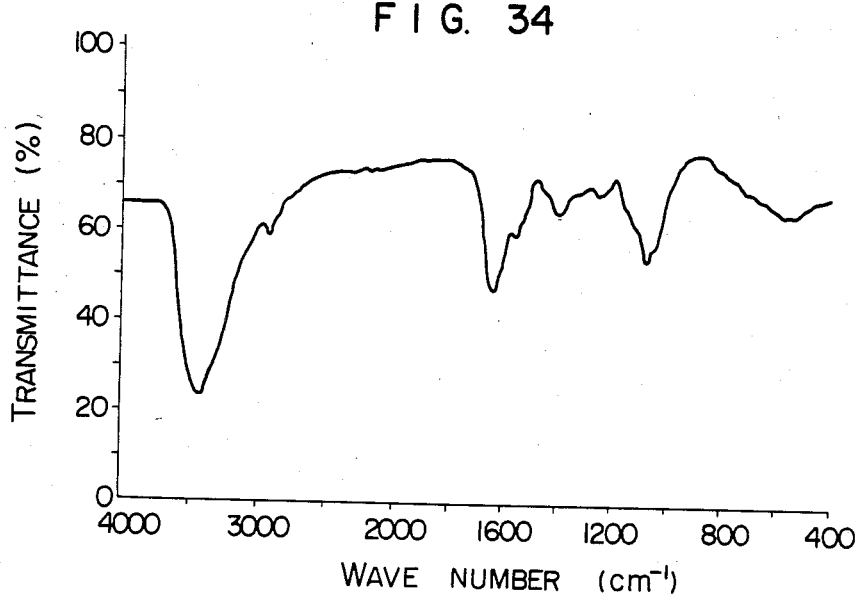
FIG. 34 shows an infrared absorption spectrum of the substance TF-1323.
Figure 35:
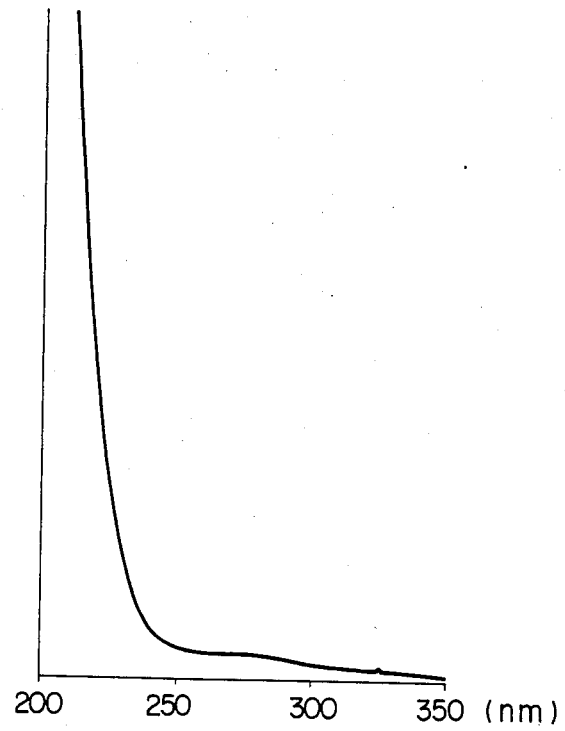
FIG. 35 shows an ultraviolet absorption spectrum of said substance.
Figure 36:
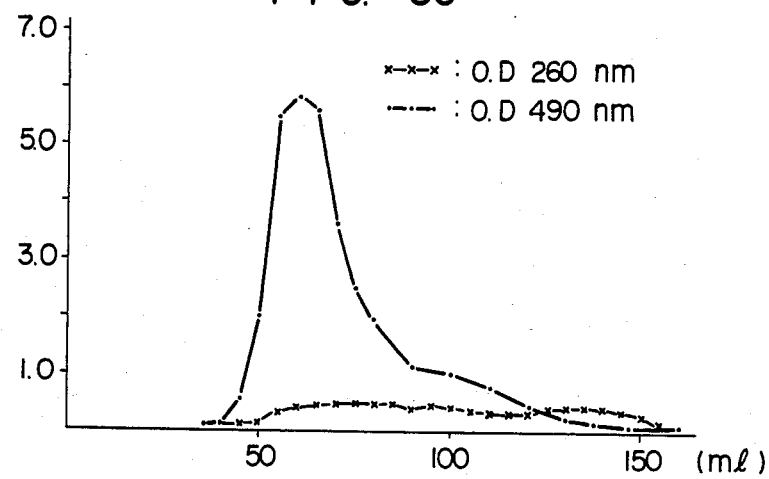
FIG. 36 shows an elution pattern obtained when said substance was subjected to gel filtration by using Sephadex G-200.
Figure 37:
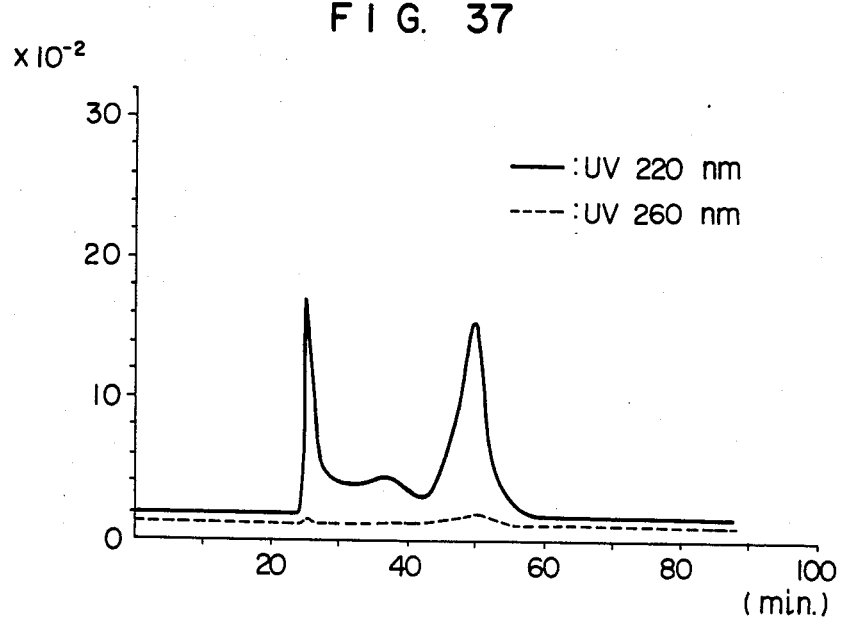
FIG. 37 shows a high performance liquid chromatogram of said substance.
Figure 38:
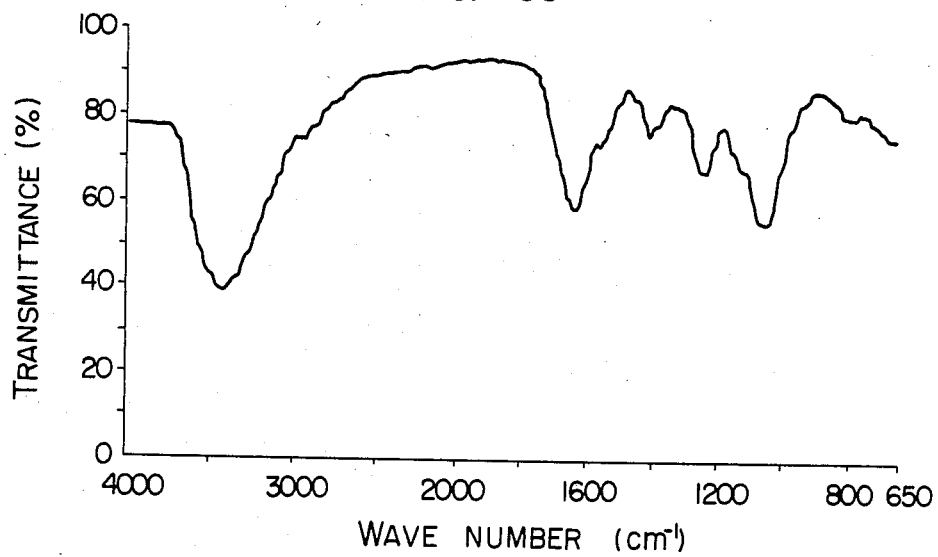
FIG. 38 shows an infrared absorption spectrum of the substance TF-136.
Figure 39:
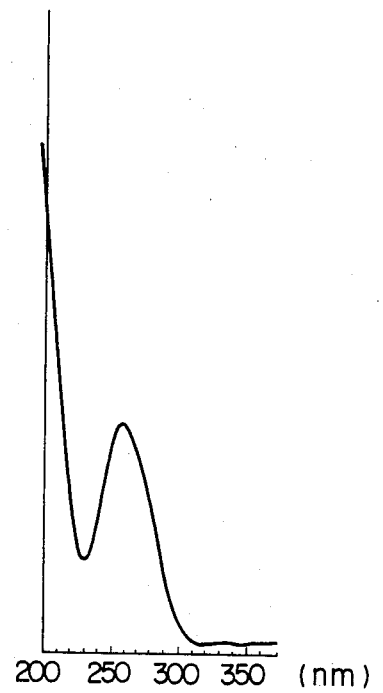
FIG. 39 shows an ultraviolet absorption spectrum of said substance.
Figure 40:
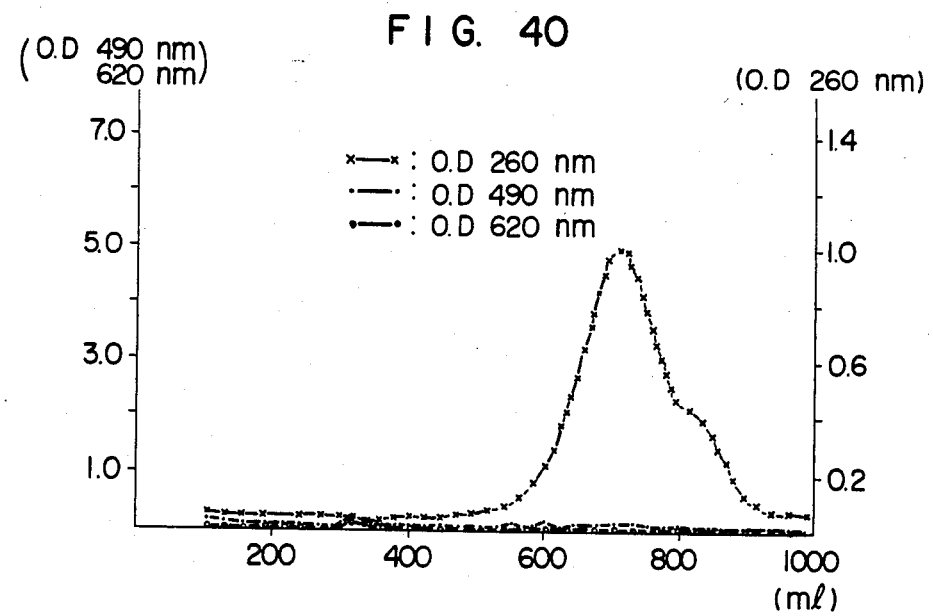
FIG. 40 shows an elution pattern obtained when said substance was subjected to gel filtration by using Sephadex G-200.
Figure 41:
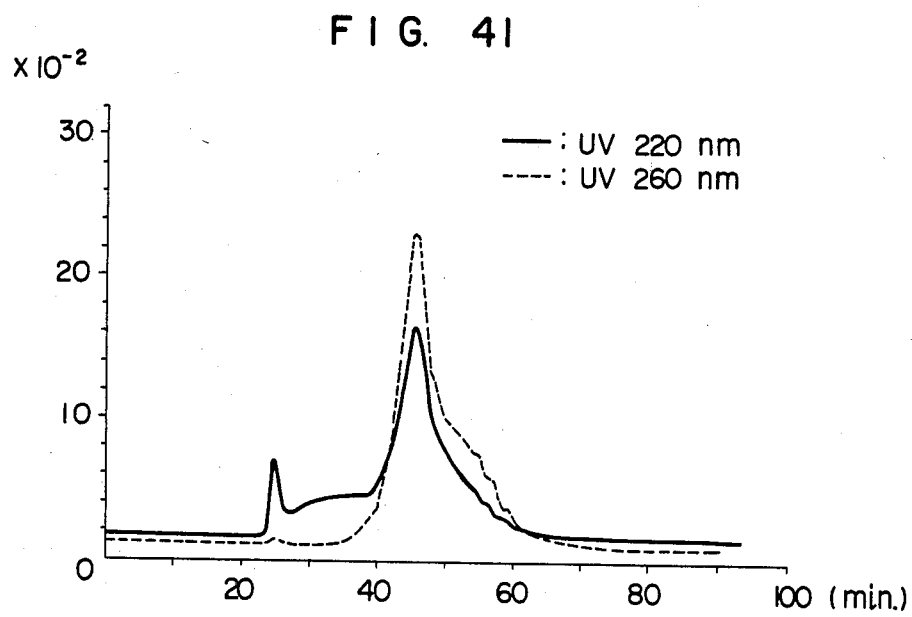
FIG. 41 shows a high performance liquid chromatogram of said substance.
Figure 42:
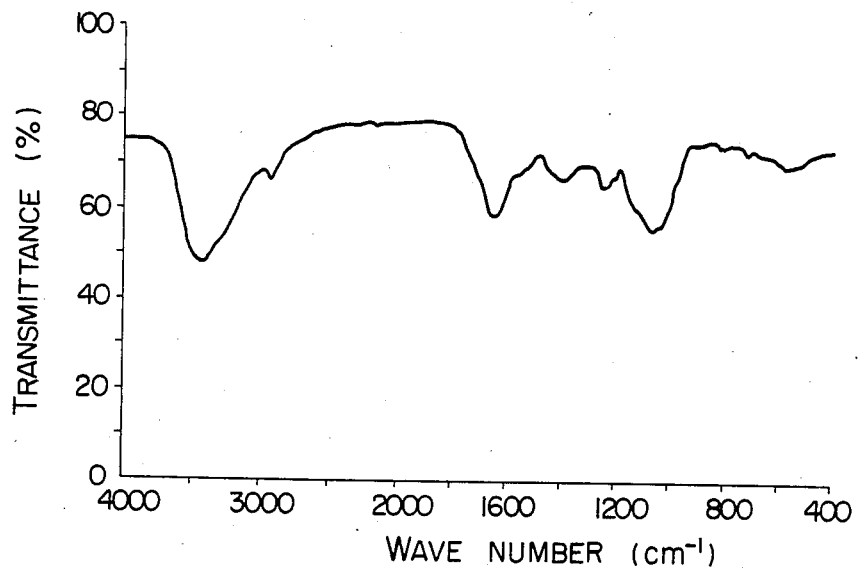
FIG. 42 shows an infrared absorption spectrum of the substance TF-140.
Figure 43:
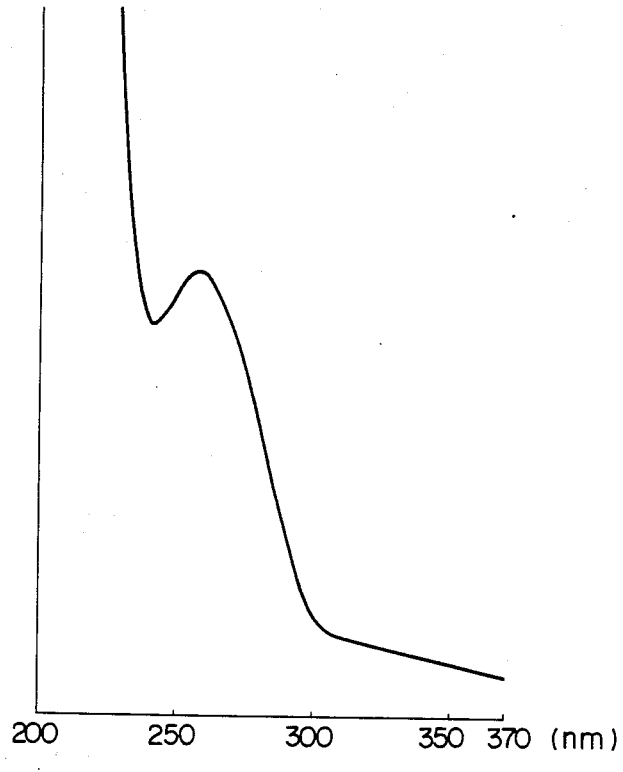
FIG. 43 shows an ultraviolet absorption spectrum of said substance.
Figure 44:
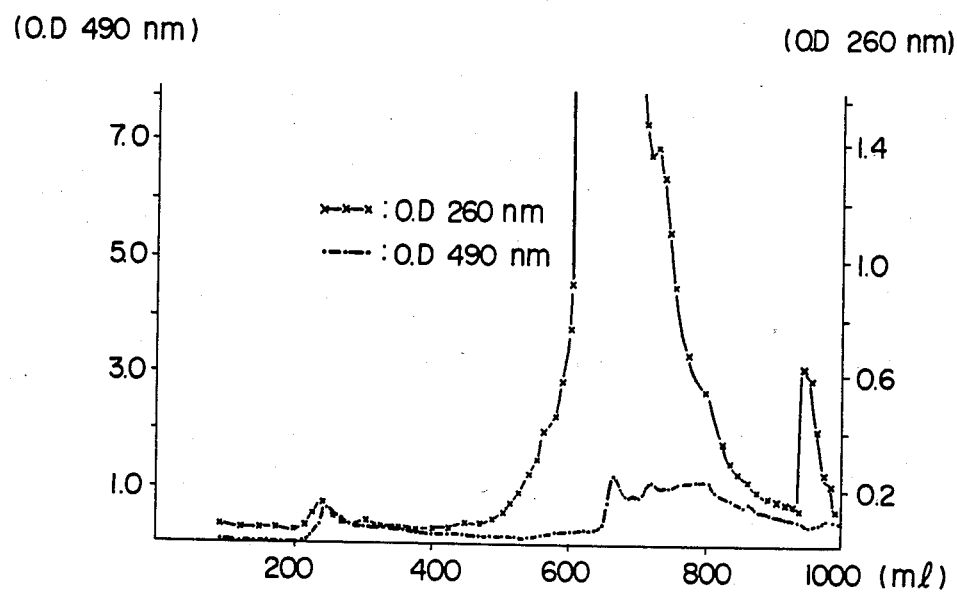
FIG. 44 shows an elution pattern obtained when said substance was subjected to gel filtration by using Sephadex G-200.
Figure 45:
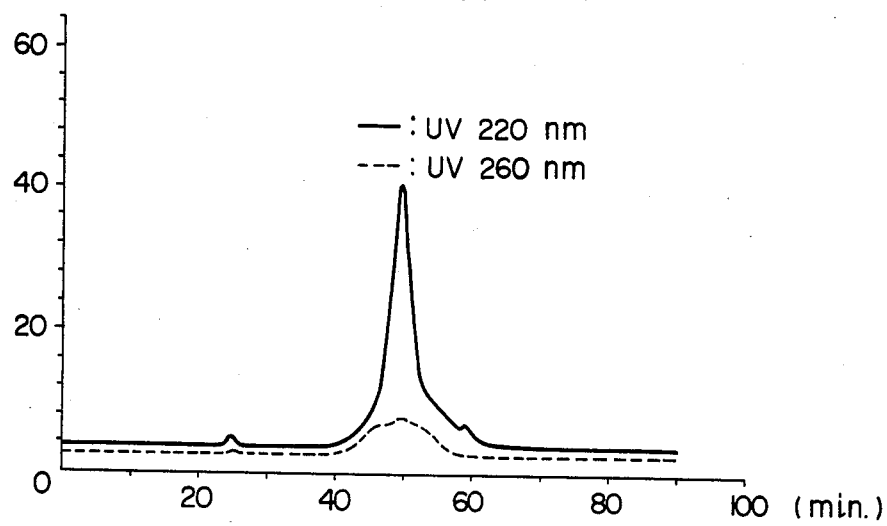
FIG. 45 shows a high performance liquid chromatogram of said substance.
Figure 46:
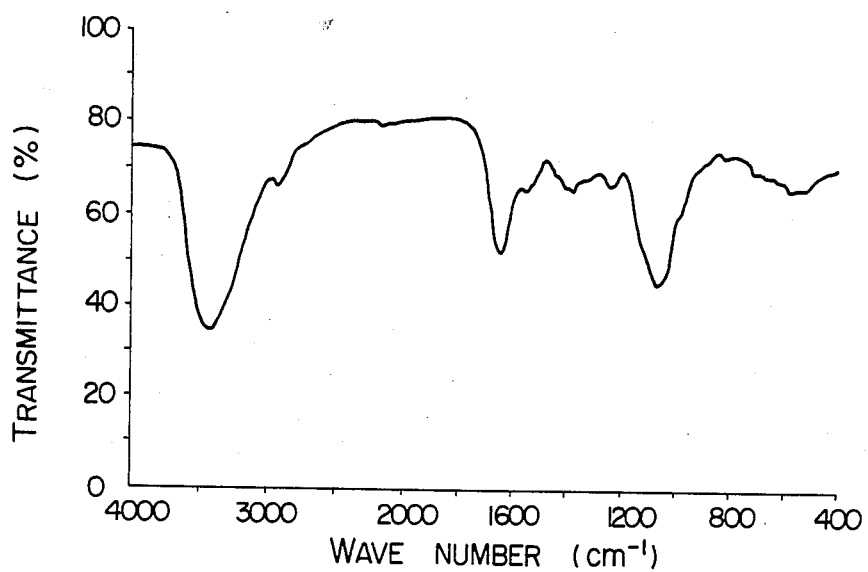
FIG. 46 shows an infrared absorption spectrum of the substance TF-150.
Figure 47:
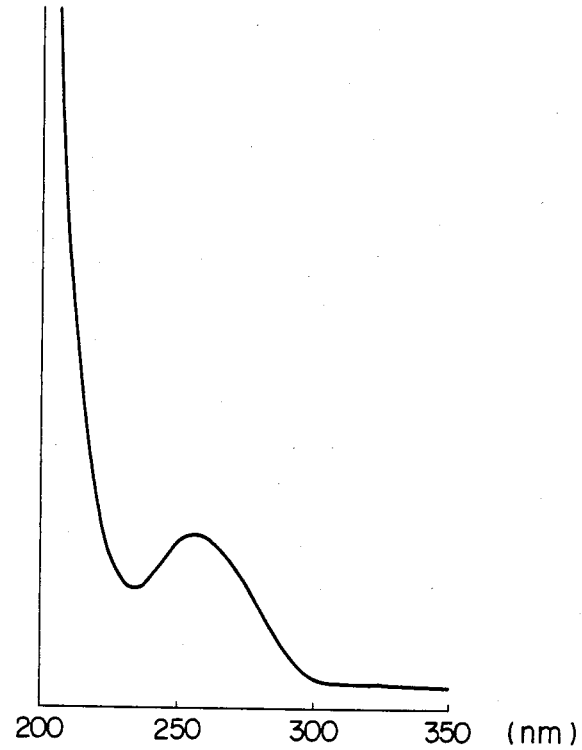
FIG. 47 shows an ultraviolet absorption spectrum of said substance.
Figure 48:
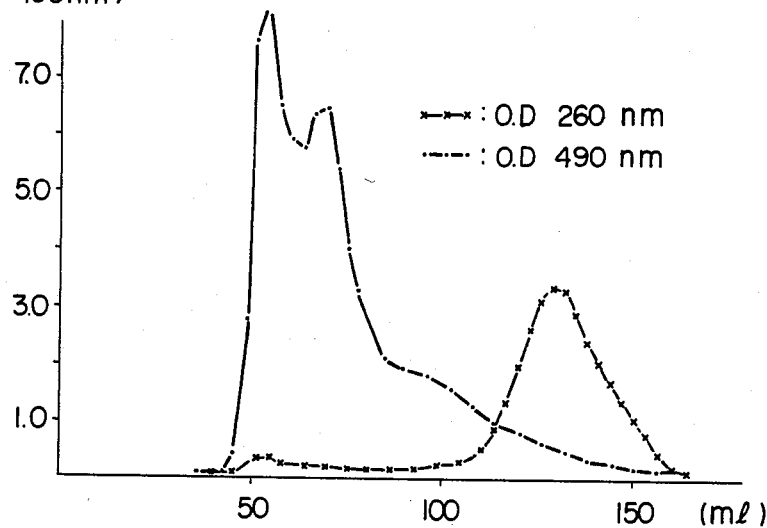
FIG. 48 shows an elution pattern obtained when said substance was subjected to gel filtration by using Sephadex G-200.
Figure 49:
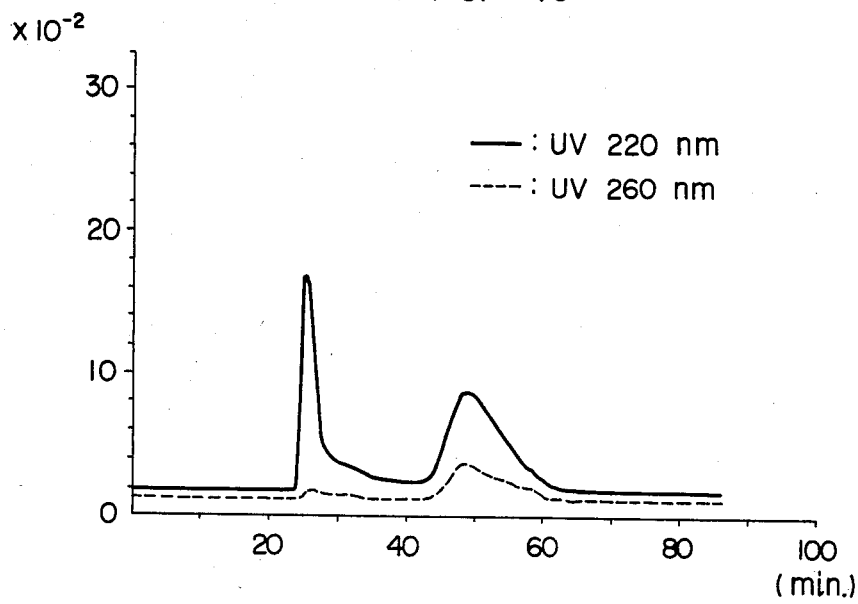
FIG. 49 shows a high performance liquid chromatogram of said substance.
Figure 50:
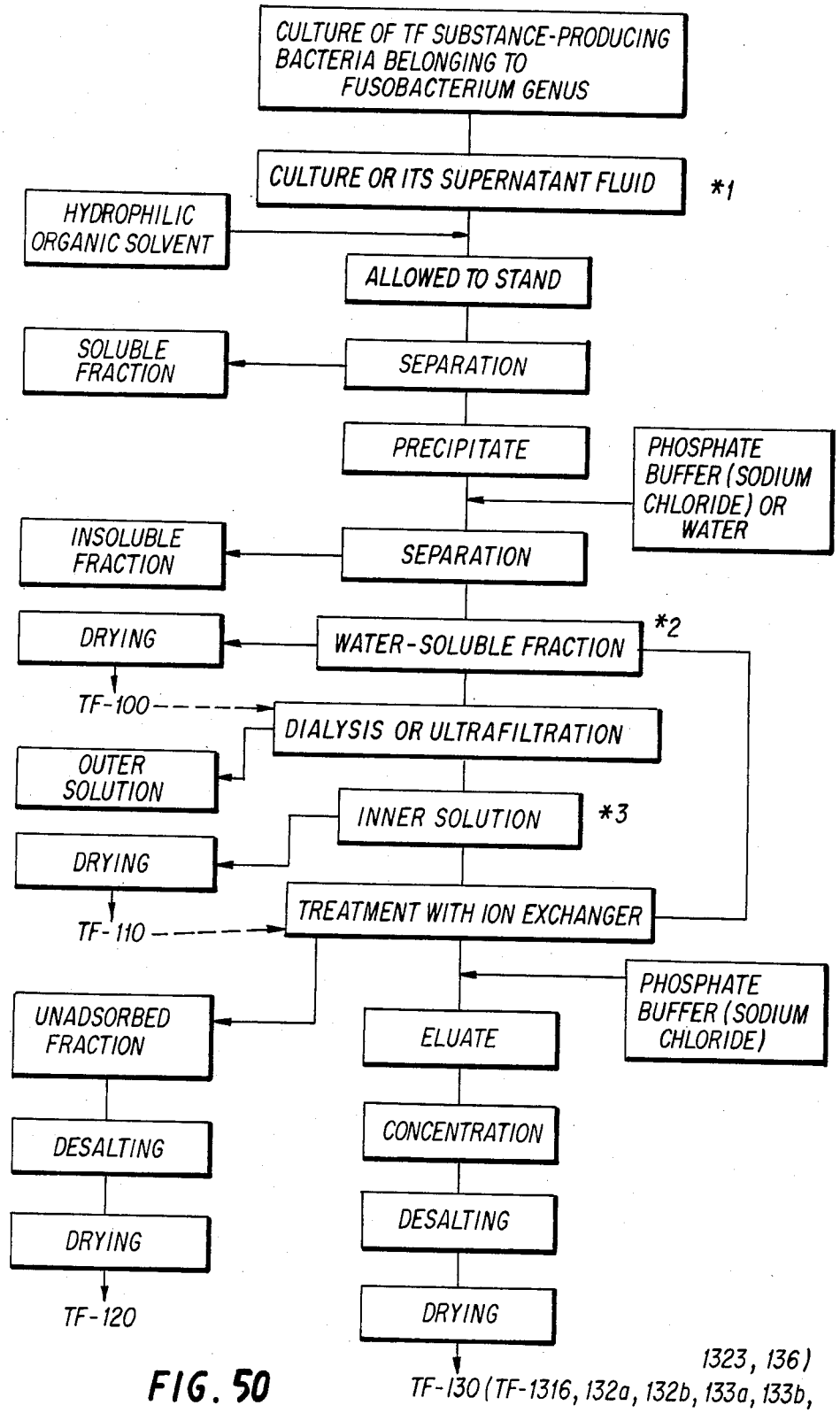
Figure 51:
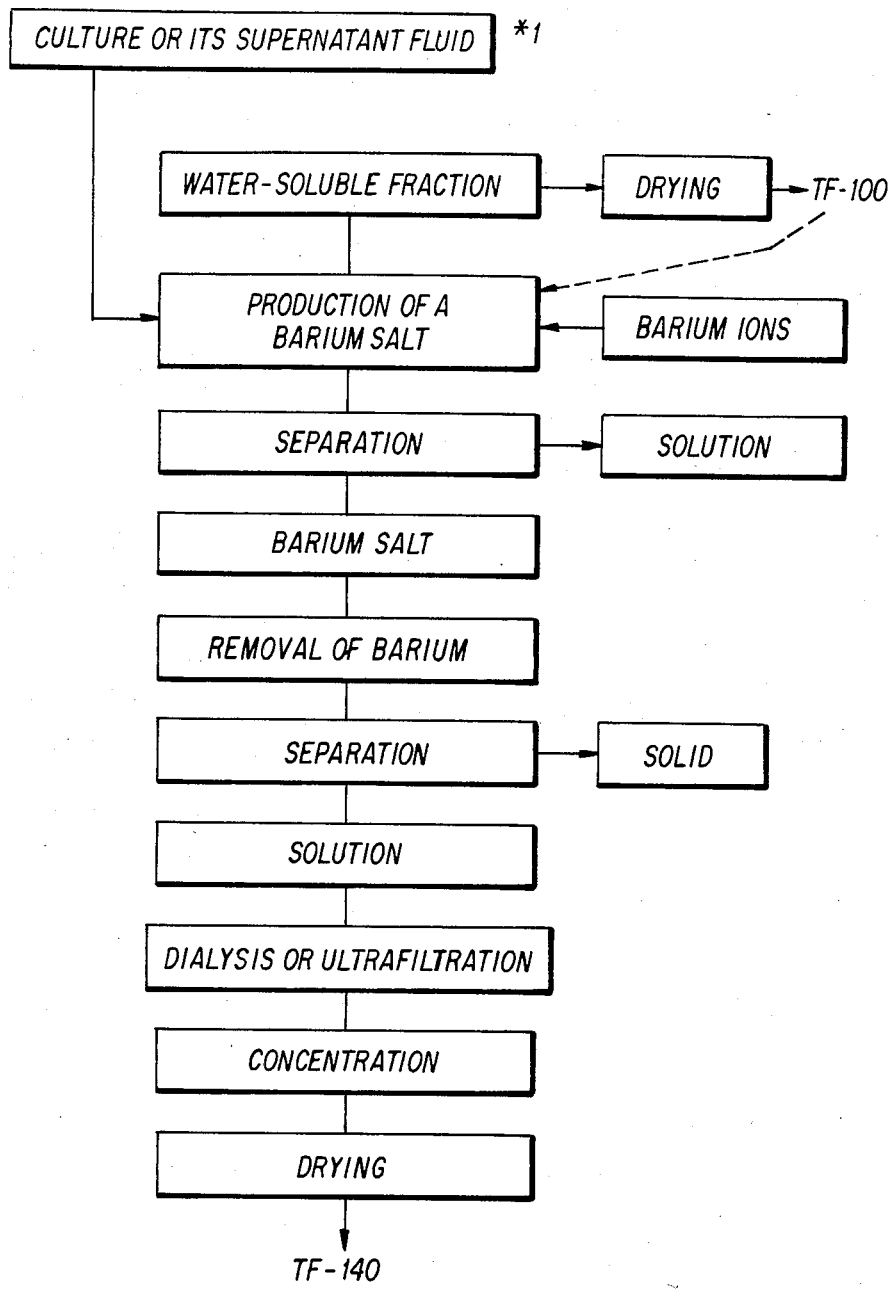
Figure 52:
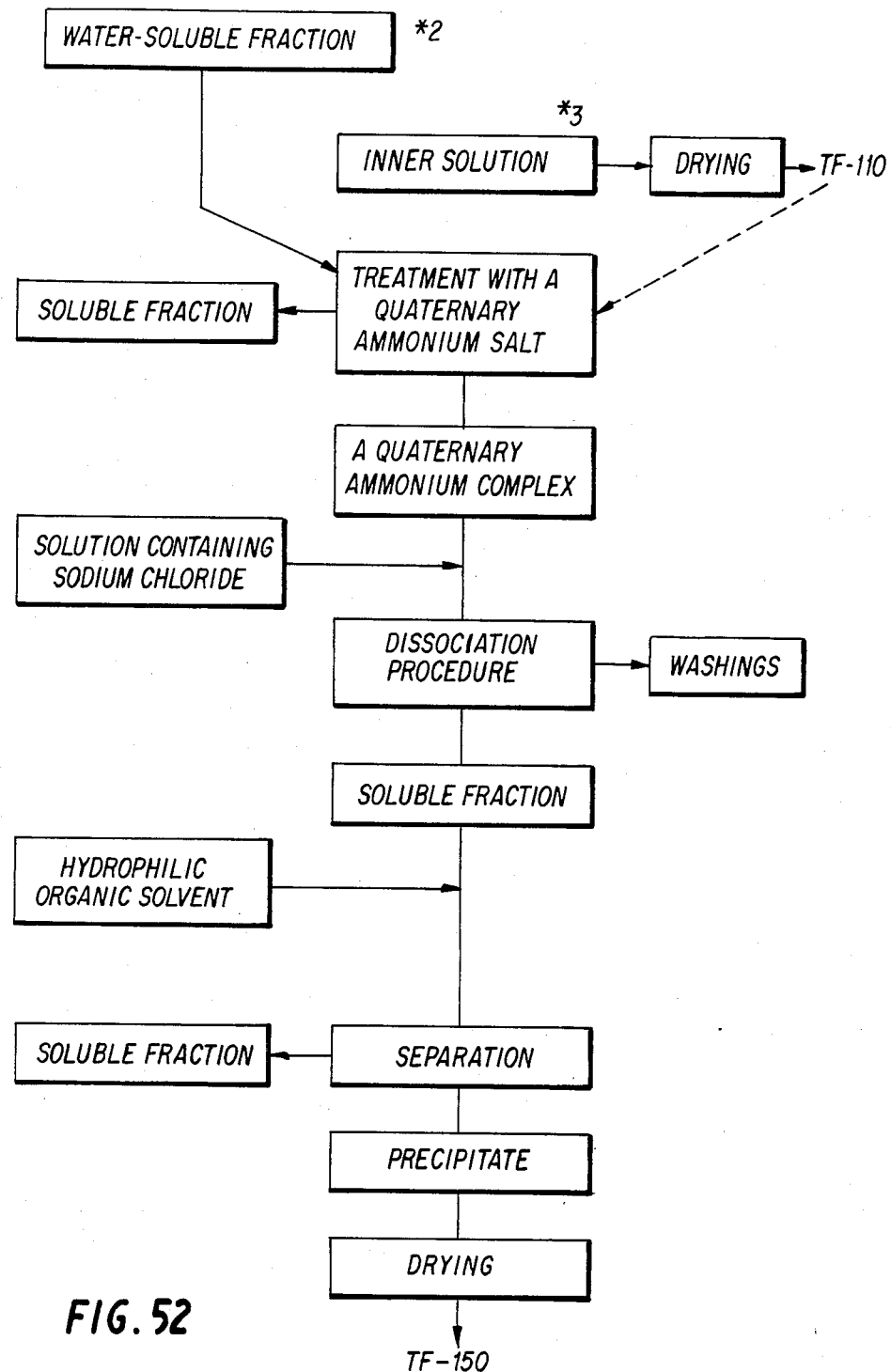

(1) In each of 15 two-liter culture bottles each equipped with a screw cap was placed 2 liters of a culture medium containing 34 g of trypticase peptone, 6 g of phytone peptone, 20 g of proteose peptone, 70 g of a brain-heart-infusion, 6 g of yeast extract, 15 g of sodium chloride, 12 g of glucose, 10 g of lactose, 0.5 g of L-cystine, 0.2 g of sodium sulfite, 1.0 g of sodium thioglycolate and 1.4 g of agar and the culture medium was adjusted to a pH of 7. The culture medium was sterilized under at 1.2 atm at 120° C. for 15 minutes, was warmed in boiling water bath for 20 min., and thereafter immediately water-cooled, after which a preculture solution of *Fusobacterium nucleatum* TF-031 previously prepared by culturing it in a culture medium having the same composition as above was inoculated into the above water-cooled culture medium under sterile conditions in an amount of 100 ml per culture bottle, and subjected to steady-state culture in an incubator at 37° C. for 48 hours. After the completion of the culture, the culture was centrifuged for removing organisms at 4,000 r.p.m. at 5° C. for 20 minutes. The amount of the supernatant fluid obtained was about 27 liters.

(2) To the supernatant fluid obtained in above (1) was added 40 liters of ethanol with stirring at 5° C., and the resulting mixture was allowed to stand in a low temperature room until the amorphous precipitate was completely settled. Subsequently, the mixture was centrifuged at 6,000 r.p.m. at 5° C. for 15 minutes, and the precipitate was collected, washed with ethanol, and then dried under reduced pressure to obtain about 60 g of crude powder.

(3) In 120 ml of water was dissolved 20 g of the crude powder obtained in above (2), and the water-insoluble materials formed at this time were removed by centrifugation at 7,500 r.p.m. for 10 minutes, after which the water-soluble fraction thus obtained was combined with washings obtained by washing the water-insoluble materials twice with 60-ml portions of water, and the resulting solution was dried under reduced pressure to obtain 14 g of grayish white-light brown powder of TF-100.

EXAMPLE 2

The solution described in Example 1-(3) which was prepared by combining the water-soluble fraction free from the water-insoluble materials with the washings obtained by washing the water-insoluble materials was subjected to ultrafiltration by using a hollow fiber type ultrafiltration system (membrane No. HI-1: manufactured by Asahi Kasei Kogyo Kabushiki Kaisha), and the inner solution was subjected to lyophilization to obtain 10 g of grayish white-light brown powder of TF-110.

EXAMPLE 3

In a small amount of water was dissolved 10 g of the powder obtained in Example 2, and the resulting solution was applied to a column packed with diethylaminoethyl-Sephadex A-50 equilibrated with a 0.025M phosphate buffer having a pH of 8, and the eluted solution was collected. Further, 2.5 liters of the same phosphate buffer as above was passed through the column, and the eluted solution obtained was combined with the eluted solution previously collected, after which the resulting solution was desalted by using a hollow fiber type ultrafiltration system (membrane No. HI-1), concentrated under reduced pressure, and then subjected to lyophilization to obtain 470 mg of grayish white-light brown powder of TF-120.

EXAMPLE 4

In 24 ml of water was dissolved 2 g of the powder obtained in Example 1-(2), and the water-insoluble materials were removed by centrifugation at 7,500 r.p.m. for 10 minutes. The water-soluble fraction was dialyzed overnight against distilled water at 5° C. by using a cellophane tube, and the inner solution was concentrated under reduced pressure. Subsequently, the concentrated solution was applied to a column packed with 150 ml of diethylaminoethyl-Sephadex A-50 which had previously been equilibrated with a 0.025 M phosphate buffer having a pH of 8, and the column was washed by passing therethrough 600 ml of a 0.025M phosphate buffer having a pH of 8, after which a 0.025M phosphate buffer having a sodium chloride concentration of 0.6M and a pH of 8 was passed through the column to obtain an eluate. The eluate was concentrated under reduced pressure to about 100 ml, dialyzed against distilled water at 5° C., again concentrated under reduced pressure, desalted by using a column of Sephadex G-25, and then subjected to lyophilization to obtain 470 mg of grayish white—light brown TF-1316.

EXAMPLE 5

The solution described in Example 1-(3) which was prepared by combining the water-soluble fraction free from water-insoluble materials and the washings obtained by washing the water-insoluble materials was dialyzed overnight against distilled water at 5° C. by using a cellophane tube, and the inner solution was concentrated under reduced pressure. The concentrated solution was then applied to a column packed with 50 g of diethylaminoethyl-Sephadex A-50 which had previously been equilibrated with a 0.025M phosphate buffer having a pH of 8, and 2 liters of a 0.025M phosphate buffer having a pH of 8 and 2.5 liters of a 0.025M phosphate buffer having a sodium chloride concentration of 0.1M and a pH of 8 were successively passed through the column, after which 2.5 liters of a 0.025M phosphate buffer having a sodium chloride concentration of 0.2M and a pH of 8 was passed through the column in order to elute the active substance adsorbed on the column, and the eluted solution obtained was desalted by using a hollow fiber type ultrafiltration system (membrane No. HI-1), and then subjected to lyophilization to obtain 600 mg of grayish white—light brown powder of TF-132a.

EXAMPLE 6

In 1.2 liters of a 0.025 M phosphate buffer having a sodium chloride concentration of 0.3M and a pH of 8 was dissolved 44.2 g of the powder obtained in Example 1-(2), and the suspended insoluble materials were removed by filtration by using Hyflo Super Cel, after which the filtrate obtained was applied to a column of 33 cm in diameter packed with 500 ml of diethylaminoethyl-Sephadex A-50 which had previously been equilibrated with a 0.025M phosphate buffer having a sodium chloride concentration of 0.3M and a pH of 8, and the eluted solution was collected. The column was washed with a 0.025M phosphate buffer having a sodium chloride concentration of 0.3M and a pH of 8, and the washings were combined with the above-mentioned eluted solution to obtain 1.67 liters of a solution. The solution was again applied to a column of 8 cm in diameter packed with 400 ml of diethylaminoethyl-Sephadex A-50 which had previously been equilibrated with a 0.025M phosphate buffer having a sodium chloride concentration of 0.3M and a pH of 8 to obtain 1.68 liters of an eluted solution. The column was washed with a 0.025M phosphate buffer having a sodium chloride concentration of 0.3M and a pH of 8 to obtain 1.64 liters of washings. The eluted solution and the washings were combined, and a 0.025M phosphate buffer having a pH of 8 was added thereto to obtain 4.98 liters of a 0.025M phosphate buffer having a sodium chloride concentration of 0.2M and a pH of 8. The thus obtained buffer solution was applied to a column of 8 cm in diameter packed with 500 ml of diethylaminoethyl-Sephadex A-50 which had previously been equilibrated with a 0.025M phosphate buffer having a sodium chloride concentration of 0.2M and a pH of 8, and the column was washed with 2 liters of a 0.025 M phosphate buffer having a sodium chloride concentration of 0.2M and a pH of 8. To 7 liters of a solution prepared by combining the washings with the eluted solution was added a 0.025M phosphate buffer having a pH of 8 to obtain 14 liters of a 0.025M phosphate buffer having a sodium chloride concentration of 0.1M and a pH of 8. The eluted solution thus obtained was applied to a column of 8 cm in diameters packed with 500 ml of diethylaminoethyl-Sephadex A-50 which had previously been equilibrated with a 0.025M phosphate buffer having a sodium chloride concentration of 0.1M and a pH of 8, and the eluted solution was removed. The column was washed with 2 liters of a 0.025M phosphate buffer having a sodium chloride concentration of 0.1M and a pH of 8, after which 2 liters of a 0.025M phosphate buffer having a sodium chloride concentration of 0.2M and a pH of 8 was passed through the column, and the eluted solution was collected. The eluted solution was concentrated and desalted by using an ultrafiltration system (the filter used: Toyo Ultrafilter UK-10), further desalted by using a Sephadex G-25 column, decolorized by active carbon, and then subjected to lyophilization to obtain 880 mg of grayish white—light brown powder of TF-132b.

EXAMPLE 7

In a small amount of water was dissolved 10 g of the powder obtained in Example 2, and the resulting solution was applied to a column packed with diethylaminoethyl-Sephadex A-50 which had previously been equilibrated with a 0.025M phosphate buffer having a pH of 8. Subsequently, 5 liters of a 0.025M phosphate buffer having a sodium chloride concentration of 0.2M and a pH of 8 was passed through the column, after which 2.5 liters of a 0.025M phosphate buffer having a sodium chloride concentration of 0.3M and a pH of 8 was passed through the column in order to elute the active substance adsorbed on the column, and the eluted solution obtained was concentrated under reduced pressure. The concentrated solution was desalted by using a cellophane tube, completely desalted by using Sephadex G-25, and then subjected to lyophilization to obtain 600 mg of grayish white—light brown powder of TF-133a.

EXAMPLE 8

In 1.2 liters of a 0.025M phosphate buffer having a sodium chloride concentration of 0.3M and a pH of 8 was dissolved 44.2 g of the powder obtained in Example 1-(2), and the suspended insoluble materials were removed by filtration by using Hyflo Super Cel, after which the filtrate obtained was applied to a column of 33 cm in diameter packed with 500 ml of diethylaminoethyl-Sephadex A-50 which had previously been equilibrated with a 0.025M phosphate buffer having a sodium chloride solution of 0.3M and a pH of 8, and the eluted solution was collected. The column was washed with a 0.025M phosphate buffer having a sodium chloride concentration of 0.3M and a pH of 8, and the washings were combined with the aforesaid eluted solution to obtain 1.67 liters of a solution. The solution was again applied to a column of 8 cm in diameter packed with 40 ml of diethylaminoethyl-Sephadex A-50 which had previously been equilibrated with a 0.025M phosphate buffer having sodium chloride concentration of 0.3M and a pH of 8 to obtain 1.68 liters of an eluted solution. The column was washed with a 0.025M phosphate buffer having a sodium chloride concentration of 0.3M and a pH of 8 to obtain 1.64 liters of washings. The eluted solution and the washings were combined, and a 0.025M phosphate buffer having a pH of 8 was added thereto to obtain 4.98 liters of a 0.025M phosphate buffer having a sodium chloride concentration of 0.2M and a pH of 8. The eluted solution thus obtained was applied to a column of 8 cm in diameter packed with 500 ml of diethylaminoethyl-Sephadex A-50 which had previously been equilibrated with a 0.025M phosphate buffer having a sodium chloride concentration of 0.2M and a pH of 8, and the column was washed with a 0.025M phosphate buffer having a sodium chloride concentration of 0.2M and a pH of 8, after which 2 liters of a 0.025M phosphate buffer having a sodium chloride concentration of 0.3M and a pH of 8 was passed through the column, and the eluted solution was collected. The eluted solution was concentrated and desalted by using an ultrafiltration system (the filter used: Toyo Ultrafilter UK-10), further desalted by using a Sephadex G-25 column, decolorized by active carbon, and then subjected to lyophilization to obtain 590 mg of grayish white—light brown powder of TF-133b.

EXAMPLE 9

(1) In 120 ml of water was dissolved 20 g of the crude powder obtained in Example 1-(2), and the water-insoluble materials formed at this time were removed by centrifugation at 7,500 r.p.m. for 10 minutes, after which the water-soluble fraction thus obtained and washings obtained by washing the water-insoluble materials twice with 60-ml portions of water were combined, and then subjected to ultrafiltration by using a hollow fiber type ultrafiltration system (membrane No. HI-1), and the inner solution was subjected to lyophilization to obtain 10 g of grayish white—light brown powder.

(2) In 1 liter of a 0.025M phosphate buffer having a sodium chloride concentration of 0.3M and a pH of 8 was dissolved 25 g of the powder obtained by the above (1) treatment, and the resulting solution was applied to a column of 33 cm in diameter packed with 500 ml of diethylaminoethyl-Sephadex A-50 which had previously been equilibrated with a 0.025M phosphate buffer having a sodium chloride concentration of 0.3M and a pH of 8. The column was similarly washed with a 0.025M phosphate buffer having a sodium chloride concentration of 0.3M and a pH of 8, and the eluted solution and the washings were combined to obtain 1.6 liters of a mixture. The mixture was applied to a column of 8 cm in diameter packed with 400 ml of diethylaminoethyl-Sephadex A-50 similarly equilibrated with a 0.025M phosphate buffer having a sodium chloride concentration of 0.3M and a pH of 8 to obtain 1.65 liters of an eluted solution. The eluted solution was combined with 1.7 liters of the washings obtained by washing the column with a 0.025M phosphate buffer having a sodium chloride concentration of 0.3M and a pH of 8, and the resulting mixture was diluted with a 0.025M phosphate buffer having a pH of 8 to prepare 10.35 liters of a 0.025M phosphate buffer having a sodium chloride concentration of 0.1M and a pH of 8.

Subsequently, the buffer solution thus obtained was applied to a column of 8 cm in diameter packed with 500 ml of diethylaminoethyl-Sephadex A-50 which had previously been equilibrated with a 0.025M phosphate buffer having a sodium chloride concentration of 0.1M and a pH of 8, and the column was washed with 2 liters of a 0.025M phosphate buffer having a sodium chloride concentration of 0.1M and a pH of 8, after which 2 liters of a 0.025M phosphate buffer having a sodium chloride concentration of 0.3M and a pH of 8 was passed through the column, and the eluted solutions were collected. The eluted solution obtained was desalted and concentrated by using an ultrafiltration system (the filter used: Toyo Ultrafilter UK-10), and further desalted on Sephadex G-25, decolorized by active carbon, and then subjected to lyophilization to obtain 1.65 g of grayish white—light brown powder of TF-1323.

EXAMPLE 10

In a small amount of water was dissolved 10 g of the powder obtained in Example 2, and the resulting solution was applied to a column packed with diethylaminoethyl-Sephadex A-50 which had previously been equilibrated with a 0.025M phosphate buffer having a pH of 8. Subsequently, 6 liters of a 0.025M phosphate buffer having a sodium chloride concentration of 0.5M and a pH of 8 was passed through the column, after which 2.5 liters of a 0.025M phosphate buffer having a sodium chloride concentration of 0.6M and a pH of 8 was passed through the column in order to elute the active substance adsorbed on the column, and the transit solution obtained was desalted by using a hollow fiber type ultrafiltration system (membrane No. HI-1), concentrated under reduced pressure, and then subjected to lyophilization to obtain 130 mg of grayish white—light brown powder of TF-136.

EXAMPLE 11

In 200 ml of water was dissolved 15 g of the crude powder obtained in Example 1-(2), and the water-insoluble materials were removed by centrifugation at 7,500 r.p.m. for 10 minutes, after which the water-soluble fraction thus obtained was adjusted to pH 10 by adding dropwise thereto a 0.2M aqueous barium hydroxide solution. White precipitate was deposited by the addition of the aqueous barium hydroxide solution. Barium ions were added so that the concentration of the total barium ions to the final volume was 0.01M, after which the solution was stirred for 30 minutes, and the precipitate was collected by filtration. The precipitate thus obtained of a barium salt was suspended in 10 ml of a 10% by weight aqueous sodium sulfate solution, sufficiently stirred, and then filtered, and the filtrate was collected. The precipitate was again suspended, stirred and then filtered in the same manner as above once with 10 ml of a 10% by weight aqueous sodium sulfate solution and twice with 5-ml portions of said solution, and each filtrate was collected. Further, the remaining precipitate was washed twice with 10-ml portions of water, and then filtered to obtain washings. The above-mentioned filtrate collected and the washings were combined, dialyzed against distilled water, concentrated under reduced pressure, and then subjected to lyophilization to obtain 0.45 g of grayish white—light brown powder of TF-140.

EXAMPLE 12

In 450 ml of water was dissolved 32 g the powder obtained in Example 1-(2), and the suspended insoluble materials were removed by filtration using Hyflo Super Cel, after which the filtrate obtained was dialyzed overnight against running water by using a cellophane tube. To the dialyzed solution was added dropwise 80 ml of a 20% by weight aqueous cetyl pyridinium chloride solution with stirring while adding thereto 200 ml of a 10% by weight borate buffer (pH 9.0), and the resulting mixture was stirred at room temperature for 30 minutes, after which the precipitate was collected by filtration. The precipitate was suspended in 150 ml of a 0.1% by weight borate buffer (pH 9.0) containing 0.1M of sodium chloride and 0.2% by weight of cetyl pyridinium chloride, and the resulting suspension was stirred for 30 minutes. Subsequently, the precipitate was collected from the suspension by filtration, and again suspended in 150 ml of a borate buffer (pH 9.0) of the above-mentioned composition, and the suspension thus obtained was stirred for 30 minutes, after which the precipitate was collected by filtration. The collected precipitate was suspended in 150 ml of a 0.1% by weight borate buffer (pH 9.0) containing 0.5M of sodium chloride and 0.2% of cetyl pyridinium chloride, and the resulting suspension was stirred and dissociated for 30 minutes. Subsequently, the precipitate was separated from the suspension by filtration to obtain a soluble fraction. Further, the precipitate separated by filtration was again subjected to the same dissociation procedure as above to obtain a soluble fraction. The two soluble fraction were combined, and the resulting soluble fraction was adjusted to pH 3 to 4 with 10% hydrochloric acid, after which ethanol was added thereto so that its concentration might finally be a 80% by volume. The resulting solution was allowed to stand overnight at 5° C., and the precipitate formed was collected by filtration to obtain 5.6 g of grayish white—light brown powder of TF-150.

PREPARATION EXAMPLE 1

Each vial was packed with 1 mg or 5 mg of each of the powders of TF-100, 110 and 120 obtained in Examples 1, 2 and 3. The powders are dissolved in a sterilized physiological salt solution, a solution containing 0.5% of lidocaine, or the like when used, and then used as injections.

PREPARATION EXAMPLE 2

Each vial was packed with 1 mg or 5 mg of each of the powders of TF-1316, 132a and 132b obtained in Examples 4, 5 and 6. The powders are dissolved in a sterilized physiological salt solution, a solution containing 0.5% of lidocaine, or the like when used as injections.

PREPARATION EXAMPLE 3

A vial was packed with 1 mg or 5 mg of the powder of TF-133a obtained in Example 7. The powder is dissolved in a sterilized physiological salt solution, a solution containing 0.5% of lidocaine or the like when used, and then used as an injection.

PREPARATION EXAMPLE 4

A vial was packed with 1 mg or 5 mg of the powder of TF-133b obtained in Example 8. The powder is dissolved in a sterilized physiological salt solution, a solution containing 0.5% of lidocaine, or the like when used, and then used as an injection.

PREPARATION EXAMPLE 5

A vial as packed with 1 mg or 5 mg of the powder of TF-1323 obtained in Example 9. The powder is dissolved in a sterilized physiological salt solution, a solution containing 0.5% of lidocaine, or the like when used, and then used as an injection.

PREPARATION EXAMPLE 6

Each vial was packed with 1 mg or 5 mg of each of the powders TF-136, 140 and 150 obtained in Examples 10, 11 and 12. The powders are dissolved in a sterilized physiological salt solution, a solution containing 0.5% of lidocaine, or the like when used, and then used as injections.

What is claimed is:

1. A substance TF-100 having the following properties:
    (a) Grayish white—light brown powder,
    (b) It inhibits the proliferation of mouse Ehrlich ascites tumor and Ehrlich solid tumor, and has an immunostimulating activity,
    (c) It is soluble in water and it is insoluble in methanol, ethanol, acetone, benzene, chloroform, ethyl acetate and diethyl ether,
    (d) It has no clear melting point, begins to decompose at about 110° C., and decomposes remarkably above 200° C.,
    (e) Its infrared absorption spectrum obtained by a KBr tablet method has absorption bands in the vicinity of 3600–3200, 2960–2930, 1670–1640, 1550, 1440–1380, 1240, 1140–1000 and 820 cm$^{-1}$,
    (f) The ultraviolet absorption spectrum of its aqueous solution shows a strong absorption at the absorption edge, and shows an absorption peak in the vicinity of 256–260 nm,
    (g) When it is fractionated by gel filtration (column: 50 mm$\phi$×600 mm, eluent: distilled water) by using Sephadex G-50 (registered trademark of Pharmacia Co., Ltd.), it has absorption bands at the elution volumes in the vicinity of the void volume—400, 430–530, 700–800, and 840–870 ml in the ultraviolet absorbance measurement at 260 nm; and at the elution volumes in the vicinity of the void volume—390, and 410–430 ml in the absorbance measurement at 620 nm by an anthrone-sulfuric acid method,
    (h) Its high performance liquid chromatogram (eluent: a 0.1M phosphate buffer having a pH of 7, flow rate: 0.8 ml/min., at room temperature) obtained by using TSK-GEL G3000 SW (trade name of Toyo Soda Co., Ltd., column: 7.9 mm$\phi$×600 mm×2) has peaks in the vicinity of the solvent front, 38–60, and 65 min. in the ultraviolet absorbance measurement at 220 nm and 260 nm,
    (i) It is positive in Molisch reaction,, phenol-sulfuric acid reaction, anthrone-sulfuric acid reaction, indole-hydrochloric acid reaction, Lowry-Folin's reaction, and ninhydrin reaction,
    (j) Elementary analysis values C: 30.6–35.7%, H: 4.2–5.2%, N: 4.2–5.2%
    (k) Its saccharide content measured by a phenol-sulfuric acid method is about 40.0—about 46.0% by weight in terms of glucose, and its protein content measured by Lowry-Folin's method is about 20.0—about 23.0% by weight in terms of calf serum albumin.

2. A substance TF-110 having the following properties:
    (a) Grayish white-light brown powder,
    (b) It inhibits the proliferation of mouse Ehrlich ascites tumor, and has an immunostimulating activity, (c) It is soluble in water and it is insoluble in methanol, ethanol, acetone, benzene, chloroform, ethyl acetate and diethyl ether, (d) It has no clear melting point, begins to decompose at about 110° C., and decomposes remarkably above 200° C., (e) Its infrared absorption spectrum obtained by a KBr tablet method has absorption bands in the vicinity of 3600–3200, 2960–2930, 1670–1640, 1550, 1440–1380, 1240, 1140–1000 and 820 cm$^{-1}$, (f) The ultraviolet absorption spectrum of its aqueous solution shows strong absorption at the absorption edge, and shows an absorption peak in the vicinity of 256–260 nm, (g) When it is fractionated by gel filtration (column: 44 mm$\phi$×500 mm, eluent: a 0.1M phosphate buffer having a pH of 7) by using Sephadex G-200 (registered trademark of Pharmacia Co., Ltd.), it has absorption bands at the elution volumes in the vicinity of the void volume—380, and 600–920 ml in the ultraviolet absorbance measurement at 260 nm, at the elution volumes in the vicinity of the void volume—380, 420–520, and 630–760 ml in the absorbance measurement at 490 nm by a phenol-sulfuric acid method; and at the elution volumes in the vicinity of the void volume—380, 420–520, and 620–760 ml in the absorbance measurement at 620 nm by an anthrone-sulfuric acid method, (h) Its high performance liquid chromatogram (eluent: a 0.1M phosphate buffer having a pH of 7, flow rate: 0.8 ml/min., at room temperature) obtained by using TSK-GEL G3000 SW (trade name of Toyo Soda Co., Ltd., column: 7.9 mm$\phi$×600 mm×2) has peaks in the vicinity of the solvent front, 38–60, and 65 min. in the ultraviolet absorbance measurement at 220 nm and 260 nm, (i) It is positive in Molisch reaction, phenol-sulfuric acid reaction, anthrone-sulfuric acid reaction, indole-hydrochloric acid reaction and Lowry-Folin's reaction, and negative in ninhydrin reaction, (j) Elementary analysis values C: 35.9–41.0%, H: 4.5–5.2%, N: 4.2–5.2%

(k) Its saccharide content measured by a phenol-sulfuric acid method is about 30.0—about 69.0% by weight in terms of glucose, and its protein content measured by Lowry-Folin's method is about 18.0—about 22.0% by weight in terms of calf serum albumin.

3. A substance TF-120 having the following properties:

(a) Grayish white-light brown powder, (b) It inhibits the proliferation of mouse Ehrlich ascites tumor, and has an immunostimulating activity, (c) It is soluble in water and it is insoluble in methanol, ethanol, acetone, benzene, chloroform, ethyl acetate, and diethyl ether, (d) It has no clear melting point, begins to decompose at about 110° C., and decomposes remarkably above 200° C., (e) Its infrared absorption spectrum obtained by a KBr tablet method has absorption bands in the vicinity of 3600–3200, 2960–2930, 1670–1640, 1550, 1380–1360, 1140–1000 and 820 cm$^{-1}$, (f) The ultraviolet absorption spectrum of its aqueous solution shows strong absorption at the absorption edge, and shows an absorption peak in the vicinity of 268–272 nm, (g) When it is fractionated by gel filtration (column: 44 mm$\phi$×500 mm, eluent: a 0.1M phosphate buffer having a pH of 7) by using Sephadex G-200 it has absorption bands at the elution volumes in the vicinity of the volid volume—325, and 775–875 ml in the ultraviolet absorbance measurement at 260 nm; at the elution volumes in the vicinity of the void volume—360, 360–480, and 510–760 ml in the absorbance measurement at 490 nm by a phenol-sulfuric acid method; and at the elution volumes in the vicinity of the void volume—380, 420–520, and 620–760 ml in the absorbance measurement at 620 nm by an anthrone-sulfuric acid method, (h) Its high performance liquid chromatogram (eluent: a 0.1M phosphate buffer having a pH of 7, flow rate: 0.8 ml/min., at room temperature) obtained by using TSK-GEL G3000 SW (column: 7.9 mm$\phi$×600 mm×2) has peaks in the vicinity of the solvent front, 38–60 min. in the ultraviolet absorbance measurement at 220 nm and 260 nm, (i) It is positive in Molisch reaction, phenol-sulfuric acid reaction, anthrone-sulfuric acid reaction, indole-hydrochloric acid reaction and Lowry-Folin's reaction, and negative in ninhydrin reaction, (j) Elementary analysis values C: 35.1–40.2%, H: 4.5–5.5%, N: 2.0–3.1%

(k) Its saccharide content measured by a phenol-sulfuric acid method is about 56.0—about 73.0% by weight in terms of glucose, and its protein content measured by Lowry-Folin's method is about 9.0—about 13.0% by weight in terms of calf serum albumin.

4. A substance TF-130 having the following properties:

(a) Grayish white-light brown powder, (b) It inhibits the proliferation of mouse Ehrlich ascites tumor, Ehrlich solid tumor and Sarcoma-180 carcinoma, and has an immunostimulating activity, (c) It is soluble in water and it is insoluble in methanol, ethanol, acetone, benzene, chloroform, ethyl acetate and diethyl ether, (d) It has no clear melting point, begins to decompose at about 110° C., and decomposes remarkably above 200° C., (e) Its infrared absorption spectrum obtained by a KBr tablet method has absorption bands in the vicinity of 3600–3200, 2960–2930, 1670–1640, 1550, 1440–1380, 1240, 1140–1000 and 820 cm$^{-1}$, (f) The ultraviolet absorption spectrum of its aqueous solution shows a strong absorption at the absorption edge, and shows an absorption peak in the vicinity of 256–280 nm, (g) It is positive in Molisch reaction, phenol-sulfuric acid reaction, anthrone-sulfuric acid reaction, indole-hydrochloric acid reaction and Lowry-Folin's reaction, and negative in ninhydrin reaction, (h) Elementary analysis values C: 27.5–39.8%, H: 3.2–5.7%, N: 2.8–6.3%

(i) Its saccharide content measured by a phenol-sulfuric acid method is about 19.0—about 64.0% by weight in terms of glucose, and its protein content measured by Lowry-Folin's method is about 6.0—about 28.0% by weight in terms of calf serum albumin.

5. A substance TF-1316 having the following properties:

(a) Grayish white-light brown powder,
(b) It inhibits the proliferation of mouse Ehrlich ascites tumor, Ehrlich solid tumor and Sarcoma-180 carcinoma, and has an immunostimulating activity,
(c) It is soluble in water and it is insoluble in methanol, ethanol, acetone, benzene, chloroform, ethyl acetate and diethyl ether,
(d) It has no clear melting point, begins to decompose at about 110° C., and decomposes remarkably above 200° C.,
(e) Its infrared absorption spectrum obtained by a KBr tablet method has absorption bands in the vicinity of 3600–3200, 2960–2930, 1670–1640, 1550, 1440–1380, 1240, 1140–1000 and 820 $cm^{-1}$,
(f) The ultraviolet absorption spectrum of its aqueous solution shows strong absorption at the absorption edge, and shows an absorption peak in the vicinity of 256–260 nm,
(g) When it is fractionated by gel filtration (column: 21 mm$\phi$×400 mm, eluent: a 0.1M phosphate buffer having a pH of 7) by using Sephadex G-200, it has an absorption band at the elution volumes in the vicinity of the void volume—160 ml in the ultraviolet absorbance measurement at 260 nm; and an absorption band at the elution volumes in the vicinity of the void volume—160 ml in the absorbance measurement at 490 nm by a phenol-sulfuric acid method,
(h) Its high performance liquid chromatogram (eluent: a 0.1M phosphate buffer having a pH of 7, flow rate: 0.8 ml/min., at room temperature) obtained by using TSK-GEL G3000 SW (column: 7.9 mm$\phi$×600 mm×2) has peaks in the vicinity of the solvent front, and 40–60 min. in the ultraviolet absorbance measurement at 220 nm, and in the vicinity of the solvent front, and 40–60 min. in the ultraviolet absorbance measurement at 260 nm,
(i) It is positive in Molisch reaction, phenol-sulfuric acid reaction, anthrone-sulfuric acid reaction, indole-hydrochloric acid reaction and Lowry-Folin's reaction, and negative in ninhydrin reaction,
(j) Elementary analysis values C: 30.0–34.0%, H: 3.8–4.4%, N: 4.9–5.7%
(k) Its saccharide content measured by a phenol-sulfuric acid method is about 35.0—about 50.0% by weight in terms of glucose, and its protein content measured by Lowry-Folin's method is about 10.0—about 23.0% by weight in terms of calf serum albumin.

6. A substance TF-132a having the following properties:
(a) Grayish white-light brown powder,
(b) it inhibits the proliferation of mouse Ehrlich ascites tumor, Ehrlich solid tumor and Sarcoma-180 carcinoma, and has an imunostimulating activity,
(c) It is soluble in water and it is insoluble in methanol, ethanol, acetone, benzene, chloroform, ethyl acetate and diethyl ether,
(d) It has no clear melting point, begins to decompose at about 110° C., and decomposes remarkably above 200° C.,
(e) Its infrared absorption spectrum obtained by a KBr tablet method has absorption bands in the vicinity of 3600–3200, 2960–2930, 1670–1640, 1550, 1440–1380, 1240, 1140–1000 and 820 $cm^{-1}$,
(f) The ultraviolet absorption spectrum of its aqueous solution shows strong absorption at the absorption edge, and shows an absorption peak in the vicinity of 270–280 nm,
(g) When it is fractionated by gel filtration (column: 44 mm$\phi$×500 mm, eluent: a 0.1M phosphate buffer having a pH of 7) by using Sephadex G-200, it has absorption bands at the elution volumes in the vicinity of the void volume—340, 600–700, and 720–880 ml in the ultraviolet absorbance measurement at 260 nm; at the elution volumes in the vicinity of the void volume—340, 340–580, and 720–900 ml in the absorbance measurement at 490 nm by a phenol-sulfuric acid; and at the elution volumes in the vicinity of the void volume—340, and 340–580 ml in the absorbance measurement at 620 nm by an anthrone-sulfuric acid method,
(h) Its high performance liquid chromatogram (eluent: a 0.1M phosphate buffer having a pH of 7, flow rate: 0.8 ml/min., at room temperature) obtained by using TSK-GEL G3000 SW (column: 7.9 mm$\phi$×600 mm×2) has peaks in the vicinity of the solvent front, 30, 38–60, and 65 min. in the ultraviolet absorbance measurement at 220 nm; and in the vicinity of the solvent front, 62, and 65 min. in the ultraviolet absorbance measurement at 260 nm,
(i) It is positive in Molisch reaction, phenol-sulfuric acid reaction, anthrone-sulfuric acid reaction, indole-hydrochloric acid reaction, and Lowry-Folin's reaction, and negative in ninhydrin reaction,
(j) Elementary analysis values C: 34.8–39.8%, H: 4.5–5.7%, N: 2.8–3.6%
(k) Its saccharide content measured by a phenol-sulfuric acid method is about 55.0—about 64.0% by weight in terms of glucose, and its protein content measured by Lowry-Folin's method is about 18.0—about 28.0% by weight in terms of calf serum albumin.

7. A substance TF-132b having the following properties:
(a) Grayish white-light brown powder,
(b) It inhibits the proliferation of mouse Ehrlich ascites tumor, Ehrlich solid tumor and Sarcoma-180 carcinoma, and has an immunostimulating activity,
(c) It is soluble in water and it is insoluble in methanol, ethanol, acetone, benzene, chloroform, ethyl acetate and diethyl ether,
(d) It has no clear melting point, begins to decompose at about 110° C., and decomposes remarkably above 200° C.,
(e) Its infrared absorption spectrum obtained by a KBr tablet method has absorption bands in the vicinity of 3600–3200, 2960–2930, 1670–1640, 1550, 1440–1380, 1240, 1140–1000 and 820 $cm^{-1}$,
(f) The ultraviolet absorption spectrum of its aqueous solution shows a strong absorption at the absorption edge, and has a shoulder in the vicinity of 265–280 nm,
(g) When it is fractionated by gel filtration (column: 21 mm$\phi$×400 mm, eluent: a 0.1M phosphate buffer having a pH of 7) by using Sephadex G-200, it has a weak absorption band at the elution volumes in the vicinity of the void volume—150 ml in the ultraviolet absorbance measurement at 260 nm; and an absorption band at the elution volumes in the vicinity of the void volume—150 ml in the absorbance measurement at 490 nm by a phenol-sulfuric acid method, (h) Its high performance liquid chromatogram (eluent: a 0.1M phosphate buffer having a pH of 7, flow rate: 0.8 ml/min., at room temperature) obtained by using TSK-GEL G3000 SW (column: 7.9 mm$\phi$×600 mm×2) has peaks in the vicinity of the solvent front, 36–37, and 48–50 min. in the ultraviolet absorbance measurement at 220 nm, and has very low peaks in the vicinity of the solvent front, 32–39, and 45–52 min. in the ultraviolet absorbance measurement at 260 nm, (i) It is positive in Molisch reaction, phenol-sulfuric acid reaction, anthrone-sulfuric acid reaction, indole-hydrochloric acid reaction and Lowry-Folin's reaction, and negative in ninhydrin reaction, (j) Elementary analysis values C: 35.3–39.5%, H: 4.5–5.6%, N: 2.8–5.4%

(k) Its saccharide content measured by a phenol-sulfuric acid method is about 23.6—about 45.5% by weight in terms of glucose, and its protein content measured by Lowry-Folin's method is about 15.5—about 28.0% by weight in terms of calf serum albumin.

8. A substance TF-133a having the following properties:

(a) Grayish white-light brown powder, (b) It inhibits the proliferation of mouse Ehrlich ascites tumor, Ehrlich solid tumor, Sarcoma-180 carcinoma, and has an immunostimulating activity, (c) It is soluble in water and it is insoluble in methanol, ethanol, acetone, benzene, chloroform, ethyl acetate and diethyl ether, (d) It has no clear melting point, begins to decompose at about 110° C., and decomposes remarkably above 200° C., (e) Its infrared absorption spectrum obtained by a KBr tablet method has absorption bands in the vicinity of 3600–3200, 2960–2930, 1670–1640, 1550, 1440–1380, 1240, 1140–1000 and 820 cm$^{-1}$, (f) The ultraviolet absorption spectrum of its aqueous solution shows strong absorption at the absorption edge, and shows an absorption peak in the vicinity of 258–262 nm, (g) When it is fractionated by gel filtration (column: 44 mm$\phi$×500 mm, eluent: a 0.1M phosphate buffer having a pH of 7) by using Sephadex G-200, it has absorption bands at the elution volumes in the vicinity of the void volume—300, and 630–940 ml in the ultraviolet absorbance measurement at 260 nm; an absorption band at the elution volumes in the vicinity of the void volume—420 ml in the absorbance measurement at 490 nm by a phenol-sulfuric acid method; and an absorption band at the elution volumes in the vicinity of the void volume—420 ml in the absorbance measurement at 620 nm by an anthrone-sulfuric acid method, (h) Its high performance liquid chromatogram (eluent: a 0.1M phosphate buffer having a pH of 7, flow rate: 0.8 ml/min., at room temperature) obtained by using TSK-GEL G3000 SW (column: 7.9 mm$\phi$×600 mm×2) has peaks in the vicinity of the solvent front, 38, and 50 min. in the ultraviolet absorbance measurement at 220 nm; and in the vicinity of the solvent front, 50–60, and 62 min. in the ultraviolet absorbance measurement at 260 nm, (i) It is positive in Molisch reaction, phenol-sulfuric acid reaction, anthrone-sulfuric acid reaction, indole-hydrochloric acid reaction and Lowry-Folin's reaction, and negative in ninhydrin reaction, (j) Elementary analysis values C: 28.0–36.6%, H: 3.5–5.1%, N: 4.5–6.3%

(k) Its saccharide content measured by a phenol-sulfuric acid method is about 26.0—about 35.0% by weight in terms of glucose, and its protein content measured by Lowry-Folin's method is about 22.0—about 28.0% by weight in terms of calf serum albumin.

9. A substance TF-133b having the following properties:

(a) Grayish white-light brown powder, (b) It inhibits the proliferation of mouse Ehrlich ascites tumor, Ehrlich solid tumor and Sarcoma-180 carcinoma, and has an immunostimulating activity, (c) It is soluble in water and it is insoluble in methanol, ethanol, acetone, benzene, chloroform, ethyl acetate and diethyl ether, (d) It has no clear melting point, begins to decompose at about 110° C., and decomposes remarkably above 200° C., (e) Its infrared absorption spectrum obtained by a KBr tablet method has absorption bands in the vicinity of 3600–3200, 2960–2930, 1670–1640, 1550, 1440–1380, 1240, 1140–1000 and 820 cm$^{-1}$, (f) The ultraviolet absorption spectrum of its aqueous solution shows a strong absorption at the absorption edge, and has a shoulder in the vicinity of 270–280 nm, (g) When it is fractionated by gel filtration (column: 21 mm$\phi$×400 mm, eluent: a 0.1M phosphate buffer having a pH of 7) by using Sephadex G-200, it has an absorption band at the elution volumes in the vicinity of the void volume—170 ml in the ultraviolet absorbance measurement at 260 nm; and an absorption band at the elution volumes in the vicinity of the void volume—150 ml in the absorbance measurement at 490 nm by a phenol-sulfuric acid method, (h) Its high performance liquid chromatogram (eluent: a 0.1M phosphate buffer having a pH of 7, flow rate: 0.8 ml/min., at room temperature) obtained by using TSK-GEL G3000 SW (column: 7.9 mm$\phi$×600 mm×2) has peaks in the vicinity of the solvent front, 49–50 min. in the ultraviolet absorbance measurement at 220 nm; and in the vicinity of the solvent front, 38–39 and 52 min. in the ultraviolet absorbance measurement at 260 nm, (i) It is positive in Molisch reaction, phenol-sulfuric acid reaction, anthrone-sulfuric acid reaction, indole-hydrochloric acid reaction and Lowry-Folin's reaction, and negative in ninhydrin reaction, (j) Elementary analysis values C: 31.1–38.5%, H: 3.9–5.2%, N: 3.4–4.7%

(k) Its saccharide content measured by a phenol-sulfuric acid method is about 19.0—about 24.5% by weight in terms of glucose, and its protein content measured by Lowry-Folin's method is about 12.9—about 22.9% by weight in terms of calf serum albumin.

10. A substance TF-1323 having the following properties:

(a) Grayish white-light brown powder, (b) It inhibits the proliferation of mouse Ehrlich ascites tumor, Ehrlich solid tumor and Sarcoma-180 carcinoma, and has an immunostimulating activity, (c) It is soluble in water and it is insoluble in methanol, ethanol, acetone, benzene, chloroform, ethyl acetate and diethyl ether, (d) It has no clear melting point, begins to decompose at about 110° C., and decomposes remarkably above 200° C., (e) Its infrared absorption spectrum obtained by a KBr tablet method has absorption bands in the vicinity of 3600–3200, 2960–2930, 1670–1640, 1550, 1440–1380, 1240, 1140–1000 and 820 cm$^{-1}$, (f) The ultraviolet absorption spectrum of its aqueous solution shows strong absorption at the absorption edge, and shows a shoulder in the vicinity of 265–280 nm, (g) When it is fractionated by gel filtration (column: 21 mm$\phi$×400 mm, eluent: a 0.1M phosphate buffer having a pH of 7) by using Sephadex G-200, it has an absorption band at the elution volumes in the vicinity of the void volume—160 ml in the ultraviolet absorbance measurement at 260 nm; and an absorption band at the elution volumes in the vicinity of the void volume—150 ml in the absorbance measurement at 490 nm by a phenol-sulfuric acid method, (h) Its high performance liquid chromatogram (eluent: a 0.1M phosphate buffer having a pH of 7, flow rate: 0.8 ml/min., at room temperature) obtained by using TSK-GEL G3000 SW (column: 7.9 mm$\phi$×600 mm×2) has peaks in the vicinity of the solvent front, 36, and 48–50 min. in the ultraviolet absorbance measurement at 220 nm; and peaks in the vicinity of the solvent front, 36 and 50 min. in the ultraviolet absorbance measurement at 260 nm, (i) It is positive in Molisch reaction, phenolsulfuric acid reaction, anthrone-sulfuric acid reaction, indole-hydrochloric acid reaction and Lowry-Folin's reaction, and negative in ninhydrin reaction, (j) Elementary analysis values C: 29.9–39.4%, H: 3.9–5.6%, N: 2.8–5.4%

(k) Its saccharide content measured by a phenolsulfuric acid method is about 19.0—about 25.0% by weight in terms of glucose, and its protein content measured by Lowry-Folin's method is about 11.0—about 17.0% by weight in terms of calf serum albumin.

11. A substance TF-136 having the following properties:

(a) Grayish white-light brown powder, (b) It inhibits the proliferation of mouse Ehrlich ascites tumor, Ehrlich solid tumor and Sarcoma-180 carcimona, and has an immunostimulating activity, (c) It is soluble in water and it is insoluble in methanol, ethanol, acetone, benzene, chloroform, ethyl acetate and diethyl ether, (d) It has no clear melting point, begins to decompose at about 110° C., and decomposes remarkably above 200° C., (e) Its infrared absorption spectrum obtained by a KBr tablet method has absorption bands in the vicinity of 3600–3200, 2960–2930, 1670–1640, 1550, 1440–1380, 1240, 1140–1000 and 820 cm$^{-1}$, (f) The ultraviolet absorption spectrum of its aqueous solution shows a strong absorption at the absorption edge, and shows an absorption peak in the vicinity of 256–260 nm, (g) When it is fractionated by gel filtration (column: 44 mm$\phi$×500 mm, eluent: a 0.1M phosphate buffer having a pH of 7) by using Sephadex G-200, it has absorption bands at the elution volumes in the vicinity of 540–930 ml in the ultraviolet absorbance measurement at 260 nm, and all the fractions have a slight absorption band in the absorbance measurement at 490 nm by a phenol-sulfuric acid method and in the absorbance measurement at 620 nm by an anthronesulfuric acid method, (h) Its high performance liquid chromatogram (eluent: a 0.1M phosphate buffer having a pH of 7, flow rate: 0.8 ml/min., at room temperature) obtained by using TSK-GEL G3000 SW (column: 7.9 mm$\phi$×600 mm×2) has peaks in the vicinity of the solvent front, 28–40, and 42–60 min. in the ultraviolet absorbance measurement at 220 nm; and peaks in the vicinity of the solvent front and 42–60 min. in the ultraviolet absorbance measurement at 260 nm, (i) It is positive in Molisch reaction, phenolsulfuric acid reaction, anthrone-sulfuric acid reaction, indole-hydrochloric acid reaction and Lowry-Folin's reaction, and negative in ninhydrin reaction, (j) Elementary analysis values C: 27.5–32.6%, H: 3.2–4.0%, N: 5.0–6.1%

(k) Its saccharide content measured by a phenolsulfuric acid method is about 19.0—about 30.0% by weight in terms of glucose, and its protein content measured by Lowry-Folin's method is about 6.0—about 12.0% by weight in terms of calf serum albumin.

12. A substance TF-140 having the following properties:

(a) Grayish white-light brown powder, (b) It inhibits the proliferation of mouse Ehrlich ascites tumor, and has an immunostimulating activity, (c) It is soluble in water and it is insoluble in methanol, ethanol, acetone, benzene, chloroform, ethyl acetate and diethyl ether, (d) It has no clear melting point, begins to decompose at about 210° C., and decomposes remarkably above 280° C., (e) Its infrared absorption spectrum obtained by a KBr tablet method has absorption bands in the vicinity of 3600–3200, 2960–2930, 1670–1640, 1550, 1440–1380, 1240, 1140–1000 and 820 cm$^{-1}$, (f) The ultraviolet absorption spectrum of its aqueous solution shows a strong absorption at the absorption edge, and shows an absorption peak in the vicinity of 255–260 nm, (g) When it is fractionated by gel filtration (column: 44 mm$\phi$×500 mm, eluent: 0.1M phosphate buffer having a pH of 7) by using Sephadex G-200, it has absorption bands at the elution volumes in the vicinity of the void volume—300, 500–900, and 900–1000 ml in the ultraviolet absorbance measurement at 260 nm; and at the elution volumes in the vicinity of the void volume—500, 650–850, and 850–1000 ml in the absorbance measurement at 490 nm by a phenolsulfuric acid method, (h) Its high performance liquid chromatogram (eluent: a 0.1M phosphate buffer having a pH of 7, flow rate: 0.8 ml/min., at room temperature) obtained by using TSK-GEL G3000 SW (column: 7.9 mm$\phi$×600 mm×2) has peaks in the vicinity of the solvent front, and 40–60 min. in the ultraviolet absorbance measurement at 220 nm and 260 nm, (i) It is positive in Molisch reaction, phenolsulfuric acid reaction, anthrone-sulfuric acid reaction, indole-hydrochloric acid reaction and Lowry-Folin's reaction, and negative in ninhydrin reaction,
(j) Elementary analysis values C: 22.0–28.0%, H: 3.0–3.5%, N: 5.0–6.5%
(k) Its saccharide content measured by a phenolsulfuric acid method is about 5.0—about 15.0% by weight in terms of glucose, and its protein content measured by Lowry-Folin's method is about 23.0%—about 32.0% by weight in terms of calf serum albumin.

13. A substance TF-150 having the following properties:
(a) Grayish white-light brown powder,
(b) It inhibits the proliferation of mouse Ehrlich ascites tumor, and has an immunostimulating activity,
(c) It is soluble in water and it is insoluble in methanol, ethanol, acetone, benzene, chloroform, ethyl acetate and diethyl ether,
(d) It has no clear melting point, begins to decompose at about 110° C., and decomposes remarkably above 200° C.,
(e) The ultraviolet absorption spectrum of its aqueous solution shows a strong absorption at the absorption edge, and shows an absorption peak in the vicinity of 255–260 nm,
(f) Its infrared absorption spectrum obtained by a KBr tablet method has absorption bands in the vicinity of 3600–3200, 2960–2930, 1670–1640, 1550, 1440–1380, 1240, 1140–1000 and 820 cm$^{-1}$,
(g) When it is fractionated by gel filtration (column: 21 mm$\phi$×400 mm, eluent: a 0.1M phosphate buffer having a pH of 7.0) by using Sephadex G-200, it has absorption bands at the elution volumes in the vicinity of the void volume—100, and 100–160 ml in the ultraviolet absorbance measurement at 260 nm; and an absorption band at the elution volumes in the vicinity of the void volume—150 ml in the absorbance measurement at 490 nm by a phenol-sulfuric acid method,
(h) Its high performance liquid chromatogram (eluent: a 0.1M phosphate buffer having a pH of 7.0, flow rate: 0.8 ml/min., at room temperature) obtained by using TSK-GEL G3000 SW (column: 7.9 mm$\phi$×600mm×2) has peaks in the vicinity of the solvent front, 32, and 48–50 min. in the ultraviolet absorbance measurement at 220 nm; and in the vicinity of the solvent front, 32, and 48–50 min. in the ultraviolet absorbance measurement at 260 nm,
(i) It is positive in Molisch reaction, phenolsulfuric acid reaction, anthrone-sulfuric acid reaction, indole-hydrochloric acid reaction and Lowry-Folin's reaction, and negative in ninhydrin reaction,
(j) Elementary analysis values C: 31.0–34.0%, H: 4.0–4.4%, N: 2.8–3.2%
(k) Its saccharide content measured by a phenolsulfuric acid method is about 40.0—about 55.0% by weight in terms of glucose, and its protein content measured by Lowry-Folin's method is about 7.0— about 14% by weight in terms of calf serum albumin.

14. A process for preparing a TF-substance which is TF-100 as defined in claim 1, TF-110 as defined in claim 2, TF-120 as defined in claim 3, TF-130 as defined in claim 4, TF-1316 as defined in claim 5, TF-132a as defined in claim 6, TF-132b as defined in claim 7, TF-133a as defined in claim 8, TF-133b as defined in claim 9, TF-1323 as defined in claim 10, TF-136 as defined in claim 11, TF-140 as defined in claim 12 or TF-150 as defined in claim 13 which comprises the steps of culturing under anaerobic conditions in a culture medium, until substantial TF-substance is produced in said medium, TF-substance-producing bacteria belonging to the Fusobacterium nucleatum species and having the identifying characteristics of Fusobacterium nucleatum TF-031 (Ferm 5077, ATCC 31647), wherein the culture medium used for culturing the bacteria contains nitrogen sources, carbon sources, vitamin sources, reducing agents and inorganic salts, or contains them and agar and collecting the TF-substance from the culture or its supernatant fluid.

15. A process according to claim 14 in which the step of culturing under anaerobic conditions occurs at a pH of 5 to 8.5 and at 30° to 45° C. and the TF substance is collected by adding a precipitating agent to the culture so produced or to its supernatant fluid, said precipitating agent being a hydrophilic organic solvent at a concentration of 30 to 70% by volume and at a pH of 2 to 7 or barium ions at a concentration of 0.005 to 0.1M at a pH of 10 to 13 supplied by a source of barium ions, allowing a precipitate to form, collecting the precipitate, removing the precipitating agent from the precipitate, separating a TF-substance containing fraction as the water-soluble fraction from the precipitate, and collecting the said TF-substances from the water-soluble fraction.

16. A process according to claim 15, wherein the precipitating agent is a hydrophilic organic solvent.

17. A process according to claim 16, wherein the water-soluble fraction of the precipitate is taken out of the precipitate and then dried.

18. A process according to claim 16, wherein the precipitate formed is collected; the water-soluble fraction of the precipitate is subjected to dialysis or ultrafiltration to remove low-molecular-weight substances and inorganic materials; and TF-substances are collected from the inner solution.

19. A process according to claim 16, wherein the precipitate formed is collected; the water-soluble fraction of the precipitate is, if necessary, subjected to dialysis or ultrafiltration to remove low-molecular-weight substances and inorganic materials, and then treated with a weakly basic ion exchanger; and the unadsorbed fraction is collected.

20. A process according to claim 16, wherein the precipitate formed is collected; the water-soluble fraction of the precipitate is, if necessary, subjected to dialysis or ultrafiltration to remove low-molecular-weight substances and inorganic materials, and then treated with a weakly basic ion exchanger; and TF-substances are collected from the adsorbed fraction.

21. A process according to claim 20, wherein the ion exchanger is a weakly basic ion exchanger having a molecular sievability.

22. A process according to claim 20, wherein the adsorbed fraction is treated with a 0.6M sodium chloride-phosphate buffer; and the eluted fraction is collected.

23. A process according to any claim 22, wherein the pH of the phosphate buffer containing sodium chloride used for treating the adsorbed fraction is about 8.

24. A process according to claim 22, wherein the fraction which has been subjected to the ion exchanger treatment is subjected to concentration, desalting and drying.

25. A process according to claim 20, wherein a fraction which has not been eluted with a 0.1M sodium chloride-phosphate buffer but has been eluted with a 0.2M sodium chloride-phosphate buffer is collected from the adsorbed fraction.

26. A process according to claim 20, wherein a fraction which has not been eluted with a 0.2M sodium chloride-phosphate buffer but has been eluted with a 0.3M sodium chloride-phosphate buffer is collected.

27. A process according to claim 20, wherein a fraction which has not been eluted with a 0.1M sodium chloride-phosphate buffer but has been eluted with a 0.3M sodium chloride-phosphate buffer is collected.

28. A process according to claim 20, wherein a fraction which has not been eluted with a 0.5M sodium chloride-phosphate buffer but has been eluted with a 0.6M sodium chloride-phosphate buffer is collected.

29. A process according to claim 20, wherein a 0.6–0.6M sodium chloride-phosphate buffer is used for eluting the fraction adsorbed on the ion exchanger.

30. A process according to claim 20, wherein the bacteria are inoculated into a culture medium adjusted to pH 7.2 to 8.2 comprising trypticase peptone, phytone peptone, proteose peptone, a brain-heart-infusion (or a heart infusion), yeast extract, sodium chloride, glucose, lactose, L-cystine, sodium sulfite and thioglycollate, or into a culture medium comprising them and agar, and then cultured under anaerobic conditions at 36° to 38° C. for 1 to 3 days; an alcohol is added to the culture or its supernatant fluid in a concentration of 50 to 70% by volume; the precipitate formed is collected; the water-soluble fraction of the precipitate is, if necessary, subjected to dialysis or ultrafiltration, and then treated with a weakly basic ion exchanger or a weakly basic ion exchanger having a molecular sievability to remove the unadsorbed fraction; a fraction which has been eluted with a 0.1 or 0.2M sodium chloride-phosphate buffer is removed from the adsorbed fraction; and thereafter a fraction which has been eluted with a 0.3M sodium chloride-phosphate buffer is collected, concentrated, desalted and then dried.

31. A process according to claim 20, wherein the bacteria are inoculated into a culture medium adjusted to pH 7.2 to 8.2 comprising trypticase peptone, phytone peptone, proteose peptone, a brain-heart-infusion (or a heart infusion), yeast extract, sodium chloride, glucose, lactose, L-cystine, sodium sulfite and thioglycollate, or a culture medium comprising them and agar, and then cultured under anaerobic conditions at 36° to 38° C. for 1 to 3 days; an alcohol is added to the culture or its supernatant fluid in a concentration of 50 to 70% by volume; the precipitate formed is collected; if necessary, the water-soluble fraction of the precipitate is subjected to dialysis or ultrafiltration and then a 0.2–0.3M sodium chloride-phosphate buffer of the water-soluble fraction of the precipitate or a 0.2–0.3M sodium chloride-phosphate buffer of the inner solution component obtained by dialysis or ultrafiltration, is treated with a weakly basic ion exchanger or a weakly basic ion exchanger having a molecular sievability which has been equilibrated with a 0.2–0.3M sodium chloride-phosphate buffer; the fraction which has passed through the ion exchanger is collected; this eluted solution is adjusted to have a sodium chloride concentration of 0.1 to 0.2M, and then treated with a weakly basic ion exchanger or a weakly basic ion exchanger having a molecular sievability which has been equilibrated with a 0.1–0.2M sodium chloride-phosphate buffer, to be adsorbed thereon; and a fraction which has been eluted with a 0.2–0.3M sodium chloride-phosphate buffer is collected from the adsorbed fraction, concentrated, desalted, and then dried.

32. A process according to claim 16, wherein the precipitate formed is collected; if necessary, the water-soluble fraction of the precipitate is subjected to dialysis or ultrafiltration to remove low-molecular-weight substances and inorganic materials, a 0.2–0.3M sodium chloride-phosphate buffer of the water-soluble fraction of the precipitate, or a 0.2–0.3M sodium chloride-phosphate buffer of the inner solution component obtained by the dialysis or ultrafiltration is prepared, and then treated with a weakly basic ion exchanger equilibrated with a 0.2–0.3M sodium chloride-phosphate buffer; a fraction which has passed through the ion exchanger is collected; this eluted solution is then adjusted so that its sodium chloride concentration may be 0.1M, and thereafter treated with a weakly basic ion exchanger equilibrated with a 0.1M sodium chloride-phosphate buffer to be adsorbed thereon; and subsequently, a fraction which has not been eluted with a 0.1M sodium chloride-phosphate buffer but has been eluted with a 0.2 or 0.3M sodium chloride-phosphate buffer is collected.

33. A process according to claim 16, wherein the precipitate formed is collected; if necessary, the water-soluble fraction of the precipitate is subjected to dialysis or ultrafiltration to remove low-molecular-weight substances and inorganic materials, a 0.3M sodium chloride-phosphate buffer of the water-soluble fraction of the precipitate or a 0.3M sodium chloride-phosphate buffer of inner solution component obtained by the dialysis or ultrafiltration is prepared, and then treated with a weakly basic ion exchanger equilibrated with a 0.3M sodium chloride-phosphate buffer; a fraction which has passed through the ion exchanger is collected; the sodium chloride concentration of this eluted solution is then adjusted to 0.2M, and the solution is thereafter treated with a weakly basic ion exchanger equilibrated with a 0.2M sodium chloride-phosphate buffer to be adsorbed thereon; and subsequently, a fraction which has not been eluted with a 0.2M sodium chloride-phosphate buffer but has been eluted with 0.3 M sodium chloride-phosphate buffer is collected.

34. A process according to any claim 16, wherein the hydrophilic organic solvent added to the culture or its supernatant fluid is an alcohol.

35. A process according to claim 15, wherein barium ions are added to the culture or its supernatant fluid to form a barium salt, or a hydrophilic organic solvent is added to the culture, or its supernatant fluid and the precipitate formed is collected and then barium ions are added to the water-soluble fraction of the precipitate thus collected, or barium ions are added to a solution of a powder obtained by drying the said water-soluble fraction of the precipitate, to form a barium salt; the barium salt formed is collected and then subjected to removal of barium; and the water-soluble fraction is collected and subjected to dialysis or ultrafiltration to remove low-molecular-weight substances and inorganic materials.

36. A process according to claim 15, wherein a hydrophilic organic solvent is added to the culture or its supernatant fluid; the precipitate formed is collected; the water-soluble fraction of the precipitate, or the inner solution component obtained by subjecting the water-soluble fraction to dialysis or ultrafiltration to remove low-molecular-weight substances and inorganic materials, is treated with a quaternary ammonium salt; the precipitate formed is collected and then subjected to a dissociation procedure using a solution containing sodium chloride; a hydrophilic organic solvent is added to the soluble fraction obtained to form a precipitate; and the precipitate thus formed is collected.

37. A process according to claim 36, wherein the quaternary ammonium salt is cetyl pyridinium chloride.

38. A process according to claim 36, wherein the treatment with the quaternary ammonium salt is carried out in the presence of a borate buffer.

39. A process according to claim 36, wherein the solution containing sodium chloride is a borate buffer containing sodium chloride and a quaternary ammonium salt.

40. A process according to claim 15, wherein the culture medium used for culturing the bacteria comprising trypticase peptone, phytone peptone, proteose peptone, a brain-heart-infusion (or heart infusion), yeast extract, sodium chloride, glucose, lactose, L-cystine, sodium sulfite and thioglycollate, or comprising them and agar.

41. A process according to claim 15, wherein the culturing is carried out for 1 to 5 days.

42. A process according to claim 15, wherein the culture is carried out at 36° 1 to 38° C. for 1 to 3 days in a culture medium adjusted to pH 7.2 to 8.2.

43. A therapeutic composition for the treatment of cancerous tumors in lower warm-blooded animals comprising the substance TF-100, 110, 120, 130, 1316, 132a, 132b, 133a, 133b, 1323, 136, 140 or 150 according to claims 1, 2, 3, 4, 5, 6, 7, 8, 9, 10, 11, 12 or 13 in an amount effective to treat the tumor and a pharmaceutically acceptable adjuvant.

44. A therapeutic agent for the treatment of cancerous tumors in lower warm-blooded animals comprising the substance TF-132a, 132b, 133a, 133b or 1323 according to claims 6, 7, 8, 9 or 10 in an amount effective to treat the tumor and a pharmaceutically acceptable adjuvant.

45. A method for treating cancerous tumors in lower warm-blooded animals with the carcinostatic agent of claim 44 which comprises administering an amount thereof to the host mammal effective to treat the tumor.

* * * * *

UNITED STATES PATENT AND TRADEMARK OFFICE
CERTIFICATE OF CORRECTION

PATENT NO. : 4,744,985

DATED : May 17, 1988

INVENTOR(S) : Kenzo TAMAI et al.

It is certified that error appears in the above-identified patent and that said Letters Patent is hereby corrected as shown below:

On the Title Page, Item [30]:

Please add the following to the Foreign Application Priority Data:

-- Aug. 6, 1980 [JP] Japan .................. 55-108124 --

Signed and Sealed this

Seventh Day of February, 1989

*Attest:*

DONALD J. QUIGG

*Attesting Officer*     *Commissioner of Patents and Trademarks*